US006756226B2

(12) United States Patent
Graham et al.

(10) Patent No.: US 6,756,226 B2
(45) Date of Patent: Jun. 29, 2004

(54) ENHANCED SYSTEM FOR CONSTRUCTION OF ADENOVIRUS VECTORS

(76) Inventors: Frank L. Graham, 34 Amelia Street, Hamilton, Ontario (CA), L8P 2V4; Robin Parks, 2569 Hobson Road, Ottawa, Ontario (CA), K1V 8M6; Philip Ng, 39 Morgan Drive, Caledonia, Ontario (CA), N3W 1H6

( * ) Notice: Subject to any disclaimer, the term of this patent is extended or adjusted under 35 U.S.C. 154(b) by 0 days.

(21) Appl. No.: 09/981,648

(22) Filed: Oct. 16, 2001

(65) Prior Publication Data

US 2002/0168341 A1 Nov. 14, 2002

Related U.S. Application Data

(63) Continuation of application No. 09/415,899, filed on Oct. 8, 1999, now abandoned, which is a continuation-in-part of application No. 09/263,650, filed on Mar. 5, 1999, now Pat. No. 6,379,943, and a continuation-in-part of application No. 08/250,885, filed on May 31, 1994, now Pat. No. 6,140,087.

(51) Int. Cl.$^7$ .......................... C12N 15/64; C12N 1/00; C12N 15/00; C12N 15/09; C12N 15/63
(52) U.S. Cl. ................ 435/320.1; 435/91.4; 435/234.1; 514/44
(58) Field of Search .............................. 435/320.1, 91.4, 435/235.1; 514/44

(56) References Cited

U.S. PATENT DOCUMENTS 6,140,087 A * 10/2000 Graham et al. .......... 435/91.42
6,379,943 B1 * 4/2002 Graham et al. .......... 435/235.1

FOREIGN PATENT DOCUMENTS

WO    WO 97/25446    * 7/1997

OTHER PUBLICATIONS

Bett et al., Packaging capacity and stability of human adenovirus type 5 vectors, 1993, Journal of Virology, vol. 67, pp. 5911–5921.*
Palu et al., In pursuit of new developments for gene therapy of human diseases, 1999, Journal of Biotechnology, vol. 68, pp. 1–13.*
Bett et al., An efficient and flexible system for construction or adenovirus vectors with insertions of deletions in early regions 1 and 3, 1994, Proc. Natl. Acad. Sci. USA, vol. 91, pp. 8802–8806.*

* cited by examiner

Primary Examiner—James Ketter
Assistant Examiner—Konstantina Katcheves
(74) Attorney, Agent, or Firm—Joseph Fischer; Beusse, Brownlee, Wolter, Mora & Maire, P.A.

(57) ABSTRACT

In the present invention, viruses, plasmids or both are constructed which contain viral DNA, at least one head-to-head ITR junction, and optionally, recombinase recognition sites positioned such that site-specific recombination between recombinase recognition sites in separate plasmids results in generation of infectious viral DNA at high-efficiency in cotransfected host cells that have been engineered to express a site-specific recombinase. Because of the high-efficiency and specificity of the Cre enzyme, suitably engineered plasmids can be readily recombined to produce infectious virus at high-efficiency in cotransfected 293 cells, without, at the same time, producing wild-type adenovirus, with the attendant problems for removal thereof. Use of recombinases besides Cre and recombinase recognition sites besides lox sites, and use of cells other than 293 cells are also disclosed and enabled, as are kits incorporating the site-specific vector system, as well as compositions and methods for using such compositions as vaccines or in gene therapeutic applications. Enhancements in the efficiency of both site-specific and homologous recombination are provided by inclusion of at least one head-to-head ITR junction.

9 Claims, 33 Drawing Sheets

OLIGONUCLEOTIDES USED IN CLONING

SEQ. ID. NO.: 12 (AB16853) and SEQ. ID. NO.: 13 (AB16854)

SEQ. ID. NO.: 14 (AB16855) and SEQ. ID. NO.: 15 (AB16856)

CONSTRUCTION OF pCA36LOX and pCA36LOX Δ SHUTTLE PLASMIDS FOR RESCUE OF LACZ

Cotransfection of 293Cre cells with AdLC8c DNA-TP and a shuttle plasmid containing a loxP site for generation of Ad expression vectors

CONSTRUCTION OF pFG173lox

Restriction, transformation of E. coli, homologous recombination

CONSTRUCTION OF pFG23dX1lox AND pFG23dX1loxc FOR RESCUE OF MUTANT FIBRE INTO AD VIRUS

A PLASMID FOR RESCUE OF A FOREIGN DNA INTO AD VIRUS

CONSTRUCTION OF pAB14FL0X FOR ISOLATION OF AN AD VIRUS WITH A FLOXED FIBRE GENE

Isolation of a virus containing a fibre gene with flanking lox P sites.

COTRANSFECTION OF 293 CELLS
HOMOLOGOUS RECOMBINATION

NONDEFECTIVE ($E1^+$) VIRUS (ADFLOXFIBRE) CONTAINING A FLOXED FIBRE GENE

ENHANCED SYSTEM FOR CONSTRUCTION OF ADENOVIRUS VECTORS

CROSS REFERENCE TO RELATED APPLICATIONS

This application is a continuation of application Ser. No.: 09/415,899, filed Oct. 8, 1999, now abandoned which is a continuation-in-part of parent application Ser. No.: 09/263,650, filed Mar. 5, 1999, now U.S. Pat. No. 6,379,943. This application also is a continuation-in-part of application Ser. No.: 08/250,885, filed May 31, 1994, now U.S. Pat. No. 6,140,087. The benefit of priority under 35 USC §120 is claimed for all of the foregoing applications.

FIELD OF THE INVENTION

The present invention relates to methods for efficient and reliable construction of adenovirus vectors that contain and express foreign DNA and are useful for gene transfer into mammalian cells, for vaccines and for gene therapy. The vector system described herein is an improvement and modification of the two plasmid pBHG system, described in copending patent application Ser. No. 08/250,885, a foreign equivalent of which published as WO95/00655, hereby incorporated by reference, whereby a replication defective genomic adenoviral vector and a shuttle plasmid were recombined via homologous recombination in a cell in which they were cotransfected. This invention further represents an improvement over the Ser. No. 09/263,650 system whereby, through insertion of a head-to-head ITR junction in the shuttle plasmid, enhanced vector rescue efficiency is achieved, whether through homologous or site-specific recombination mechanisms.

BACKGROUND OF THE INVENTION

As taught in WO95/00655, adenoviruses (Ads) can be used as mammalian cell expression vectors, with excellent potential as live recombinant viral vaccines, as transducing vectors for gene therapy, for research, and for production of proteins in mammalian cells.

In the human Ad genome, early region 1 (E1), E3, and a site upstream of E4 have been utilized as sites for introducing foreign DNA sequences to generate adenovirus recombinants. In the absence of compensating deletions in E1 or E3, a maximum of about 2 kb can be inserted into the Ad genome to generate viable virus progeny. The E1 region is not required for viral replication in complementing 293 cells, or other cells known to complement E1, and up to approximately 3.2 kb can be deleted in this region to generate conditional helper independent vectors with a capacity of 5.0–5.2 kb. In the E3 region, which is not required for viral replication in cultured cells, deletions of various sizes have been utilized to generate nonconditional helper independent vectors with a capacity of up to 4.5–4.7 kb. The combination of deletions in E1 and E3 permits the construction and propagation of adenovirus vectors with a capacity for insertions of up to approximately 8 kb of foreign DNA.

The construction of Adenovirus vectors can be performed in many ways. One approach is to cotransfect permissive cells, usually, but not limited to, 293 cells, with a shuttle plasmid containing a portion of the left end of the Ad genome and, most commonly, having the E1 sequences replaced by a foreign DNA, and with DNA isolated from virions cleaved near the left end by a suitable restriction enzyme. Homologous recombination between overlapping viral DNA sequences of the shuttle plasmid and the virion DNA results in production of recombinant viruses containing the foreign DNA. A disadvantage of this method is the need to prepare purified viral DNA. In addition, such methods typically result in the presence of contaminating parental virus in the resulting vector preparations, such as when 100% of the viral DNA is not cleaved, or when the two viral DNA fragments produced by restriction cleavage are rejoined.

Another method has recently been described (Hardy S, Kitamura M, Harris-Stansil T, Dai Y, Phipps M L, "Construction of adenovirus vectors through Cre-lox recombination." J Virol March 1997; 71(3):1842–1849; see also PCT publication WO97/32481 relating to use of site-specific recombination of virus and helper dependent vectors) which involves infection of 293Cre cells (293 cells engineered to express Cre recombinase) with an Adenovirus containing a floxed packaging signal ($\Psi$) and transfection with a shuttle plasmid containing an ITR, a packaging signal and an expression cassette followed by a lox site, or cotransfection of 293Cre cells with purified deproteinized Adenoviral DNA and a shuttle plasmid. According to that method, Cre-mediated excision of the packaging signal from virus followed by site-specific recombination with the lox site in the shuttle plasmid produces a recombinant vector containing the expression cassette. However, as Cre action is not 100% efficient, the resulting virus preparations remain contaminated with parental virus, and must be passaged in 293Cre cells to eliminate the contaminating parental virus. A further disadvantage of this method is that it requires use of an infectious virus or DNA extracted from a virus as one of the starting materials, and is thus less attractive for commercial distribution than kits containing only bacterial plasmid DNA. Furthermore, the parental virus can recombine with Ad E1 sequences present in 293 cells, resulting in a virus containing a wild-type packaging signal and a wild-type E1 region. Such recombinant virus has the propensity to overgrow the original vector, leading to contamination of subsequent vector preparations with non-attenuated E1 expressing Ads.

One of the most frequently used and most popular methods for construction of adenovirus vectors is based on "the two plasmid method" (see Bett, A. J., Haddara, W., Prevec, L. and Graham, F. L An efficient and flexible system for construction of adenovirus vectors with insertions or deletions in early regions 1 and 3. Proc. Natl. Acad. Sci. US 91: 8802–8806, 1994), whereby suitable host cells (typically 293 cells) are cotransfected with two plasmids that separately are incapable of generating infectious virus, but which, when recombined within the transfected cell by homologous recombination, can generate replicating virus. The most widely used plasmids of this type are described in patent application Ser. No.08/250,885, and in PCT publication number WO95/00655, hereby incorporated by reference. That system has advantages over other methods using viruses or viral DNA as components since only easily-prepared plasmid DNAs are needed, and there is no background of parental virus that could contaminate the final vector isolates. Furthermore, the plasmids are not only easy and inexpensive to produce by those skilled in the art, but can be easily stored and transported, making them convenient for commercial distribution, (i.e. particularly when precipitated with ethanol or when lyophilized, these vectors do not require a cold chain for distribution). However, although this currently available system has proven utility and is widely used, the efficiency of virus production by homologous recombination can be low and variable, and the system cannot always be used easily by those not skilled in the art.

As demonstrated in the art (Anton, M. and Graham, F. L. "Site-specific recombination mediated by an adenovirus vector expressing the Cre recombinase protein: a molecular switch for control of gene expression," J. Virol. 69:4600–4606, 1995), and as described also in application Ser. No. 08/486,549 ("Adenoviruses for control of gene expression", hereby incorporated by reference), provision of Cre recombinase in Ad-infected cells can catalyse excision or rearrangement of viral DNA sequences that contain the target sites (lox P) for Cre-mediated site-specific recombination.

Such techniques are combined in the present invention with a head-to-head ITR containing shuttle plasmid to provide a long-needed advancement in the art of adenoviral vector production by enhancing the efficiency of vector production, whether through homologous recombination or site-specific recombination events.

SUMMARY OF THE INVENTION

In the present invention, viruses, plasmids or both are constructed which contain head-to-head ITR junctions, and optionally, wherein said viral DNA may also contain lox P sites positioned such that site-specific recombination between lox P sites in separate plasmids results in generation of infectious viral DNA at high-efficiency in cotransfected host cells that have been engineered to express the Cre recombinase. Such cells (293Cre cells) have been described by Parks, R. J., Chen, L., Anton, M., Sankar, U., Rudnicki, M. A. and Graham, F. L. "A new helper-dependent adenovirus vector system: removal of helper virus by Cre-mediated excision of the viral packaging signal," Proc. Natl. Acad. Sci. U.S. 93: 13565–13570, 1996, by Chen, L., Anton, M. and Graham, F. L., " Production and characterization of human 293 cell lines expressing the site-specific recombinase Cre," Somat. Cell and Molec. Genet. 22: 477–488, 1996, in U.S. patent application Ser. No. 08/473,168, and in PCT publication WO96/40955, hereby incorporated by reference for this purpose. Because of the high-efficiency and specificity of the Cre enzyme, suitably engineered plasmids can be readily recombined to produce infectious virus at high-efficiency in cotransfected 293 cells, without, at the same time, producing a contaminating parental adenovirus, with the attendant problems for removal thereof.

Due to the enhancement of recombination efficiency achieved by the instant invention, whereby a head-to-head ITR junction is included in the shuttle plasmid, even in the absence of site-specific recombination, enhanced efficiency is achieved in production of recombinant virus vectors.

In one embodiment of this invention a head-to-head ITR junction is included in the shuttle plasmid, whereby enhanced efficiency of production of recombinant virus vectors is achieved whether by homologous recombination or by site-specific recombination.

In a further embodiment of this invention, homologous recombination via cellular enzymes is replaced by site-specific recombination, via a recombinase such as Cre, FLP or the like, to join two DNAs that separately are noninfectious to form an infectious DNA molecule, wherein the efficiency of the site-specific recombination is enhanced by inclusion of head-to-head ITR junctions in the shuttle plasmids of a two-plasmid system. One application of the techniques disclosed herein is the isolation of "first generation" vectors with insertions of foreign DNA in E1. Such applications utilize a series of plasmids such as pBHGloxΔE1,3 (see FIG. 1, and variations and equivalents thereof), and various shuttle plasmids containing a head-to-head ITR junction, a packaging signal, an expression cassette, and a lox or other recombinase recognition site. Another application is in a sense the mirror image. Using a plasmid such as pFG173lox, sequences are rescued into the right end of the viral DNA, into E3 or into sites rightward of E3. The most important applications of this latter technology will likely be rescue of mutations into the fiber gene located immediately rightward of E3 (FIG. 9A) (fiber is important because it is a major ligand for binding to cellular receptors) but one can also rescue mutations, deletions, insertions and other modifications in E4 genes (located between fiber and the right ITR) or the method is used to rescue inserts of foreign DNA into E3 (cotransfection of a plasmid such as that depicted in FIG. 11 with pFG173lox). Note that the plasmid pFG173lox has a deletion of fiber, but E4 sequences could just as well be deleted as well as or instead of fiber. Note also that lox sites could be inserted at other locations in the Ad genome to enable the rescue of mutations engineered in other viral genes besides those of fiber or E4, or rescue of DNA inserts into other sites.

In a further embodiment of this invention, DNA-TP complexes are utilized to combine the high efficiency of head-to-head ITR mediated recombination, with or without site-specific recombination, such as Cre-lox recombination, with the high infectivity of DNA-TP. While the rescue of infectious virus via head-to-head ITR mediated homologous recombination, or head-to-head ITR mediated recombination with Cre-mediated recombination is surprisingly efficient compared to homologous recombination alone, and is more than adequate to produce viral vectors and to introduce mutations into the viral genome for most applications, there may be certain applications for which even higher efficiencies are desirable or necessary. It is known by those skilled in the art that the infectivity of adenovirus DNA is up to 100 fold higher if the virion DNA is extracted and purified by methods that leave intact the terminal protein (TP) that is normally linked to the 5' end of each strand of the duplex Ad DNA molecule (Sharp P A, Moore C, Haverty J L, "The infectivity of adenovirus 5 DNA-protein complex," Virology December 1976;75(2):442–456, Chinnadurai G, Chinnadurai S, Green M, "Enhanced infectivity of adenovirus type 2 DNA and a DNA-protein complex." J Virol April 1978; 26(1):195–199). For rescue of cassettes, the two plasmid system is more than sufficiently efficient, especially with the approximately 10-fold enhancement in efficiency demonstrated herein for head-to-head ITR mediated recombination, or the approximately 100-fold enhancement in efficiency demonstrated herein for head-to-head ITR mediated recombination when coupled with Cre-lox mediated recombination (over homologous recombination alone), and consequently would be preferred for most purposes. However, there may be times when even higher efficiencies are required, as when, for example, one wishes to develop a library of fiber mutations (a large number of different viruses—the more the better). Then the chore of preparing DNA-TP might be worthwhile and could be accomplished by those skilled in the art. Thus, an aspect of the present invention includes the combination of the enhanced recombination mediated by head-to-head ITR junctions in shuttle plasmids, with or without Cre-lox recombination, with the high specific infectivity of adenoviral DNA-TP complexes.

Therefore, it is an object of the present invention to provide a highly efficient, reliable, and simple method for isolation of viral vectors in which rescue of viruses is enhanced by provision of head-to-head ITR junctions whether recombination is based on homologous recombination, or on site-specific recombination catalysed by a site-specific recombinase, such as but not limited to the Cre recombinase.

It is a further object of this invention to use head-to-head ITR constructs, with or without Cre-lox-mediated recombination, and known two plasmid vector production systems to provide a simple method for introducing mutations or other modifications of viral genes into any desired location in the viral genome.

It is a further object of this invention to provide a simple and useful system by which adenovirus cloning vectors may be developed.

It is a further object of this invention to provide a kit for efficient production of adenoviral vectors for vaccine and gene-therapeutic applications which relies on homologous or site-specific recombination, and which does not require a cold-chain for distribution.

A further object of this invention is to provide a system whereby the high-efficiency of the head-to-head ITR mediated recombination, with or without Cre-lox mediated recombination, is combined with enhanced infectivity achieved when adenovirus-TP complexes are utilized.

Further objects of this invention will become apparent from a review of the complete disclosure and the claims appended hereto.

BRIEF DESCRIPTION OF DRAWINGS

FIGS. 4B-1 and 4B-2 illustrates the construction of a plasmid, pBHGdX1Plox, containing a modified E3 deletion (taken from pFG23dX1) and a lox site 5' of the pIX gene. The plasmid pFG23dX1P was constructed by inserting an oligonucleotide containing a PacI site (SEQ ID NO:9; AB14566; 5'-CTAGCTTAATTAAG-3'; this oligo self anneals to produce a double stranded DNA with 5' overhangs that hybridize to overhangs generated by XbaI cleavage) into the AbaI site of pFG23dX1. The resulting plasmid, pFG23dX1P, is identical to pFG23dX1 except that the unique XbaI site at nt 11392 is changed to a unique Pac I site. The plasmid pNG17 was constructed by cloning the 6724 bp SpeI/ClaI fragment from pBHGloxΔE1,3 into pBluescript. The plasmid pNG17dX1P was constructed by replacing the 1354 bp SpeI/NdeI fragment from pNG17 with the 2143 bp SpeI/NdeI fragment from pFG23dX1P. Finally, the plasmid pBHGdX1Plox was constructed by replacing the 6724 bp SpeI/ClaI fragment from pBHGloxΔE1,3 with the 7513 bp SpeI/ClaI fragment from pNG 17dX1P. pBHGdX1Plox thus contains a modified E3 region such that the deletion of E3 sequences is that of the parental plasmid pFG23dX1 (a deletion of 1878 bp) rather than the larger deletion of the other parental plasmid pBHGloxΔE1,3.

According to this invention, the ITR of the shuttle plasmid is replaced with a head-to-head ITR junction, thereby enhancing the efficiency of the site-specific recombination method. Thus a shuttle plasmid such as pCA35loxΔCreITR of FIG. 8D is also suitable for generation of an adenovirus vector.

Figure 8A:
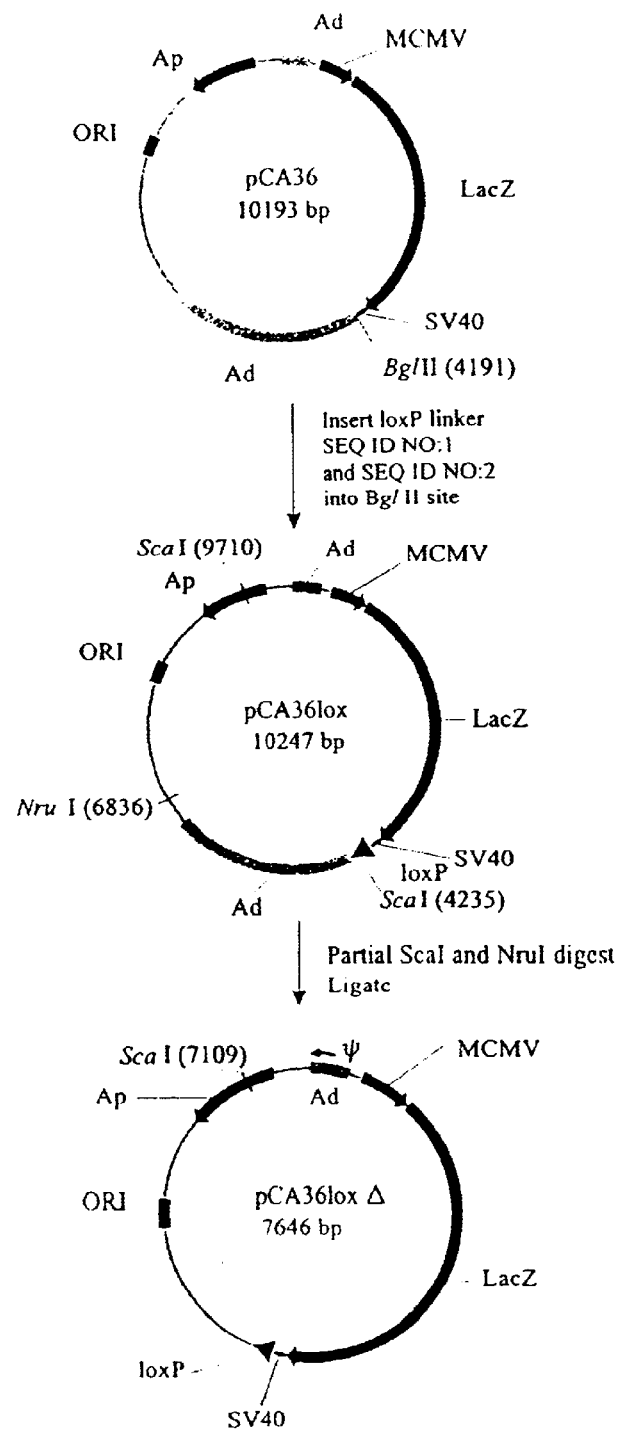
FIG. 8A is a diagrammatic representation of a method for constructing pCA36loxΔ a shuttle plasmid containing the leftmost approximately 340 nt of Ad5, an expression cassette encoding β-galactosidase, and a lox P site for rescue of the LacZ gene into adenovirus vectors. A synthetic loxP site (SEQ ID NO:1 and SEQ ID NO:2; AB3233/3234) was introduced into the BglII site of pCA36 resulting in pCA36lox. This plasmid was then digested with Nru I and partially digested with Sca I, a 7646 bp fragment was gel purified and self ligated yielding pCA36loxΔ.
Figure 8B:
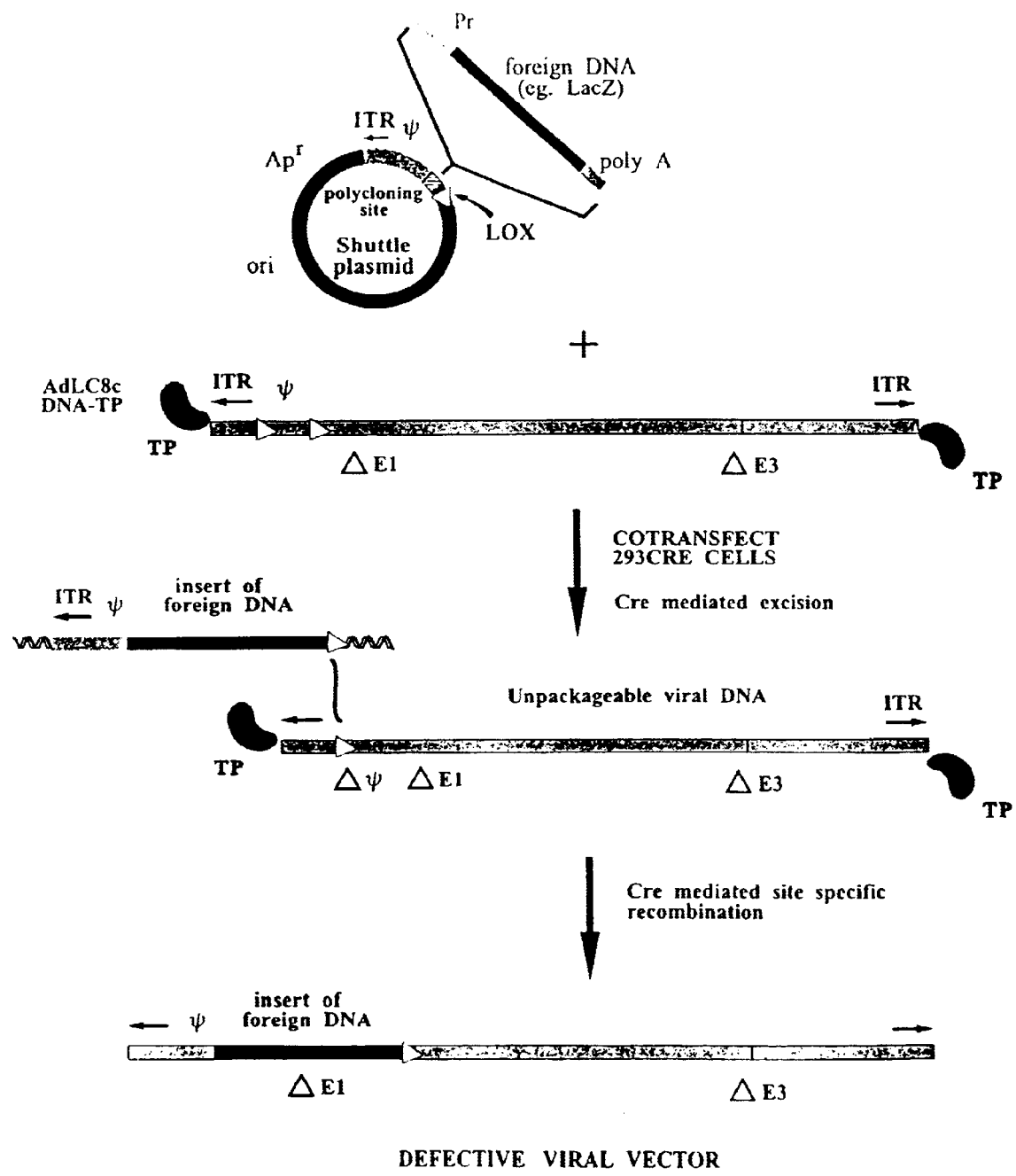
FIG. 8B is a diagrammatic representation of a means to isolate adenoviral vectors containing an expression cassette by cotransfection of 293Cre cells with (a) AdLC8c DNA-TP complex having covalently bound terminal protein (TP) linked to the 5' ends of Adenoviral DNA and (b) a shuttle plasmid containing an expression cassette and a lox P site. Cre-mediated excision of the floxed packaging signal of AdLC8c renders the AdLC8c genome defective for packaging. A second Cre-mediated recombination event between the lox sites in the shuttle plasmid and the AdLC8c genome results in a vector with a packaging signal, the foreign DNA insert, and a single lox site. According to this invention, the ITR of the shuttle plasmid is replaced with a head-to-head ITR junction, thereby enhancing the efficiency of the site-specific recombination method.
Figure 8C:
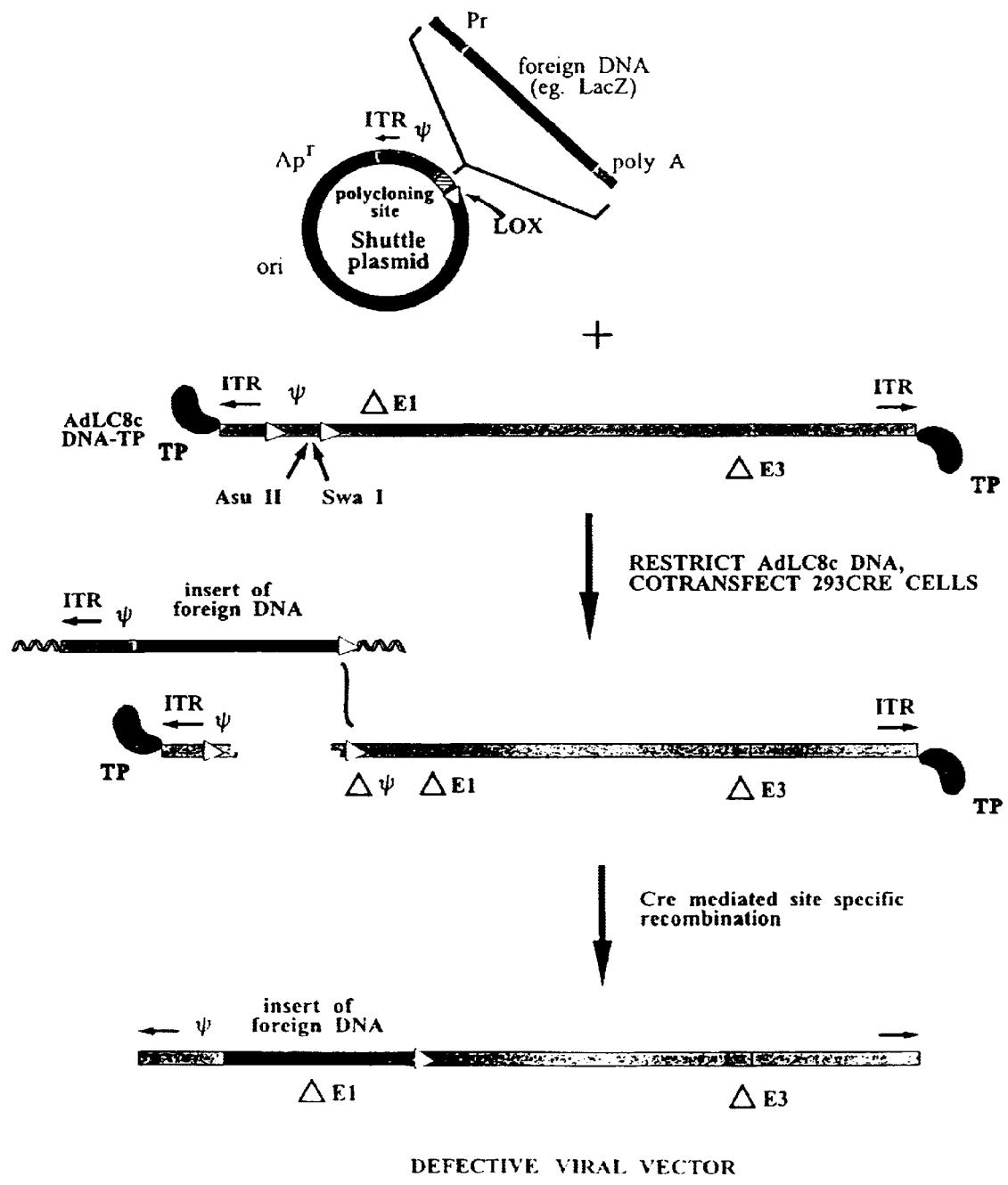
FIG. 8C is a diagrammatic representation of a means to isolate adenoviral vectors containing an expression cassette by cotransfection of 293Cre cells with restricted AdLC8c DNA-TP and a shuttle plasmid containing an expression cassette and a lox P site. AdLC8c DNA-TP is cleaved with an endonuclease such as Asu II or Swa I that recognize unique restriction enzyme sites between the lox sites flanking ψ. Cleavage of viral DNA with restriction enzymes prior to cotransfection reduces the infectivity of parental virus DNA and when combined with the high-efficiency of Cre-mediated recombination results in high-efficiency of vector isolation in cotransfected 293Cre cells as illustrated. Rejoining of parental DNA fragments and generation of infectious parental virus rather than the desired vector is avoided because of the action of Cre on the floxed packaging signal in AdLC8c. However, when the viral DNA-TP complex is cut with a restriction enzyme as illustrated, the level of Cre-mediated recombination is sufficiently high that most, if not all, progeny viruses result from recombination between the shuttle plasmid and the large DNA-TP fragment. Therefore, the left-most lox site of AdLC8c and equivalent vectors is not essential. According to this invention, the ITR of the shuttle plasmid is replaced with a head-to-head ITR junction, thereby enhancing the efficiency of the site-specific recombination method.
Figure 8D:
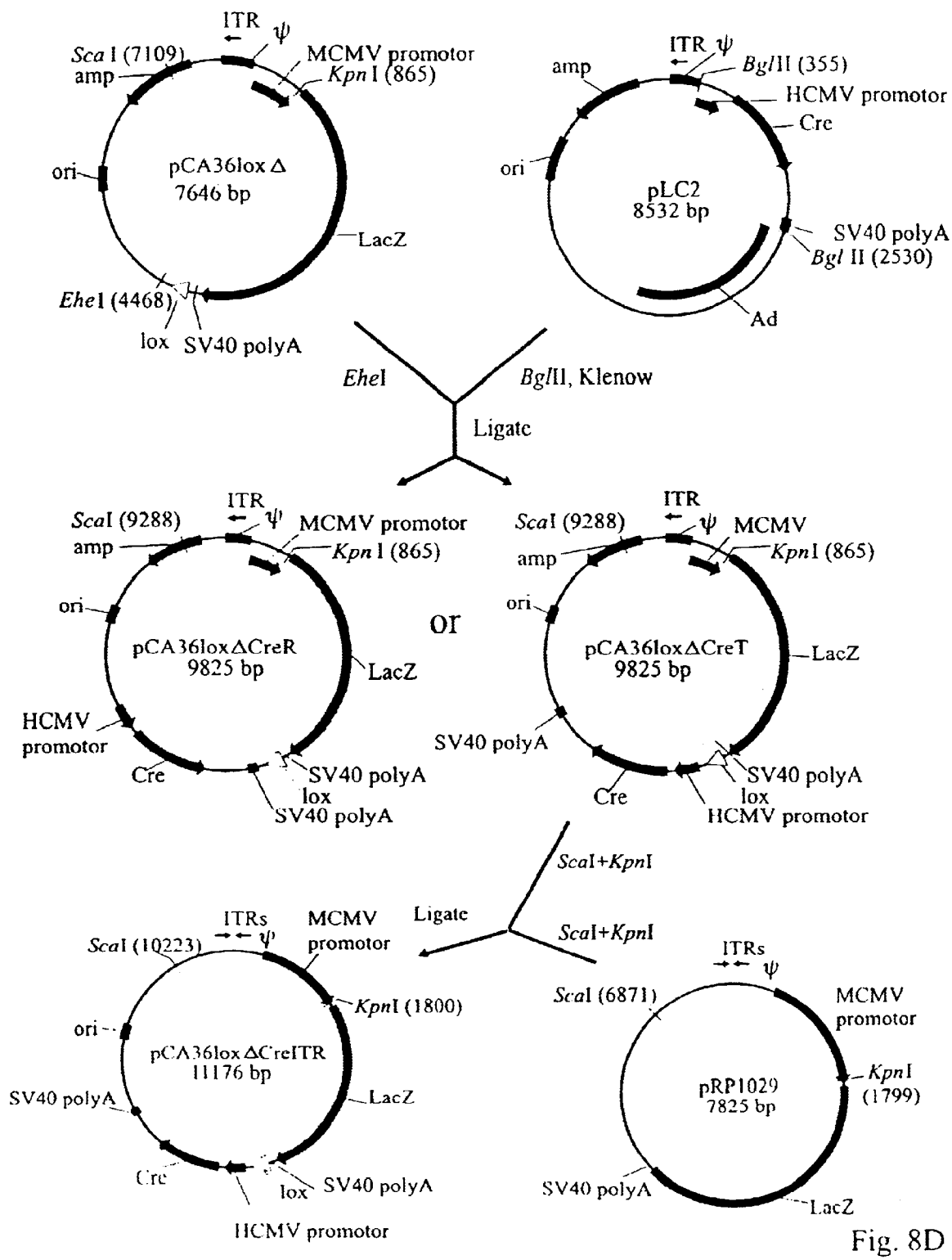
FIG. 8D is a diagrammatic representation of a method for constructing shuttle plasmids expressing Cre. The Cre expression cassette was obtained from the plasmid pLC2 (Chen, L., Anton, M. and Graham, F. L., "Production and characterization of human 293 cell lines expressing the site-specific recombinase Cre," Somat. Cell and Molec. Genet. 22:477–488, 1996), as a 2175 bp BglII fragment which was end-modified with Klenow DNA polymerase and inserted into the EheI site of pCA36loxΔ to generate pCA36loxΔCreR and pCA36loxΔCreT. The plasmid pCA35loxΔCreITR was constructed by replacing the 1402 bp ScaI/KpnI fragment in pCA36loxΔCreT with the 2753 bp ScaI/KpnI fragment from the plasmid pRP1029. Plasmid pCA35loxΔCreITR contains ITR junctions which are known to be functionally capable of generating replicating linear Ad DNA molecules (Graham, F. L., "Covalently closed circles of human adenovirus DNA are infections," The EMBO J. 3, 2917–2922, 1984).
Figure 8E:
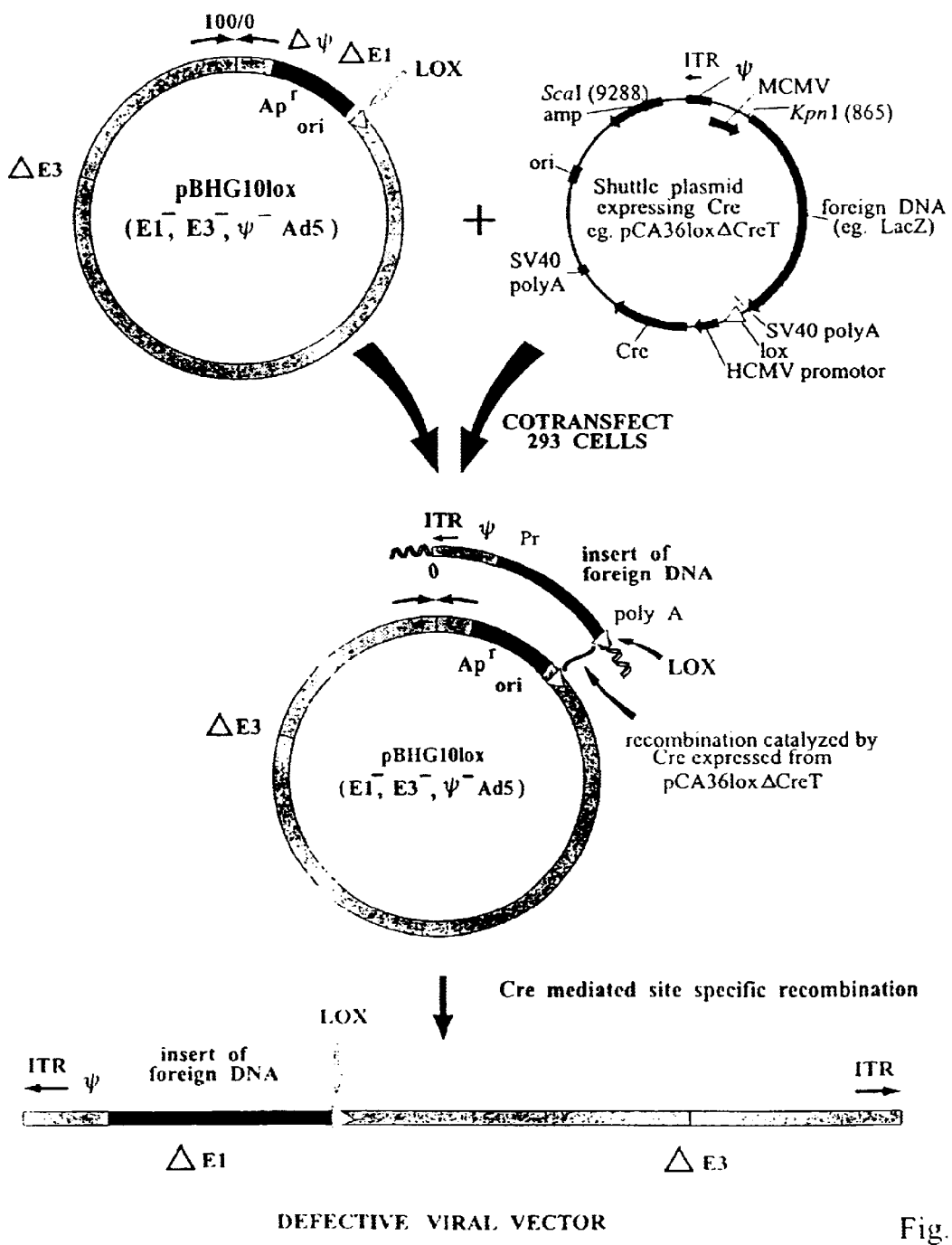
FIG. 8E provides a schematic representation of a cotransfection experiment wherein an Ad genomic plasmid bearing a lox site such as pBHGloxΔE1,3 and a "Lox" shuttle plasmid expressing Cre are introduced into 293 cells in order to generate Ad expression vectors, without having to use cells which stably express Cre. This technique is applicable to any cell type suitable for Ad vector generation, including but not limited to 293 cells, and PER-C6 cells (Fallaux et al., Hum. Gene Ther. Sep. 1, 1998;9(13):1909–17), 911 cells (Fallaux et al., Hum. Gene Ther. Jan. 20, 1996;7(2): 2.15–222). or other cells.
Figure 8F:
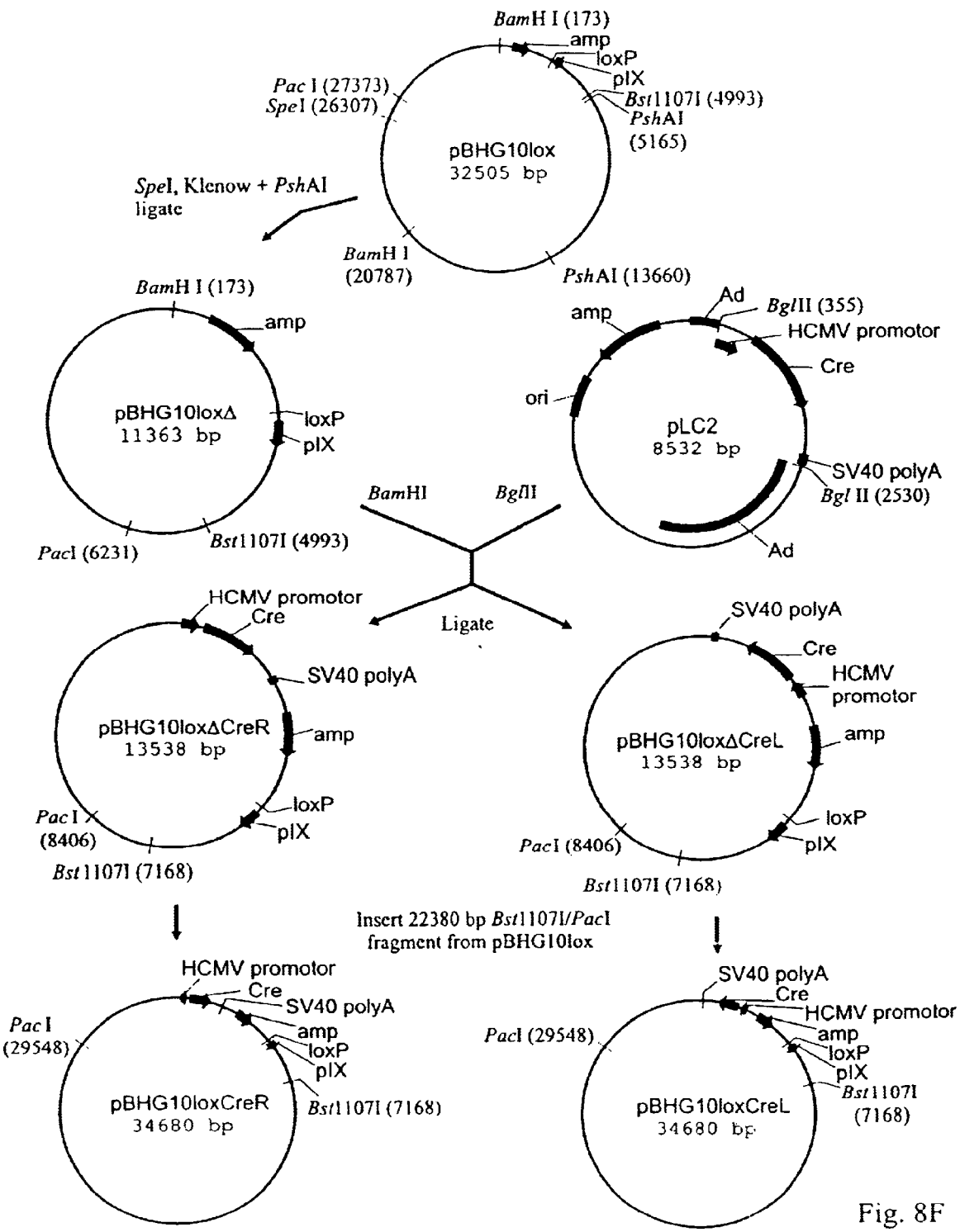

FIG. 8F. Demonstrates the construction of an Ad genomic plasmid encoding Cre. The plasmid pBHGloxΔ was constructed by collapsing pBHGloxΔE1,3 with SpeI and PshAI. The Cre expression cassette, taken from the plasmid pLC2 as a 2175 bp BglII fragment, was inserted into the BamHI site of pBHGloxΔto generate pBHGloxΔCreR and pBHGloxΔCreL. The 1238 bp Bst1107I/PacI fragment from pBHGloxΔCreR and pBHGloxΔCreL was replaced with the 22380 bp Bst1107I/PacI fragment from pBHGloxΔB1,3 to generate pBHGloxCreR and pBHGloxCreL, respectively.

Figure 9A:
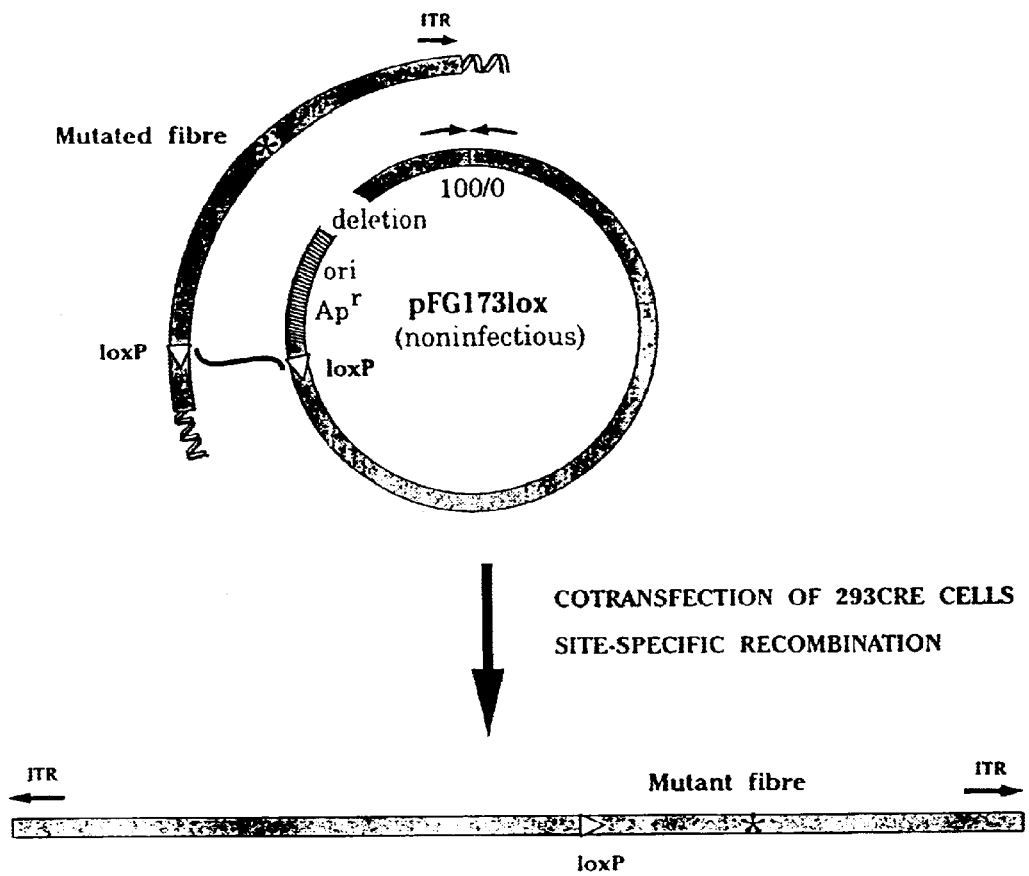

FIG. 9A is a diagrammatic representation of a method for rescuing fiber mutations into infectious virus using Cre-lox recombination. Plasmid pFG173 lox is derived from pFG173 which is a bacterial plasmid containing most of the Ad5 genome but from which sequences have been deleted (represented by "deletion" in the diagram) that render the plasmid noninfectious. The sequences are substituted with bacterial DNA containing an antibiotic resistance gene and a bacterial plasmid origin of DNA replication. A lox site upstream (leftward in the conventional map of the Ad genome) of the deletion/substitution is inserted in the plasmid for Cre-mediated recombination with a similar lox site in a shuttle plasmid containing the right region of the viral genome from approximately 85 mu to approximately 100 mu and including most or all of the right ITR. Recombination as illustrated generates an infectious virus containing sequences representing the left approximately 78 mu of the Ad genome derived from pFG173lox and sequences from approximately 85–100 mu derived from the shuttle plasmid. According to this invention, the ITR of the shuttle plasmid is replaced with a head-to-head ITR junction, thereby enhancing the efficiency of the site-specific recombination method.

Figure 9B:
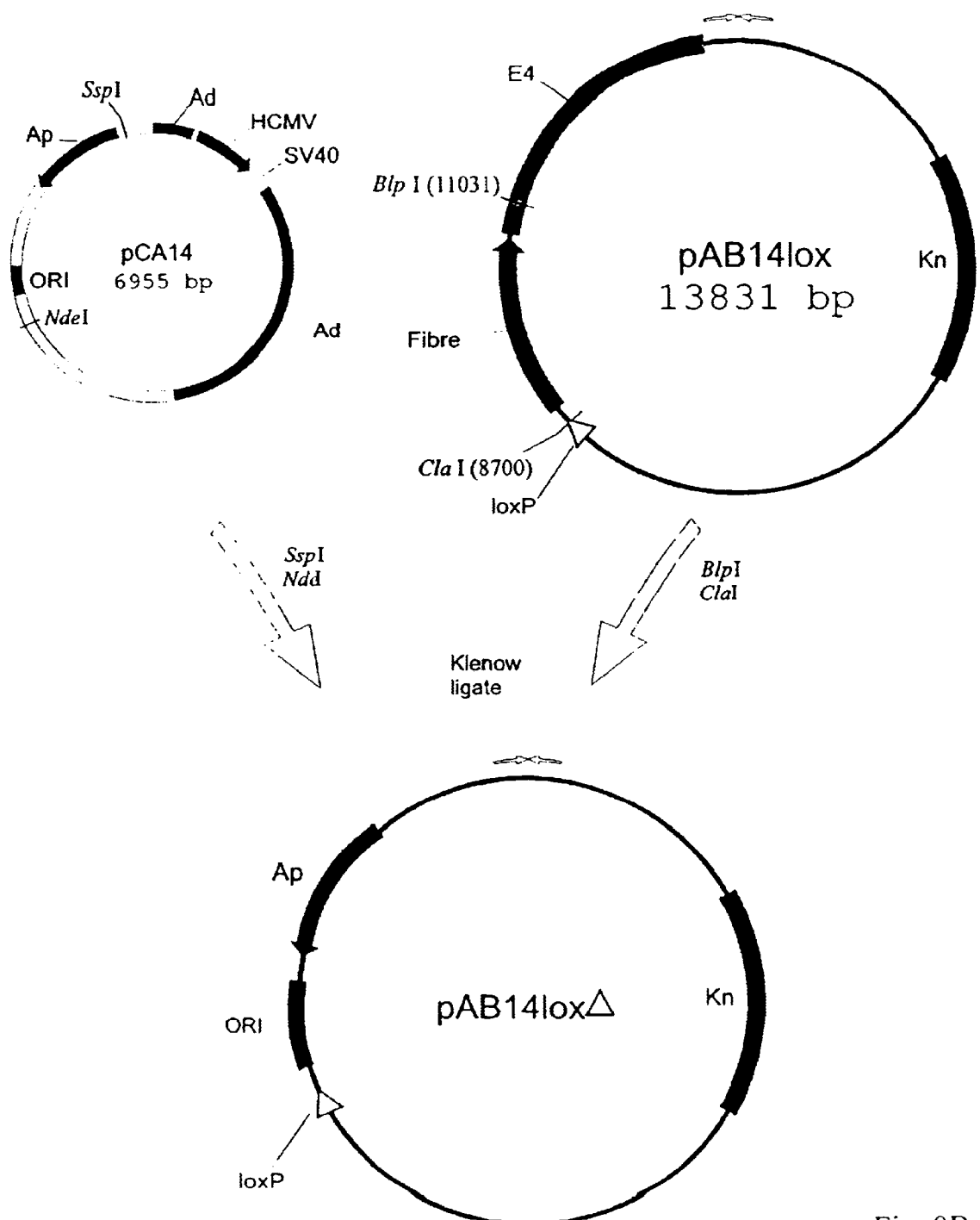

FIG. 9B is a diagrammatic representation of a method for constructing a plasmid containing a lox site and ampicillin resistance gene substituting for the fiber gene. Starting with pAB14lox whose construction is described in FIG. 14, the DNA sequences between the Cla I site and the Blp I site containing fiber are substituted with a DNA segment containing the ampicillin resistance gene and a plasmid origin of DNA replication. The NdeI to Ssp I DNA fragment from pCA14 (Microbix Biosystems) containing ampicillin resistance gene and plasmid origin of DNA replication is treated with Klenow DNA polymerase and ligated with a similarly treated Blp I to ClaI fragment of pAB14lox to generate the ampicillin and kanamycin doubly resistant, fiber gene deleted, pAB14loxΔ.

Figure 9C:
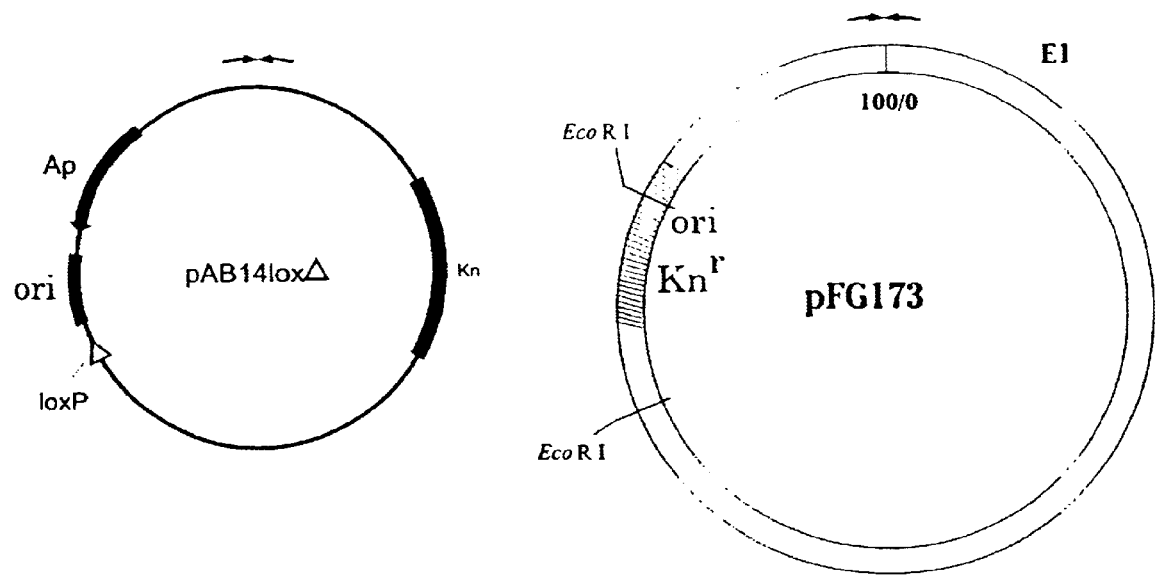
Figure 9C:
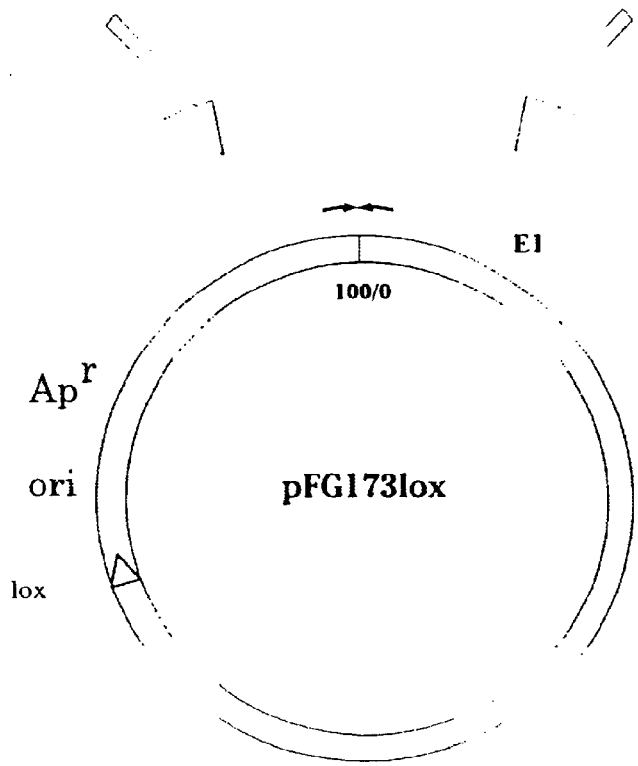

FIG. 9C is a diagrammatic representation of a method for combining the plasmid of FIG. 9B with pFG173 to produce pFG173lox for rescuing fiber or E4 mutations into infectious virus using Cre-lox recombination. The plasmid pAB14loxΔ is treated with restriction enzymes that cut in and around the kanamycin resistance gene and pFG173 is similarly digested with Eco RI as illustrated. Transformation of *E. coli* with the fragmented DNA from the two plasmids results in formation of a replicating plasmid in which the sequences in and around the shaded portion indicated in pFG173 are substituted with corresponding sequences from pAB14loxΔ by homologous recombination (Chartier C, Degryse E, Gantzer M, Dieterle A, Pavirani A, Mehtali M. Efficient generation of recombinant adenovirus vectors by homologous recombination in *Escherichia coli.* J Virol 1996 July;70(7): 4805–4810).

Figure 3:
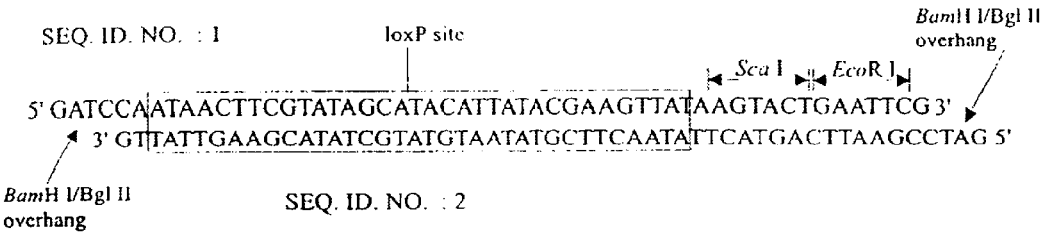
FIG. 3 illustrates four sets (pairs) of oligonucleotides used in various cloning procedures. The oligos are annealed prior to use to produce the double stranded DNA segments illustrated. Three of the oligonucleotide pairs contain loxP, the recognition site for Cre recombinase as well as one or more restriction endonuclease sites used for diagnostic purposes or for subsequent cloning steps. One of the oligonucleotide pairs contains several restriction endonuclease sites and was used to introduce a polycloning site into various shuttle plasmids.
Figure 3:
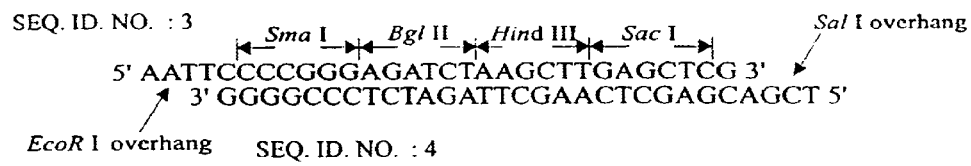
Figure 3:
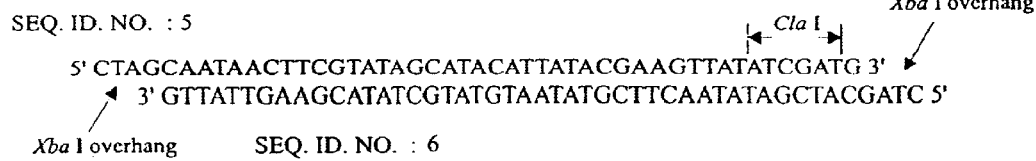
Figure 3:
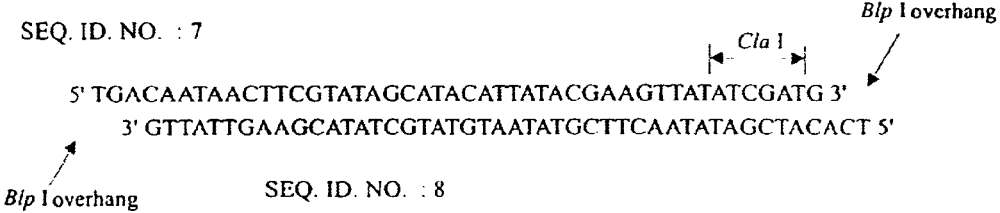
Figure 10:
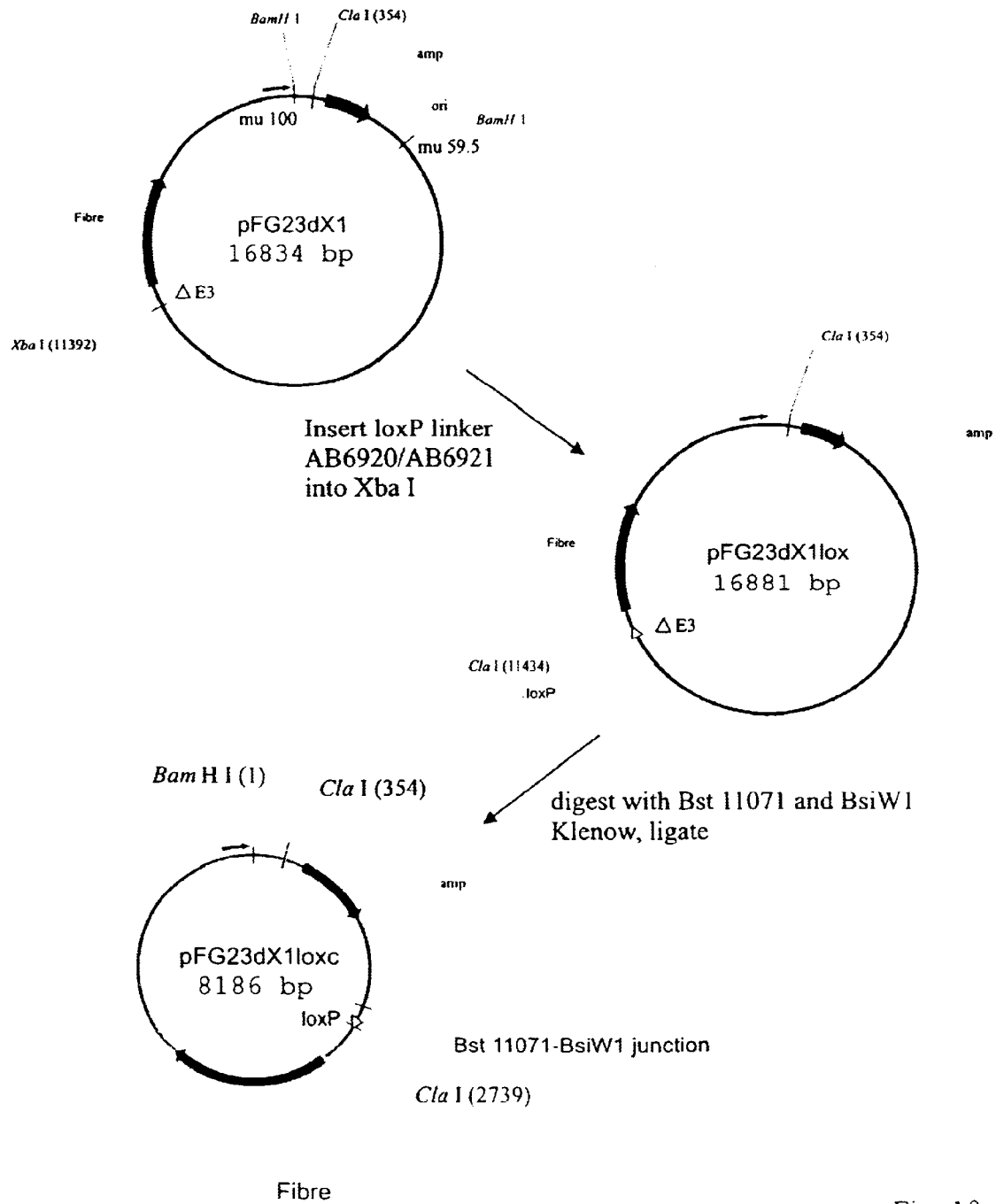

FIG. 10 is a diagrammatic representation of method for constructing a plasmid containing the right approximately 40% of the virus genome wherein a lox P site has been inserted near the 5' end of the fiber gene. The plasmid pFG23dX1 contains the right 40% of the Ad5 genome cloned into the bacterial plasmid pBR322, and has a deletion of an XbaI fragment from nt 28,589 (79.6 mu) of the wt Ad5 sequence to nt 30470 (mu 84.8) leaving a unique XbaI site suitable for insertion of a loxP site. A loxP site comprised of two synthetic oligonucleotides (SEQ ID NO:5 and SEQ ID NO:6;

AB6920/AB6921, FIG. 3) was ligated into the Xba I site of pFG23dX1 to generate pFG23dX1lox which contains a loxP site upstream of the sequences encoding fiber. Finally, pFG23dX1lox was further modified by deletion of viral sequences between a unique Bst1107I site and a BsiW1 site immediately 5' of the lox P site to generate pFG23dX1loxc.

Figure 11A:
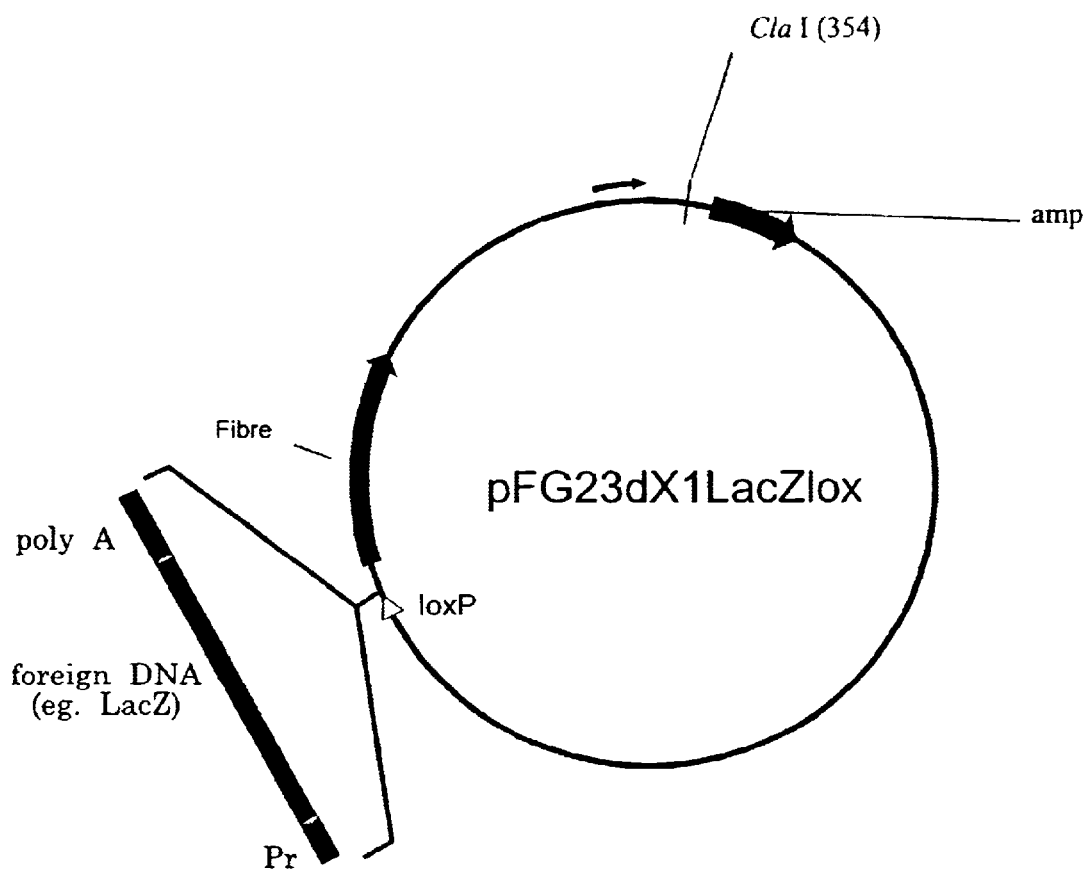

FIG. 11A illustrates a pFG23dX1lox plasmid with an expression cassette encoding bacterial β-galactosidase inserted into the Cla I site between the lox P site and the fiber gene.

Figure 11B:
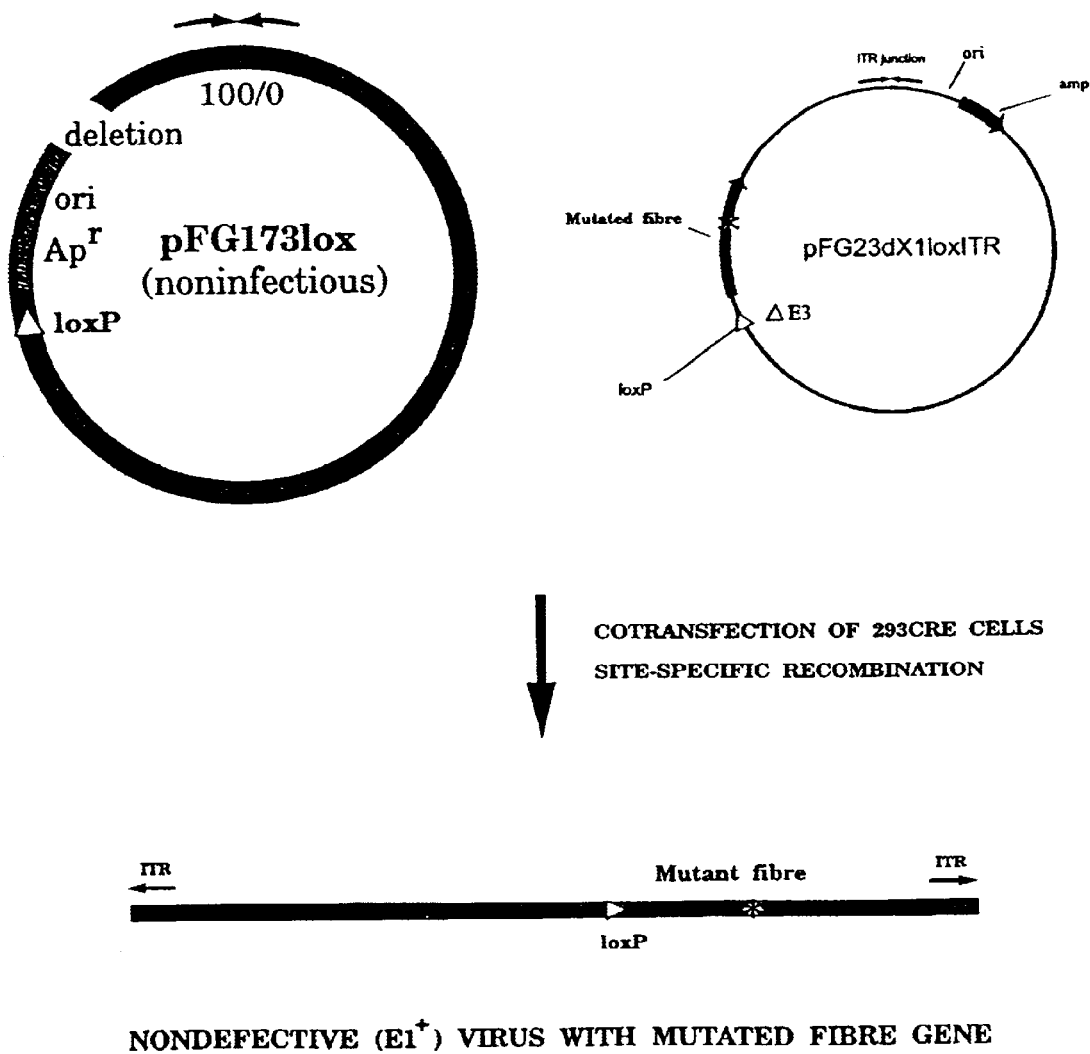

FIG. 11B is a diagrammatic representation of a method for combining two noninfectious plasmids by site specific recombination between lox sites inserted 5' of the Ad E3 region in each plasmid to generate a replicating packageable recombinant viral genome. Both plasmids comprise ITR junctions that allow for DNA replication in transfected host cells that express viral functions required in trans for Ad DNA replication. The combined plasmid DNAs encode all viral functions required in trans and in cis for viral DNA replication and packaging into virions. In the illustrated example, not meant to be limiting, the method is used for rescuing fiber mutations into infectious virus using Cre-lox recombination. Plasmid pFG173lox is derived from pFG173 which is a bacterial plasmid containing most of the Ad5 genome but from which sequences have been deleted (represented by "deletion" in the diagram) that render the plasmid noninfectious. The sequences are substituted with bacterial DNA containing an antibiotic resistance gene and a bacterial plasmid origin of DNA replication. Said sequences could be additionally substituted with an expression cassette encoding Cre recombinase. A lox site upstream (leftward in the conventional map of the Ad genome) of the deletion/substitution is inserted in the plasmid for Cre-mediated recombination with a similar lox site in a shuttle plasmid containing the right region of the viral genome from approximately 85 mu to approximately 100 mu and including the right ITR joined "head to head" with the right ITR. Linearization of the two plasmids DNAs and site specific recombination between the lox sites will generate an infectious virus containing sequences representing the left approximately 78 mu of the Ad genome derived from pFG173lox and sequences from approximately 85–100 mu derived from the shuttle plasmid.

Figure 12:
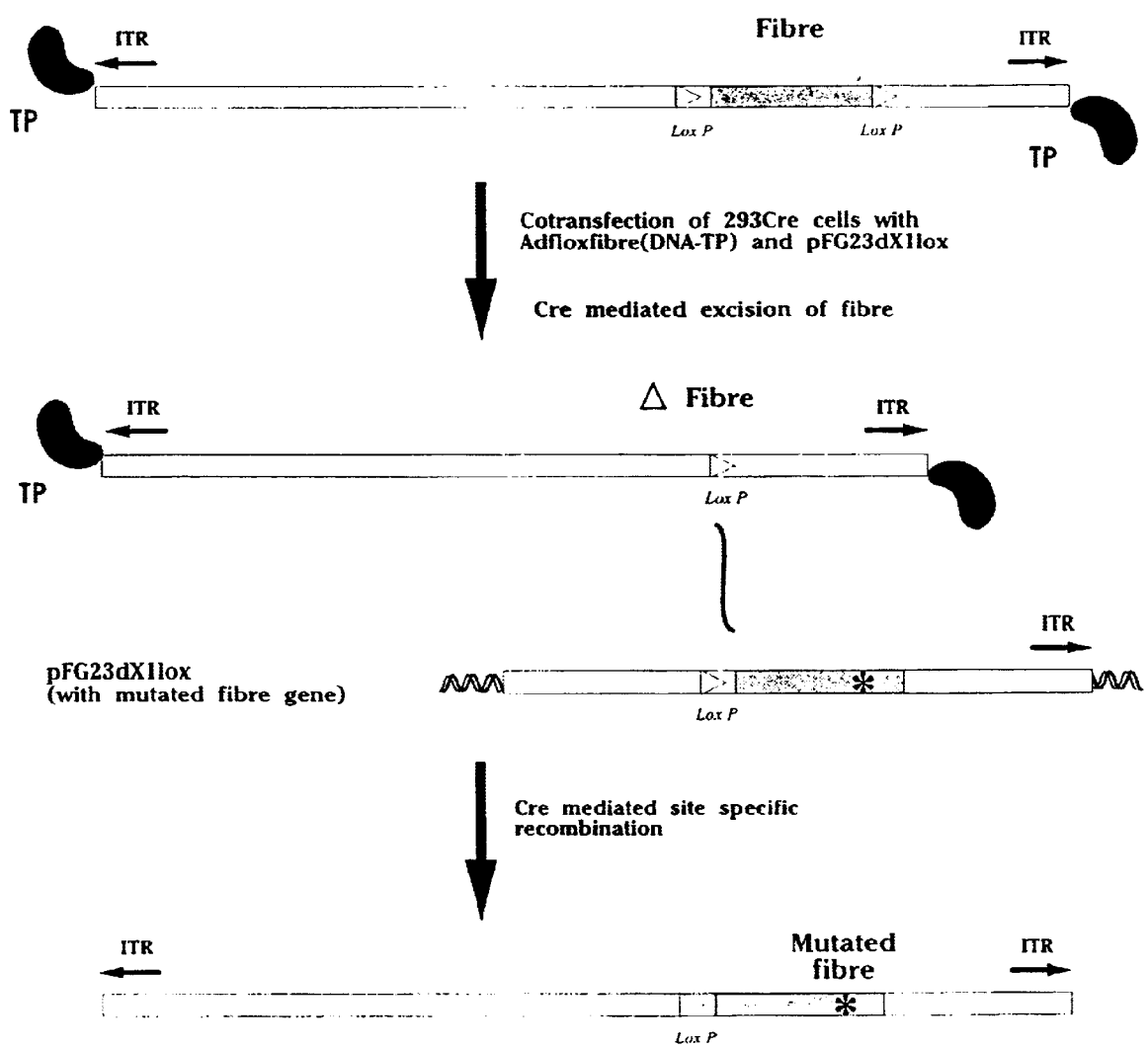

FIG. 12 is a diagrammatic representation showing rescue of a fiber mutation into a virus genome by cotransfection of 293 Cre cells with DNA-TP of an Adfloxed fiber and a plasmid containing a lox P site 5' of a (optionally mutated) fiber gene. Viral DNA-TP complex extracted from virus preparations of Adfloxfiber (FIG. 15) and plasmid DNA (pFGdX1lox) optionally carrying a mutated fiber gene are cotransfected into 293Cre cells to produce a recombinant virus expressing the optionally mutated fiber. If desired, viral DNA can be prepared so that the terminal protein remains linked to the ends of the virion DNA as indicated.

As will be seen from the present disclosure, a shuttle plasmid with a head-to-head ITR junction will provide for enhanced efficiency of virus rescue.

Figure 13:
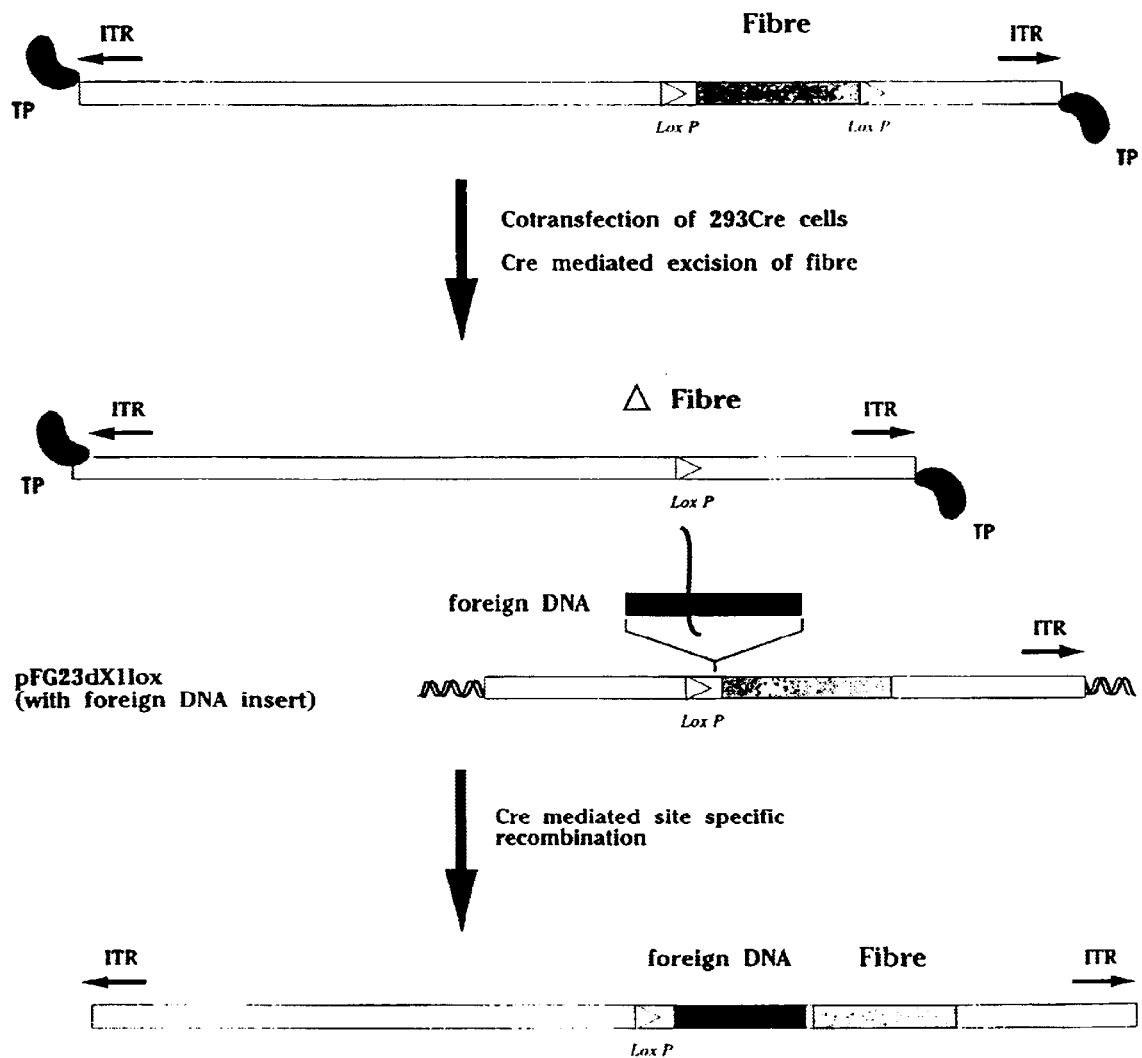

FIG. 13 is a diagrammatic representation showing rescue of a foreign DNA sequence into a virus genome by cotransfection of 293Cre cells with DNA-TP of an Adfloxed fiber and a plasmid containing a lox P site, and a foreign DNA inserted 5' of the fiber gene. Cotransfection of cells with Adfloxfiber DNA-TP and pFG23dX1LacZlox results in production of a vector carrying the foreign (e.g. lacZ) gene inserted upstream of fiber. As noted above in the description of FIG. 8C, the right-most lox site depicted in the Adfloxed fiber genome can be omitted if the DNA-TP is digested with one or more restriction enzymes which cut rightward of the lox site located 5' of fiber. As will be seen from the present disclosure, a shuttle plasmid with a head-to-head ITR junction will provide for enhanced efficiency of virus rescue.

Figure 14:
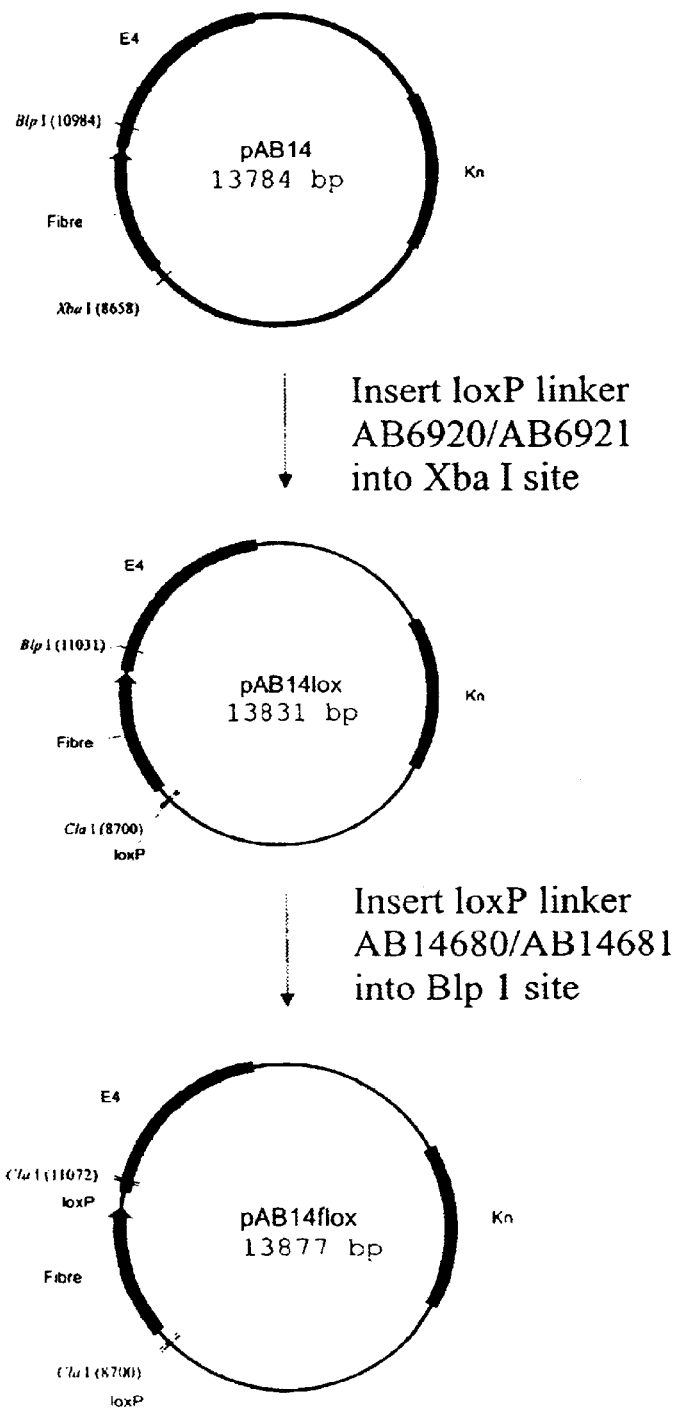

FIG. 14 is a diagrammatic representation showing construction of a plasmid containing a fiber gene with flanking lox P sites. Plasmid pAB14 (described in: Bett, A. J., Prevec, L., and Graham, F. L. Packaging capacity and stability of human adenovirus type 5 vectors. J. Virol. 67: 5911–5921, 1993.) contains Ad sequences from approximately mu 0 to 1.0, 10.6 to 16.1, 69.0 to 78.3, and 85.8 to 100. The plasmid has unique XbaI and BlpI restriction sites suitable for insertion of synthetic oligonucleotides containing lox P sites as illustrated. PAB 14flox was constructed by first inserting a lox site into the XbaI site that is upstream of fiber to produce pAB14lox. Subsequently a second lox site was inserted into the unique Blp I site in pAB14 which is located between the 3' terminus of the fiber gene and the coding regions of E4 genes (pAB14flox: fiber flanked by lox sites).

Figure 15:
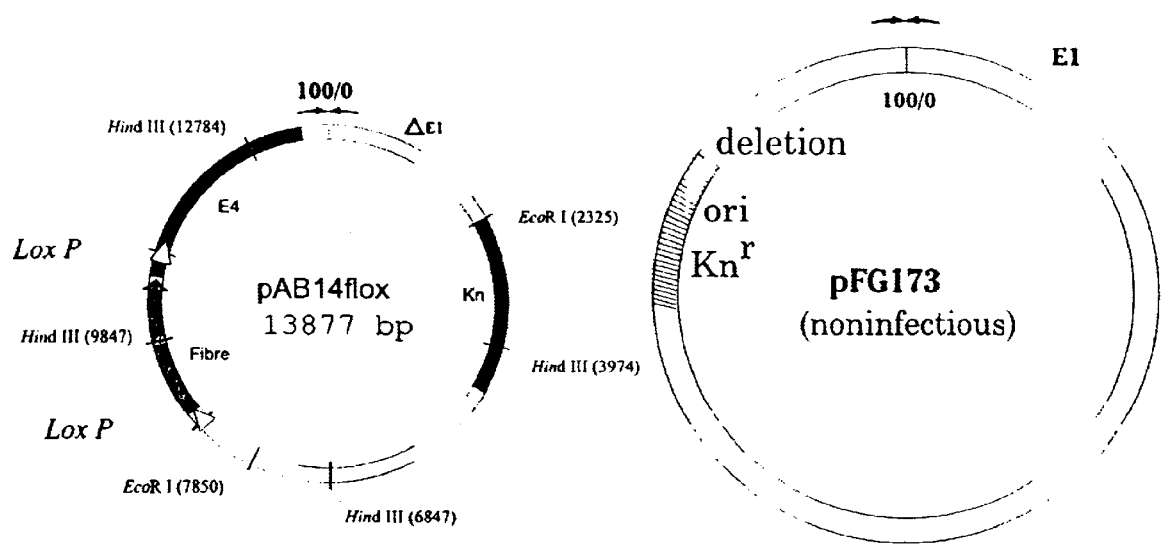
Figure 15:
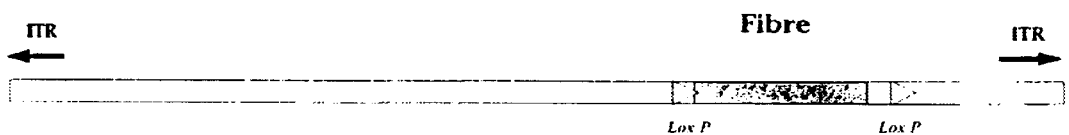

FIG. 15 is a diagrammatic representation showing isolation of a virus genome containing lox P sites flanking the fiber gene (floxed fiber). Cotransfection of pAB14flox with pFG173 (described in Hanke, T., Graham, F. L., V. Lulitanond and D. C. Johnson. Herpes simplex virus IgG Fc receptors induced using recombinant adenovirus vectors expressing glycoproteins E and I. Virology 177: 437–444, 1990. PFG173 is available from Microbix Biosystems) generates a virus containing a floxed fiber gene, Adfloxfiber.

DETAILED DESCRIPTION OF THE PREFERRED EMBODIMENTS

One embodiment of the present invention provides a bacterial plasmid comprising an antibiotic resistance gene and origin of replication for replication of said plasmid in host cells and further comprising a circularized modified human adenovirus genome that optionally contains sequences that can be recognized and acted upon by the site-specific recombinase such as Cre, FLP or like recombinases. Said bacterial plasmid is designed to be unable to generate infectious adenovirus by virtue of a deletion of viral DNA sequences, such as the packaging signal, which is normally located at the left end of wild-type Ad DNA, and which is essential for virus replication. Alternatively, formation of infectious virus may be prevented by the insertion of DNA ("stuffer DNA") such that the overall size of the resulting virus DNA exceeds the upper packaging limit for Ad virions (approximately 38 kb). Deletion of the pIX sequences from the Ad sequences makes the size-limitation of the packaging limitation more stringent, unless complementing cells which express the pIX gene product are used. Optionally, certain additional viral DNA sequences may be deleted, such as sequences from E3, which can in any event be omitted from the viral genome without preventing a viral genome from replicating in such cells as may be permissive for replication of said viral genome in the form of infectious virus.

Another embodiment of the invention provides a second bacterial plasmid, known as a "shuttle" plasmid, comprising minimally approximately 340 base pairs from the left end of the Ad5 genome, a head-to-head terminal repeat sequence (referred to in abbreviated form herein as "hthITR"), and the packaging signal sequences thereof, optionally a promoter, optionally a foreign DNA encoding a protein, optionally a polyadenylation signal, and optionally a lox site (various lox sites are known in the art, including, but not limited to, loxP, lox511, lox514, loxPsym, and mention of any one of these sites incorporates the mention of the other lox sites), or like site-specific recombinase recognition sites, such as FRT, recognized by the FLP recombinase. The promoter, foreign gene and poly adenylation signal are referred to herein collectively as an "expression cassette". Cotransfecting 293Cre cells with said shuttle plasmid and the plasmid of the first embodiment of the invention results in recombination between said plasmids and rescue of said expression cassette into an infectious viral vector by homologous recombination or by action of said Cre recombinase. The hthITR present in the shuttle plasmid has, surprisingly, been found to significantly enhance the level or recombination and rescue of recombinant virus, whether through homologous recombination or through site-specific, recombinase directed recombination, or both.

It will be appreciated that the term "bacterial plasmid" is not meant to be limiting, since one skilled in the art would recognize that other types of DNA could be recombined with equal efficiency, by homologous or site-specific recombination, such as through use of the Cre recombinase. For example, the Cre recombinase could be expressed in yeast cells to allow for high-efficiency recombination between yeast artificial chromosomes (YAC's) harboring an Ad genome, or, similarly, in bacteria, to allow for Cre-mediated recombination between cosmids or bacteriophage genomes harboring Ad sequences. Similarly, expression of Cre in mammalian cells could be used to allow for efficient recombination between two or more infectious Ad vectors, between an Ad vector and a bacterial plasmid, between an adenoviral genome and a linear DNA fragment and the like.

A third embodiment of the invention provides a mammalian cell line, such as a human cell line, that provides the Cre recombinase enzyme. Alternatively, Cre may be provided by an Ad5 derived vector that expresses the Cre protein in suitable cells or Cre may be provided by a third plasmid encoding Cre or optionally Cre could be expressed from an expression cassette inserted into one of the two plasmids including a shuttle plasmid comprising said hthITR for use in the two plasmid rescue system. Alternatively, Cre could be expressed in other species, for example bacteria or yeast, to allow for recombination and generation of recombinant Ad genomes in said species. Alternatively, Cre could be provided as a pure or crude protein extract from expression in a variety of species for recombination of said bacterial plasmids in vitro. One skilled in the art would recognize that other recombinase systems are available which could catalyse similar recombination events in place of Cre, for example, not meant to be limiting, the yeast FLP recombinase recognizes and recombines FRT target sites and is therefore expected to provide functions similar to those described herein with reference to Cre and its loxP target sites.

A fourth embodiment of the invention provides an adenovirus or a plasmid containing adenovirus DNA wherein a segment of the viral DNA such as, but not limited to, the region encoding fiber is flanked by lox P sites.

A fifth embodiment of the invention provides an adenovirus or a plasmid containing adenovirus DNA wherein a segment of the viral DNA such as, but not limited to, the region encoding fiber is deleted and substituted by a lox P site.

A sixth embodiment of the invention provides a plasmid containing a portion of the viral genome including a segment of viral DNA comprising, for example, fiber coding sequences wherein a single lox P site is embedded upstream of fiber coding sequences such that Cre-mediated recombination between said plasmid DNA and the plasmid of the fifth embodiment results in production of an infectious viral genome. Optionally the fiber gene in said plasmid may be modified by mutation, insertion or deletion of portions of the fiber coding sequences. Similar plasmids can be constructed that have lox P sites at other locations, depending on the viral DNA segment that is to be manipulated by site-specific recombination. For example, a site exists in the Ad genome between the coding sequences of fiber and the coding sequences of E4 that is suitable for insertion of DNA.

In this embodiment of the invention, the efficiency of recombination is enhanced several fold by inclusion of an hthITR junction in both of the recombining plasmids. In a seventh embodiment of the invention, plasmids containing adenovirus sequences and lox sites are recombined in the presence of Cre recombinase to generate novel adenovirus mutants containing modifications of the fiber gene or modifications of other viral genes. In this embodiment of the invention, the efficiency of recombination is enhanced through inclusion of a hthITR junction in both of the recombining plasmids.

In a preferred embodiment of the present invention, a system is described for the construction of novel Ad vectors, or alteration of existing Ad vectors, by the use of a site-specific recombinase wherein hthITR junctions are included to enhance the efficiency of Ad vector production.

In a further embodiment of the invention, an infectious viral DNA-TP complex is engineered to take advantage of recombinase-mediated site-specific recombination and the enhanced level of infectivity achieved through presence of the terminal protein.

It will be appreciated by those skilled in the art that the present invention disclosure provides significant advances over techniques known in the art for generation of adenoviral vectors. First, the efficiency by which recombinants are produced is enhanced through use of an hthITR junction in combination with homologous recombination or in combination with site-specific recombination, rather than relying exclusively on homologous recombination. This invention further advances the art in that it facilitates use of vectors which are themselves non-infectious and stable. Further, by use of the methods disclosed herein, rapid production of recombinant virus is facilitated wherein every virus produced is a recombinant virus, as opposed to known methods wherein a starting virus is used in a site-specific recombination wherein substantial levels of non-recombinant starting virus remain in the preparation which has to then be serially passaged to remove the contaminating starter virus. As a result of this enhanced efficiency, while it may in many instances be desirable to colony or plaque-purify the results of a given cotransfection, because all viruses produced according to this embodiment of the instant technique are recombinants, plaque purification is not absolutely required. Accordingly, the instant method provides the option of rapid production of recombinants and screening of products, in a "shot-gun" approach, which will provide significant labor and time savings to those skilled in the art.

In reviewing the detailed disclosure which follows, it should be borne in mind that any publications referenced herein are hereby incorporated by reference in this application in order to more fully describe the state of the art to which the present invention pertains.

It is important to an understanding of the present invention to note that all technical and scientific terms used herein, unless otherwise defined, are intended to have the same meaning as commonly understood by one of ordinary skill in the art. The techniques employed herein are also those that are known to one of ordinary skill in the art, unless stated otherwise.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

The terms used herein are not intended to be limiting of the invention. For example, the term "gene" includes cDNAs, RNA, or other polynucleotides that encode gene products. "Foreign gene" denotes a gene that has been obtained from an organism or cell type other than the organism or cell type in which it is expressed; it also refers to a gene from the same organism that has been translocated from its normal situs in the genome. In using the terms "nucleic acid", "RNA", "DNA", etc., we do not mean to limit the chemical structures that can be used in particular steps. For example, it is well known to those skilled in the art that RNA can generally be substituted for DNA, and as such, the use of the term "DNA" should be read to include this substitution. In addition, it is known that a variety of nucleic acid analogues and derivatives is also within the scope of the present invention. "Expression" of a gene or nucleic acid encompasses not only cellular gene expression, but also the transcription and translation of nucleic acid(s) in cloning systems and in any other context. The term "recombinase" encompasses enzymes that induce, mediate or facilitate recombination, and other nucleic acid modifying enzymes that cause, mediate or facilitate the rearrangement of a nucleic acid sequence, or the excision or insertion of a first nucleic acid sequence from or into a second nucleic acid sequence. The "target site" of a recombinase is the nucleic acid sequence or region that is recognized (e.g., specifically binds to) and/or acted upon (excised, cut or induced to recombine) by the recombinase. The term "gene product" refers primarily to proteins and polypeptides encoded by other nucleic acids (e.g., non-coding and regulatory RNAs such as tRNA, sRNPs). The term "regulation of expression" refers to events or molecules that increase or decrease the synthesis, degradation, availability or activity of a given gene product.

The present invention is also not limited to the use of the cell types and cell lines used herein. Cells from different tissues (breast epithelium, colon, lymphocytes, etc.) or different species (human, mouse, etc.) are also useful in the present invention.

It is important in this invention to detect the generation and expression of recombinant nucleic acids and their encoded gene products. The detection methods used herein include, for example, cloning and sequencing, ligation of oligonucleotides, use of the polymerase chain reaction and variations thereof (e.g., a PCR that uses 7-deaza GTP), use of single nucleotide primer-guided extension assays, hybridization techniques using target-specific oligonucleotides that can be shown to preferentially bind to complementary sequences under given stringency conditions, and sandwich hybridization methods.

Sequencing may be carried out with commercially available automated sequencers utilizing labeled primers or terminators, or using sequencing gel-based methods. Sequence analysis is also carried out by methods based on ligation of oligonucleotide sequences which anneal immediately adjacent to each other on a target DNA or RNA molecule (Wu and Wallace, *Genomics* 4:560–569 (1989); Landren et al., *Proc. Natl. Acad. Sci.* 87:8923–8927 (1990); Barany, F., *Proc. Natl. Acad. Sci.* 88: 189–193 (1991)). Ligase-mediated covalent attachment occurs only when the oligonucleotides are correctly base-paired. The Ligase Chain Reaction (LCR), which utilizes the thermostable Taq ligase for target amplification, is particularly useful for interrogating late onset diabetes mutation loci. The elevated reaction temperatures permits the ligation reaction to be conducted with high stringency (Barany, F., *PCR Methods and Applications* 1: 5–16 (1991)).

The hybridization reactions may be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

The detection oligonucleotide probes range in size between 10–1,000 bases. In order to obtain the required target discrimination using the detection oligonucleotide probes, the hybridization reactions are generally run between 20°–60° C., and most preferably between 30°–50° C. As known to those skilled in the art, optimal discrimination between perfect and mismatched duplexes is obtained by manipulating the temperature and/or salt concentrations or inclusion of formamide in the stringency washes.

The cloning and expression vectors described herein are introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by reference. See, also, Ausubel et al., *Current Protocols in Molecular Biology*, John Wiley and Sons, Baltimore, Md. (1989); Hitt et al, "Construction and propagation of human adenovirus vectors," in *Cell Biology: A Laboratory Handbook*, Ed. J. E. Celis., Academic Press. $2^{nd}$ Edition, Volume 1, pp: 500–512, 1998; Hitt et al, "Techniques for human adenovirus vector construction and characterization," in *Methods in Molecular Genetics*, Ed. K. W. Adolph, Academic Press, Orlando, Fla., Volume 7B, pp:12–30, 1995; Hitt, et al., "Construction and propagation of human adenovirus vectors," in *Cell Biology: A Laboratory Handbook*," Ed. J. E. Celis. Academic Press. pp:479–490, 1994, also hereby incorporated by reference. The methods include, for example, stable or transient transfection, lipofection, electroporation and infection with recombinant viral vectors.

The protein products of recombined and unrecombined coding sequences may be analyzed using immune techniques. For example, a protein, or a fragment thereof is injected into a host animal along with an adjuvant so as to generate an immune response. Immunoglobulins which bind the recombinant fragment are harvested as an antiserum, and are optionally further purified by affinity chromatography or other means. Additionally, spleen cells may be harvested from an immunized mouse host and fused to myeloma cells to produce a bank of antibody-secreting hybridoma cells. The bank of hybridomas is screened for clones that secrete immunoglobulins which bind to the variant polypeptides but poorly or not at all to wild-type polypeptides are selected, either by pre-absorption with wild-type proteins or by screening of hybridoma cell lines for specific idiotypes that bind the variant, but not wild-type, polypeptides.

Nucleic acid sequences capable of ultimately expressing the desired variant polypeptides are formed from a variety of different polynucleotides (genomic or cDNA, RNA, synthetic olignucleotides, etc.) as well as by a variety of different techniques.

The DNA sequences are expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors contain selection markers (e.g., markers based on tetracycline resistance or hygromycin resistance) to permit detection and/or selection of those cells transformed with the desired DNA sequences. Further details can be found in U.S. Pat. No. 4,704,362.

Polynucleotides encoding a variant polypeptide include sequences that facilitate transcription (expression sequences) and translation of the coding sequences such that the encoded polypeptide product is produced. Construction of such polynucleotides is well known in the art. For example, such polynucleotides include a promoter, a transcription termination site (polyadenylation site in eukaryotic expression hosts), a ribosome binding site, and, optionally, an enhancer for use in eukaryotic expression hosts, and optionally, sequences necessary for replication of a vector.

*E. Coli* is one prokaryotic host useful particularly for cloning DNA sequences of the present invention. Other microbial hosts suitable for use include bacilli, such as *Bacillus subtilus*, and other enterobacteriaceae, such as Salmonella, Serratia, and various Pseudomonas species. Expression vectors are made in these prokaryotic hosts which will typically contain expression control sequences compatible with the host cell (e.g., an origin of replication). In addition, any number of a variety of well-known promoters are used, such as the lactose promoter system, a tryptophan (Trp) promoter system, a beta-lactamase promoter system, or a promoter system from phage lambda. The promoters typically control expression, optionally with an operator sequence, and have ribosome binding site sequences, for example, for initiating and completing transcription and translation.

Other microbes, such as yeast, are used for expression. Saccharomyces is a suitable host, with suitable vectors having expression control sequences, such a promoters, including 3-phosphoglycerate kinase or other glycolytic enzymes, and an origin of replication, termination sequences, etc. as desired.

In addition to microorganisms, mammalian tissue cell culture is used to express and produce the polypeptides of the present invention. Eukaryotic cells are preferred, because a number of suitable host cell lines capable of secreting intact human proteins have been developed in the art, and include the CHO cell lines, various COS cell lines, HeLa cells, myeloma cell lines, Jurkat cells, and so forth. Expression vectors for these cells include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobin genes, SV40, Adenovirus, Bovine Papilloma Virus, Herpes Virus, and so forth. The vectors containing the DNA segments of interest (e.g., polypeptides encoding a variant polypeptide) are transferred into the host cell by well-known methods, which vary depending on the type of cellular host. For example, calcium chloride transfection is commonly utilized for prokaryotic cells, whereas calcium phosphate treatment or electroporation is useful for other cellular hosts.

The method lends itself readily to the formulation of test kits for use in diagnosis. Such a kit comprises a carrier compartmentalized to receive in close confinement one or more containers wherein a first container contains reagents useful in the localization of the labeled probes, such as enzyme substrates. Still other containers contain restriction enzymes, buffers etc., together with instructions for use.

The methods provided herein for production of recombinant Ad vectors are a significant improvement over and are significantly different from previously described methods that rely on homologous recombination catalysed by recombinases in host cells or that rely on in vitro ligation of viral DNA fragments to produce infectious viral DNA. For viral DNA replication and packaging of viral DNA into virion particles, only three regions of the viral DNA are known to be required in cis. These are the left inverted terminal repeat, or ITR, (bp 1 to approximately 103) the packaging signals (approximately 194 to 358 bp) (Hearing and Shenk, 1983, Cell 33: 695–703; Grable and Hearing 1992, J. Virol. 64: 2047–2056) and the right ITR. Among the regions of the viral genome that encode proteins that function in trans, two have been most important in the design and development of adenovirus vectors. These are early region 3 (E3) located between approximately 76 and 86 mu (mu=% distance from the left end of the conventionally oriented genome) and early region 1 (E1) located between approximately 1 and 11 mu. E3 sequences have long been known to be nonessential for virus replication in cultured cells and many viral vectors have deletions of E3 sequences so that the capacity of the resulting vector backbone for insertion of foreign DNA is thereby increased significantly over that allowable by the wild-type virus (Bett, A. J., Prevec, L., and Graham, F. L. Packaging capacity and stability of human adenovirus type 5 vectors. J. Virol. 67: 5911–5921, 1993.). E1 encodes essential functions. However, E1 can also be deleted, providing that the resulting virus is propagated in host cells, such as the 293 cell line, PER-C6 cells, 911 cells, and the like, which contain and express E1 genes and can complement the deficiency of E1(–) viruses.

Viruses with foreign DNA inserted in place of E1 sequences, and optionally also carrying deletions of E3 sequences are conventionally known as "first generation" adenovirus vectors. First generation vectors are of proven utility for many applications. They can be used as research tools for high-efficiency transfer and expression of foreign genes in mammalian cells derived from many tissues and from many species. First generation vectors can be used in development of recombinant viral vaccines when the vectors contain and express antigens derived from pathogenic organisms. The vectors can be used for gene therapy, because of their ability to efficiently transfer and express foreign genes in vivo, and due to their ability to transduce both replicating and nonreplicating cells in many different tissues. Adenovirus vectors are widely used in these applications.

There are many known ways to construct adenovirus vectors. As discussed above, one of the most commonly employed methods is the so called "two plasmid" technique. In that procedure, two noninfectious bacterial plasmids are constructed with the following properties: each plasmid alone is incapable of generating infectious virus. However, in combination, the plasmids potentially can generate infectious virus, provided the viral sequences contained therein are homologously recombined to constitute a complete infectious virus DNA. According to that method, typically one plasmid is large (approximately 30,000–35,000 nt) and contains most of the viral genome, save for some DNA segment (such as that comprising the packaging signal, or encoding an essential gene) whose deletion renders the plasmid incapable of producing infectious virus or said plasmid contains an insertion such that said viral genome would be too large to be packaged into virions. The second plasmid is typically smaller (e.g. 5000–10,000 nt), as small size aids in the manipulation of the plasmid DNA by recombinant DNA techniques. Said second plasmid contains viral DNA sequences that partially overlap with sequences present in the larger plasmid. Together with the viral sequences of the larger plasmid, the sequences of the second plasmid can potentially constitute an infectious viral DNA. Cotransfection of a host cell with the two plasmids produces an infectious virus as a result of homologous recombination between the overlapping viral DNA sequences common to the two plasmids. One particular system in general use by those skilled in the art is based on a series of large plasmids known as pBHG10, pBHG11 and pBHGE3 described by Bett, A. J., Haddara, W., Prevec, L. and Graham, F. L: "An efficient and flexible system for construction of adenovirus vectors with insertions or deletions in early regions 1 and 3," Proc. Natl. Acad. Sci. U.S. 91: 8802–8806, 1994 and in U.S. patent application Ser. No. 08/250,885, and published as WO95/00655 (hereby incorporated by reference). Those plasmids contain most of the viral genome and are capable of producing infectious virus but for the deletion of the packaging signal located at the left end of the wild-type viral genome. The second component of that system comprises a series of "shuttle" plasmids that contain the left approximately 340 nt of the Ad genome including the packaging signal, optionally a polycloning site, or optionally an expression cassette, followed by viral sequences from near the right end of E1 to approximately 15 mu or optionally to a point further rightward in the genome. The viral sequences rightward of E1 overlap with sequences in the pBHG plasmids and, via homologous recombination in cotransfected host cells, produce infectious virus. The resulting viruses contain the packaging signal derived from the shuttle plasmid, as well as any sequences, such as a foreign DNA inserted into the polycloning site or expression cassette located in the shuttle plasmid between the packaging signal and the overlap sequences. Because neither plasmid alone has the capability to produce replicating virus, infectious viral vector progeny can only arise as a result of recombination within the cotransfected host cell. However, as has been noted above, such homologous recombination processes can be inefficient, resulting in variable success in the isolation of vectors and occasional failure, particularly in the hands of those who are not specifically skilled in the art of virology, and more particularly, in the art of adenovirology.

Site-specific recombination catalysed by an efficient recombinase, such as the Cre or FLP recombinase, can be many fold more efficient than homologous recombination. This invention disclosure provides methods and nucleic acid constructs which significantly enhance the ease of production of viral vectors by the two plasmid method by enabling site-specific recombination between individual nucleic acids constructs, neither of which alone is able to replicate and produce infectious adenovirus. The methodology described herein furthermore utilizes Cre-loxP and other known recombination systems for efficient introduction of mutations of viral genes into the viral genome. Furthermore, the instant methodology is also applicable to insertion of foreign DNA sequences into various regions of the viral DNA, in addition to the E1 region classically used for that purpose. In additional embodiments of this invention, site-specific recombination is utilized in combination with infectious viral DNA having covalently bound terminal protein (DNA-TP complex), at either or both 5' strands of the DNA. Additional embodiments and applications of the site-specific recombination methodology will also become apparent based on the instant disclosure. In addition, as disclosed herein, we have unexpectedly found that inclusion of a head-to-head ITR junction in the shuttle plasmid significantly enhances the efficiency of recombination, whether through homologous recombination or site-specific recombination mechanisms.

Having generally described the purposes, advantages, applications and methodology of this invention, the following specific examples are provided to describe in a detailed fashion, various embodiments of this invention. However, it should be appreciated that the invention described herein is not limited to the specifics of the following examples, which are provided merely as a guide for those wishing to practice this invention. The scope of the invention is to be evaluated with reference to the complete disclosure and the claims appended hereto.

It should further be recognized that the following examples using the human adenovirus serotype 5 are not meant to be limiting. One skilled in the art would realize that similar plasmids, viruses and techniques could be utilized with a different human adenovirus serotype, for example Ad2. Similarly, the use of human Ads is not meant to be limiting since similar plasmids, viruses and techniques could be utilized for different non-human adenoviruses, for example bovine. Similarly, the use of adenoviruses is not meant to be limiting since similar plasmids, viruses and techniques could be utilized with other viruses, both human and non-human, for example baculovirus.

Use of Cre recombinase in these and other examples is not meant to be limiting as a person skilled in the art will readily appreciate that other enzymes capable of catalysing site-specific recombination between DNA sequences recognized by said enzymes could equally be employed in place of the Cre recombinase. An example, not meant to be limiting, of such an enzyme that could be substituted for Cre is the "FLP" recombinase of yeast in combination with its target site FRT (O'Gorman et al. Science 251, 1351, 1991).

A component of the invention is the use of human cells, such as 293 cells or other cells that may be deemed suitable in that they support the replication of the viral components of the invention, that express Cre recombinase and that can be transfected with the plasmids described herein and in the examples which follow, to generate a virus containing the desired modifications such as an insertion of foreign DNA or a modified fiber gene. It will be appreciated by those skilled in the art that the requisite cell lines can be generated by transfecting 293 cells or other cells, with a plasmid comprising the coding sequences for Cre under the control of suitable regulatory sequences, including a promoter and polyadenylation signal and containing, in addition, a selectable gene encoding, for example, resistance to G418 or histidinol. A person skilled in the art can readily obtain drug resistant cells that express the Cre recombinase in addition to the drug resistance gene used for selection. It will also be appreciated by one skilled in the art, based on the present disclosure, that host cells can also be induced to transiently express a recombinase by transfection with a plasmid comprising an expression cassette containing said recombinase gene or by infection with a viral vector that expresses the recombinase. Thus the example of 293Cre cells or other permanently transformed recombinase expressing cell lines is not meant to be limiting.

EXAMPLE 1

Two-plasmid, Site-specific Adenoviral Recombination

Figure 1:
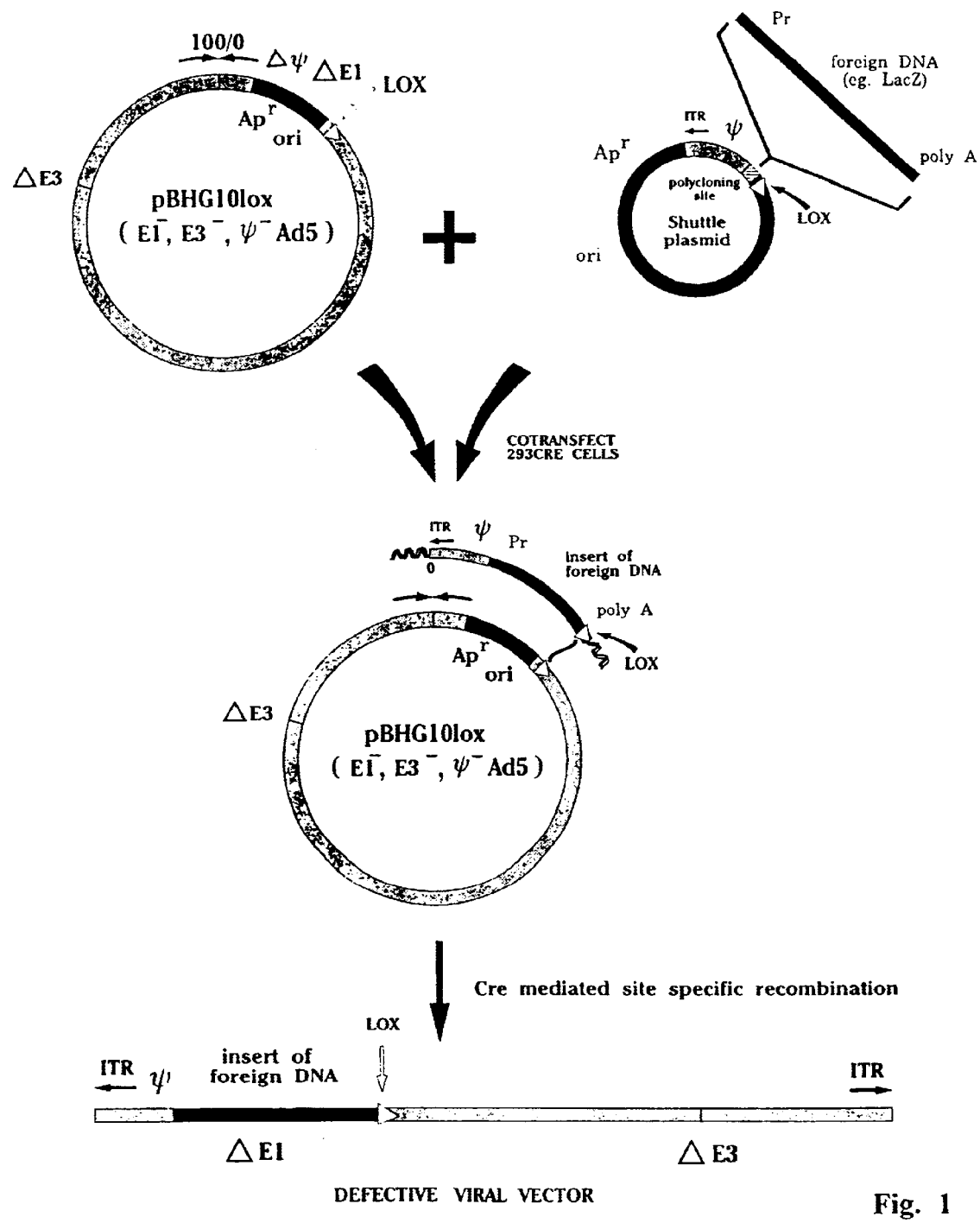
FIG. 1 is a diagrammatic representation showing a method for isolation of an Ad vector containing an expression cassette in E1 using the Cre/lox recombination system. pBHGloxΔE1,3 comprises a circularized form of the Ad genome with a deletion of the E1 region including the packaging signal and a bacterial plasmid origin of replication and an ampicillin resistance gene. The plasmid has a loxP site near the 5' end of the pIX gene of the Ad genome and a deletion of E3 sequences. The "shuttle plasmid" contains an ITR of the virus genome and a packaging signal, a polycloning site for insertion of a foreign DNA (e.g. bacterial β-galactosidase (LacZ)) and a loxP site inserted in the same relative orientation as the loxP site in pBHGloxΔE1,3. Cotransfection of these two plasmids into 293Cre cells that express Cre results in Cre-mediated recombination and formation of joint molecules that generate infectious viruses containing the foreign DNA insert. According to this invention, the ITR of the shuttle plasmid is replaced with a head-to-head ITR junction, thereby enhancing the efficiency of the site-specific recombination method.

FIG. 1 provides a graphic representation of the use of a plasmid, pBHGloxΔE1,3, which comprises a circularized form of the Ad genome in which part or all of the E1 region, including the packaging signal, is substituted by sequences comprising a bacterial plasmid origin of replication and an antibiotic resistance gene, such as that encoding ampicillin resistance. The plasmid further comprises a loxP site near the 5' end of the pIX gene of the Ad genome. The plasmid may also, optionally, have a deletion of E3 sequences (as shown in this illustration by the symbol ΔE3) which may optionally be substituted with one or more unique cloning sites for insertion of foreign DNA in the ΔE3 region.

A second component of the invention comprises a "shuttle plasmid" containing an ITR of the virus genome and a packaging signal, a polycloning site into which may be inserted a foreign DNA such as that encoding for bacterial β-galactosidase (LacZ) or any other gene, expression of which is desired either in a gene therapeutic or vaccine context, and a loxP site inserted in the same relative orientation as the loxP site in pBHGloxΔE1,3. To obtain high-efficiency rescue of the foreign DNA into an infectious viral vector, the two plasmids are cotransfected into human cells, such as 293Cre cells, PER-C6 cells, 911 cells, and the like, engineered to express Cre and which, in addition, express the E1 region of the Ad genome. It should be appreciated that the manner of provision of the recombinase is not critical. The recombinase may be constitutively expressed by the cell into which the two plasmids are introduced. The recombinase may be provided in trans, via a third plasmid, or in cis, by inclusion of a recombinase expression cassette in one of the introduced plasmids. In addition, it will be appreciated that any recombinase which efficiently induces site-specific recombination between sequences present on the two plasmids may be employed according to this methodology. Thus, the FLP recombinase, which recognizes the sequences known as FRT, may be used in place of the Cre/loxP combination, and thus, wherever Cre or loxP are mentioned herein, such mention should be read to include any other site-specific recombination system now known or henceforth discovered, when applied to the specific techniques disclosed and claimed herein. Cre-mediated recombination results in formation of joint molecules that generate infectious viruses containing the foreign DNA insert. Because pBHGloxΔE1,3 lacks the viral packaging signal, the only viruses that can form are those containing the packaging signal and foreign DNA of the shuttle plasmid. These are generated in large numbers because of the high-efficiency and specificity of Cre recombinase, and there is no background of non-recombinant virus in contrast to a method such as that of Hardy et al., J. Virol. 71(3): 1842–1849, (1997), which, even after three sequential passages in Cre expressing cells, results in a vector preparation still contaminated by starting (non-recombinant) virus.

EXAMPLE 2

Comparison of Homologous and Site-specific Recombination

Figure 2A:
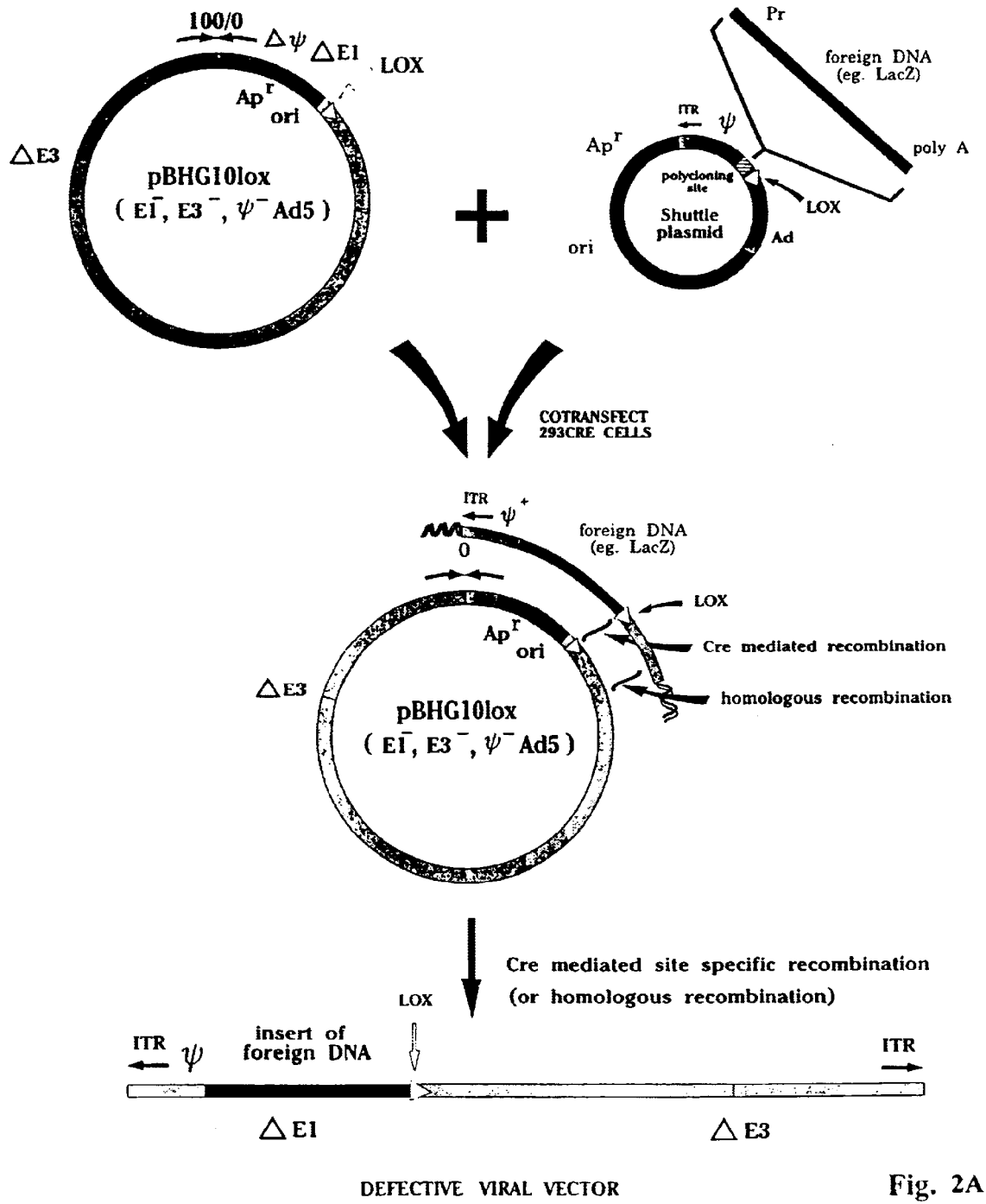
FIG. 2A illustrates a cotransfection experiment similar to that depicted in FIG. 1 except that the shuttle plasmid contains Ad sequences 3' of the lox site that overlap (are homologous) with viral sequences in pBHGloxΔE1,3 to the right of the lox site. Therefore an Ad vector containing an expression cassette in E1 can be generated by Cre/lox recombination when the two plasmids are cotransfected into 293Cre cells or alternatively by homologous recombination between overlapping sequences. The shuttle plasmid in the illustration permits a comparison of the efficiency obtainable from the two recombination modes. According to this invention, the ITR of the shuttle plasmid is replaced with a head-to-head ITR junction, thereby enhancing the efficiency of the site-specific recombination method.

FIG. 2A illustrates use of a modified shuttle plasmid wherein Ad sequences from about 10 mu to about 15 mu are present to the right of the lox site. These sequences permit homologous recombination to occur in the absence or presence of Cre. A shuttle plasmid such as that shown in this figure is generally used only for comparison purposes to assess the relative efficiency of homologous versus Cre-mediate recombination. As will be seen in the subsequent description of the invention, in the presence of Cre, overlapping sequences are unnecessary and can be omitted, although this disclosure does not require the absence of such sequences.

EXAMPLE 3

Sequences Useful in the Production of Plasmid Which May be Recombined in a Site Specific Manner to Produce Adenoviral Vectors FIG. 3 illustrates sets of oligonucleotides used in various cloning procedures. The double stranded oligonucleotide (SEQ ID NO:1 and SEQ ID NO:2; AB3233/3234) contains a loxP site with restriction sites for ScaI and EcoRI at one end of the oligo outside of the loxP region. When annealed, the oligonucleotides have BamHI/BglII overhangs which are designed for cloning into and concomitant destruction of the BglII site. The internal ScaI site found in SEQ ID NO:1 and SEQ ID NO:2 (AB3233/3234) was designed to facilitate determination of the orientation of the linker and also for subsequent deletion of Ad5 sequences from m.u. 9.8–15.8. The second linker (SEQ ID NO:3 and SEQ ID NO:4; AB14626/14627) has EcoRI and SalI overhangs and a multiple cloning region containing SmaI, BglII, HindIII and ScaI restriction sites.

EXAMPLE 4

Construction of Bacterial Plasmids Containing Circularized Forms of the Adenovirus Genome Suitable for Rescue of Viral Vectors Using Site-specific Recombination According to the General Scheme Illustrated According to FIG. 1

Figure 4A:
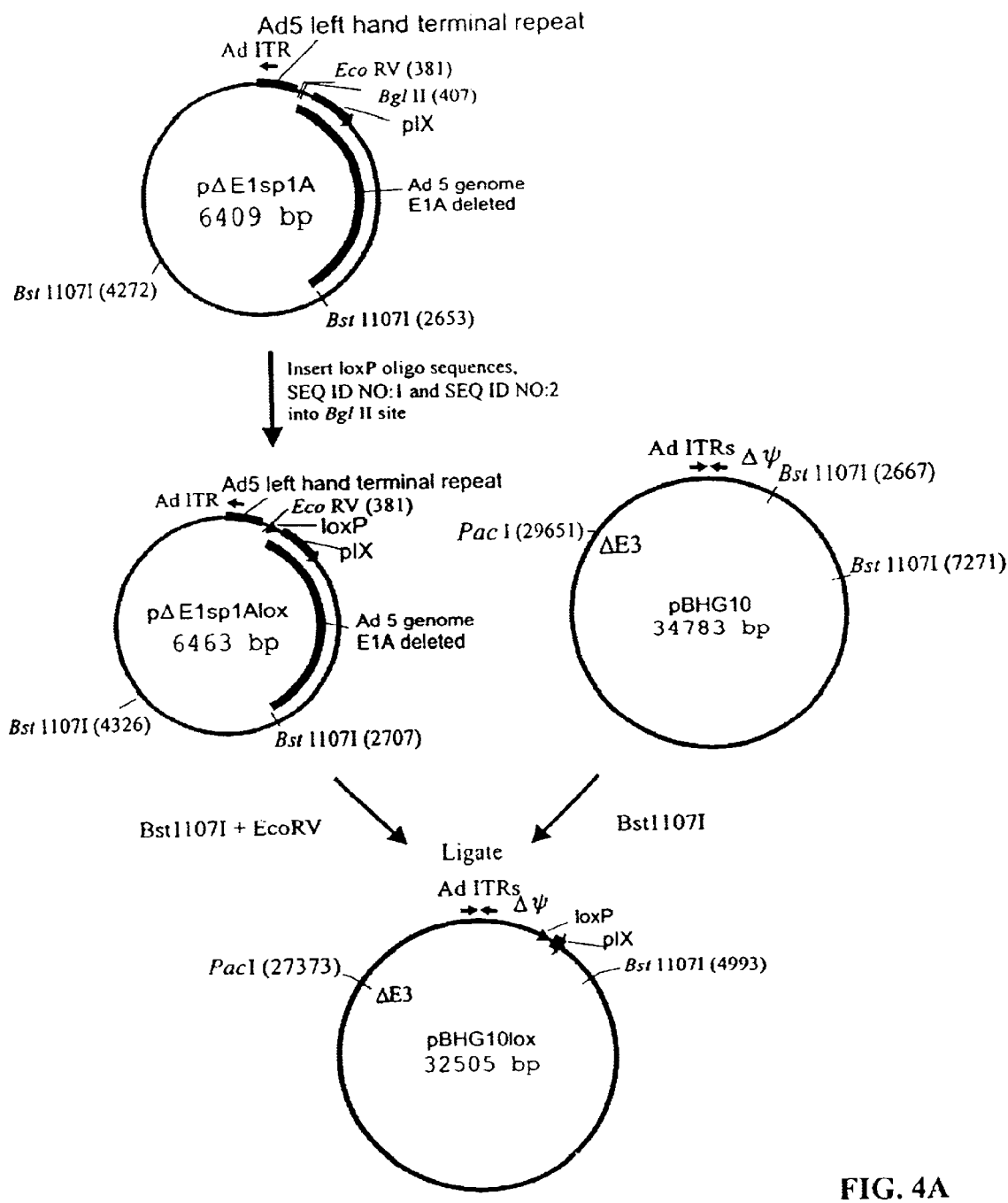
FIG. 4A illustrates the construction of a plasmid, derived from pBHG10 (Bett, A. J., Haddara, W., Prevec, L. and Graham, F. L "An efficient and flexible system for construction of adenovirus vectors with insertions or deletions in early regions 1 and 3." Proc. Natl. Acad. Sci. US 91: 8802–8806, 1994., available from Microbix Biosystems), wherein a loxP site is inserted at the 3' end of an E1 deletion and 5' (upstream) of the pIX gene. pBHGloxΔE1,3 was constructed by replacing the 4604 bp Bst1107I fragment from pBHG10 with the 2326 bp EcoRV/Bst1107I fragment from pΔE1sp1Alox (see FIGS. 5 and 5a). Foreign DNA sequences can be inserted into the unique PacI site of pBHGloxΔE1,3 for rescue of genes in E3.

FIG. 4A illustrates production of a plasmid, pBHGloxΔE1,3, a derivative of pBHG10, modified to contain a loxP site at the 3' end of the E1 deletion. As can be seen with reference to the figure, this plasmid was constructed by replacing the 4604 bp Bst1107I fragment from pBHG10 with the 2326 bp EcoRV/Bst1107I fragment from pΔE1sp1Δlox. The plasmid pΔE1sp1Δlox (FIG. 5A) was constructed by inserting an oligonucleotide bearing a loxP site (comprised of annealed oligos SEQ ID NO:1 and SEQ ID NO:2; AB3233 and AB3234) into the BglII site of pΔE1sp1A. Foreign sequences can be inserted into the unique PacI site of pBHGloxΔE1,3 for rescue of genes in E3. The plasmid illustrated in FIG. 4A can be selected from the series pBHG10 (as illustrated), pBHG11, pBHGE3, or like plasmid, for modification to contain a lox P site near the 3' end of E1 i.e. near the 5' end of the pIX gene at approximately nt 3520 in the conventional sequence of Ad5. Optionally E1 sequences from approximately nt 188 to approximately 3520 may be deleted from said plasmid. Like the parental plasmids (such as pBHG10, pBHG11 or pBHGE3) the modified pBHG derivative (e.g. pBHGloxΔE1,3, pBHGdX1Plox, pBHGE3lox, or like plasmid) lacks the packaging signal (ψ), and is consequently incapable of producing infectious virus in transfected host cells.

Figures 1, 4B:
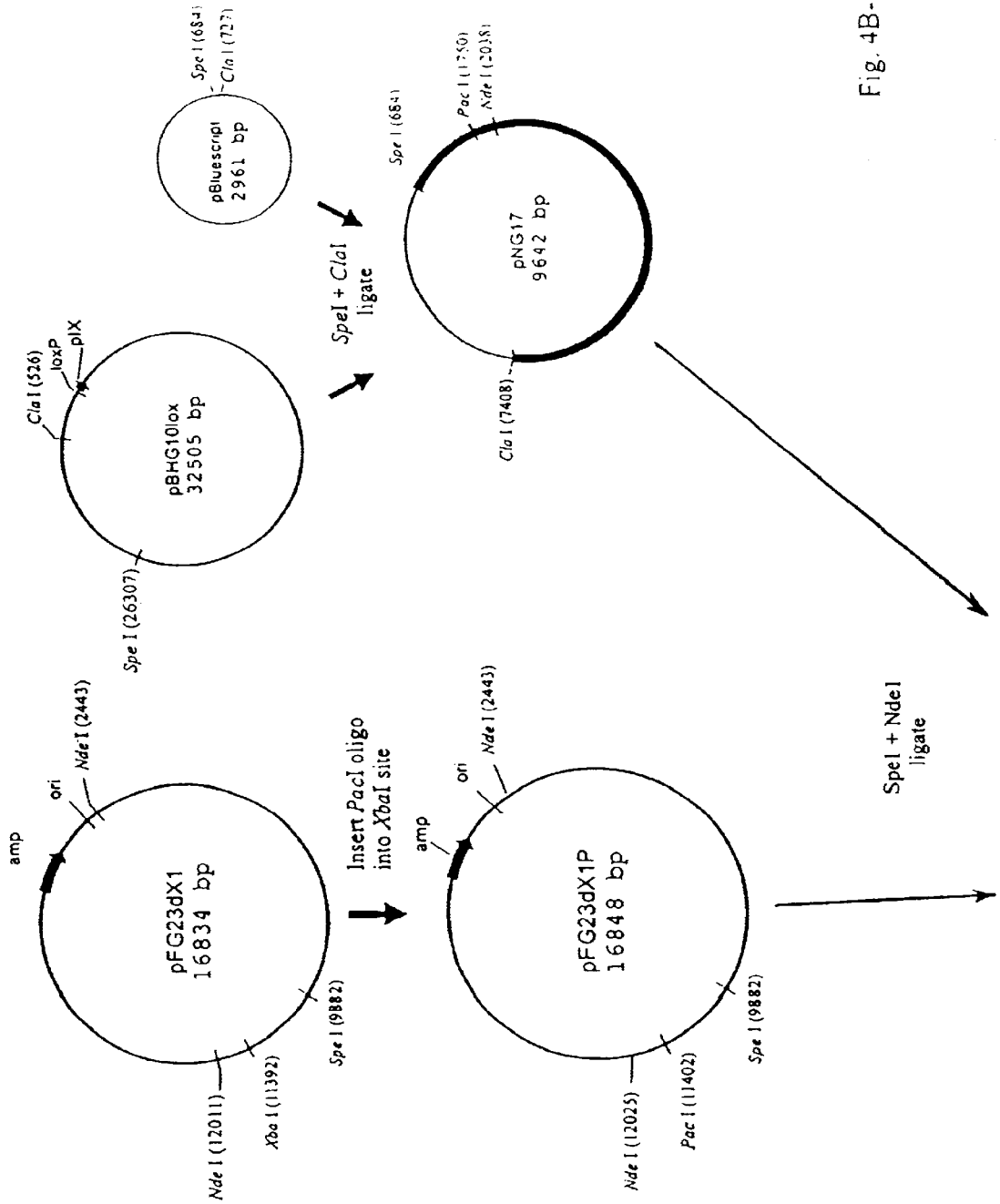
Figures 2, 4B:
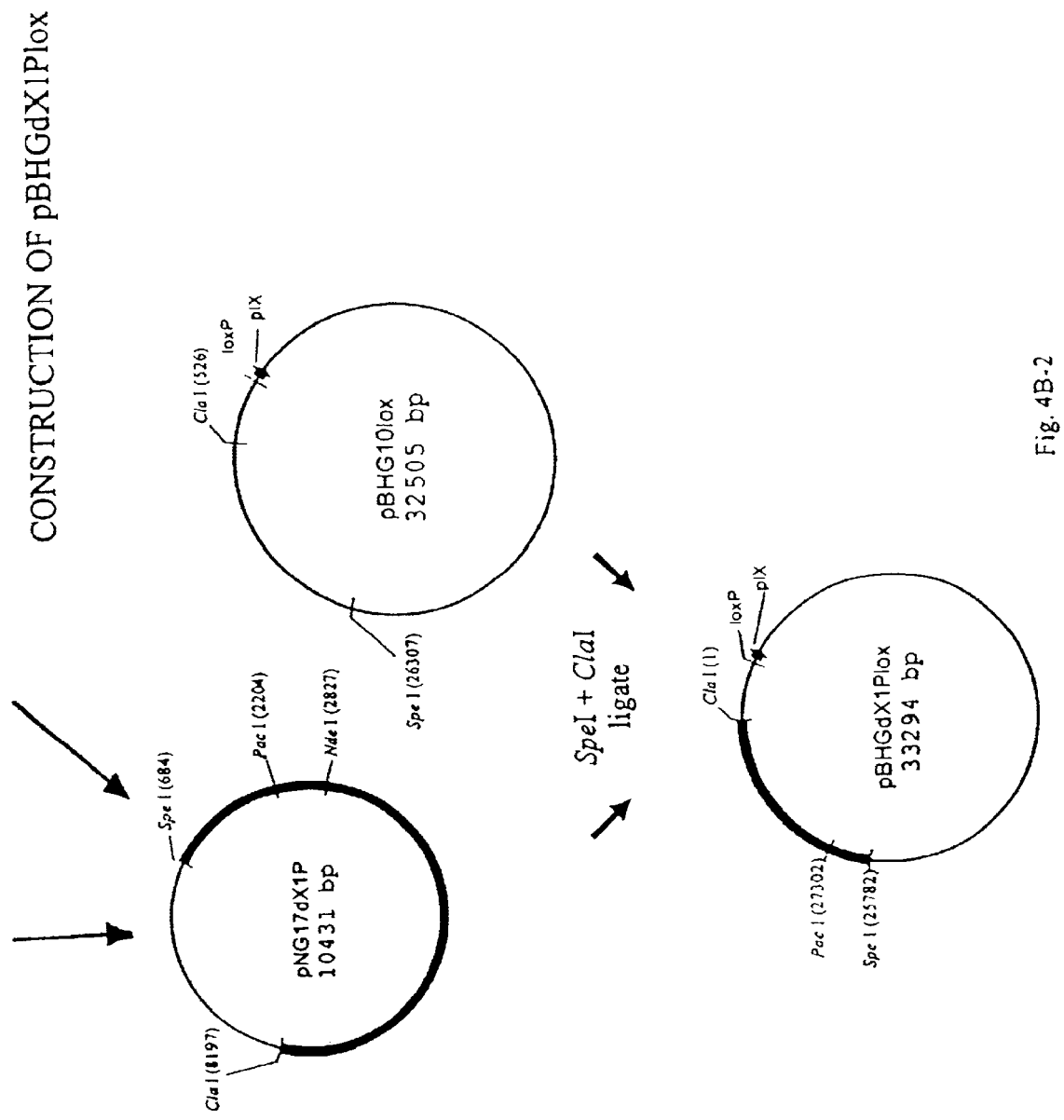

FIGS. 4B-1 and 4B-2 illustrates the construction of a plasmid, pBHGdX1Plox, containing a modified E3 deletion (taken from pFG23dX1P)and a lox site 5' of the pIX gene. The plasmid pFG23dX1P was constructed by inserting an oligonucleotide containing aPac site (AB14566; 5'-CTAGCTTAATTAAG-3', SEQ ID NO:9) into the XbaI site of pFG23dX1. The plasmid pNG17 was constructed by cloning the 6724 bp SpeI/ClaI fragment from pBHGloxΔE1,3 into pBluescript. The plasmid pNG17dX1P was constructed by replacing the 1354 bp SpeI/NdeI fragment from pNG17 with the 2129 bp SpeI/NdeI fragment from pFG23dX1P. The plasmid pBHGdX1P was constructed by replacing the 6724 bp SpeI/ClaI fragment from pBHGloxΔE1,3 with the 7495 bp SpeI/ClaI fragment from pNG17dX1P.

Figure 4C:
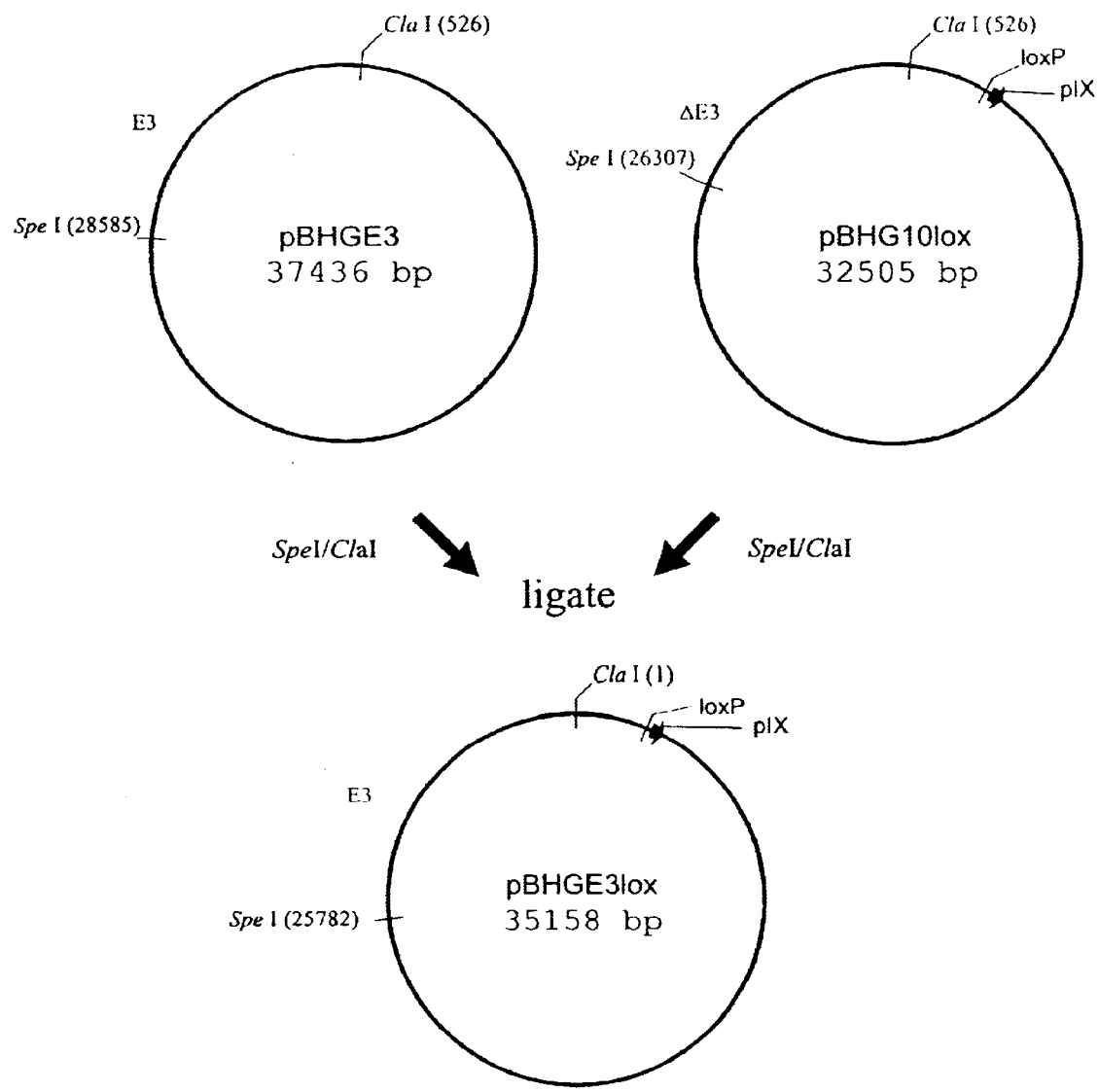
FIG. 4C illustrates the construction of pBHGE3lox, a plasmid derived from pBHGE3 and pBHGloxΔE1,3 constructed by replacing the 6724 bp SpeI/ClaI fragment from pBHGloxΔE1,3 with the 9377 bp SpeI/ClaI fragment from pBHGE3. PBHGE3lox contains a complete E3 region for isolation of viral vectors that retain a wild-type E3.

FIG. 4C illustrates the construction of a plasmid containing a wild-type E3 region and a loxP site 5' of the pIX gene. The plasmid pBHGE3lox was constructed by replacing the 6724 bp SpeI/ClaI fragment from pBHGloxΔE1,3 with the 9377 bp SpeI/ClaI fragment from pBHGE3.

EXAMPLE 5

Construction of Shuttle Plasmids for Recombination with Adenoviral Rescue Plasmid, Constructed According to Example 4

As described above, a second embodiment of the invention comprises a shuttle plasmid selected from a series of plasmids containing, minimally: the left end of the viral genome including all or most of the left Inverted Terminal Repeat (ITR nts 1–103 of the Ad 5 DNA) and the packaging sequence, and optionally a polycloning site or optionally an expression cassette. With reference to FIGS. 5–8, such shuttle plasmids are modified to contain a lox P site in the same orientation as the loxP site in the pBHG derivative, (see Example 4, referred to herein as the "rescue plasmid"), said loxP site being positioned in said shuttle plasmid to the right of said polycloning site or said expression cassette.

Figure 5A:
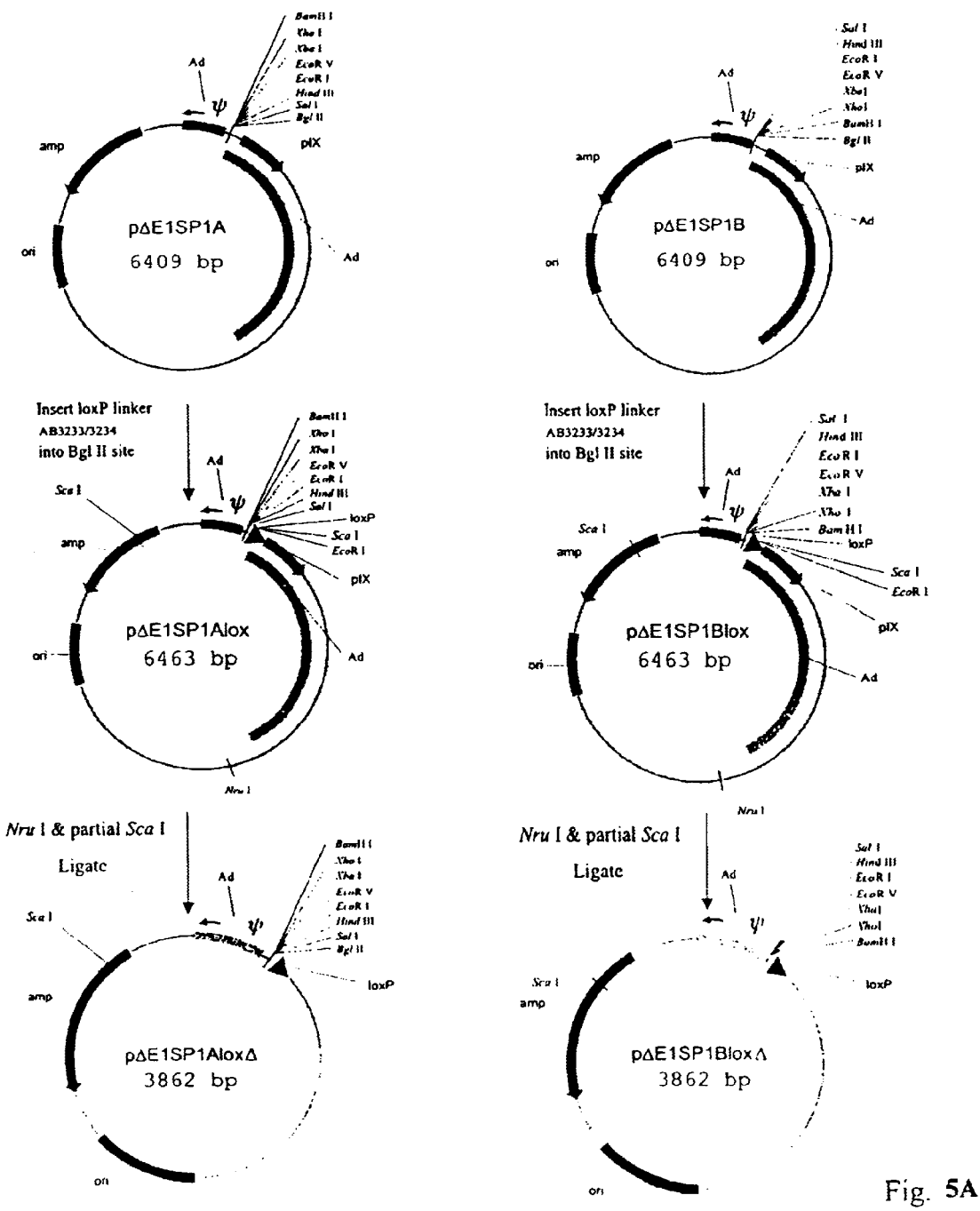
FIG. 5A illustrates the construction of shuttle plasmids derived from pΔE1SP1A and pΔE1SP1B wherein a loxP site is introduced 3' of the packaging signal. The plasmids pΔE1sp1Alox and pΔE1sp1Blox were constructed by inserting an oligonucleotide bearing a loxP site (comprised of SEQ ID NO:1 and SEQ ID NO:2 annealed oligonucleotide sequences, also identified as AB3233 and AB 3234) into the BglII site of pΔE1sp1A. Subsequent digestion with Nru I and partial Sca I digestion followed by ligation generated pΔE1SP1AloxΔ and pΔE1SP1BloxΔ.
Figure 5B:
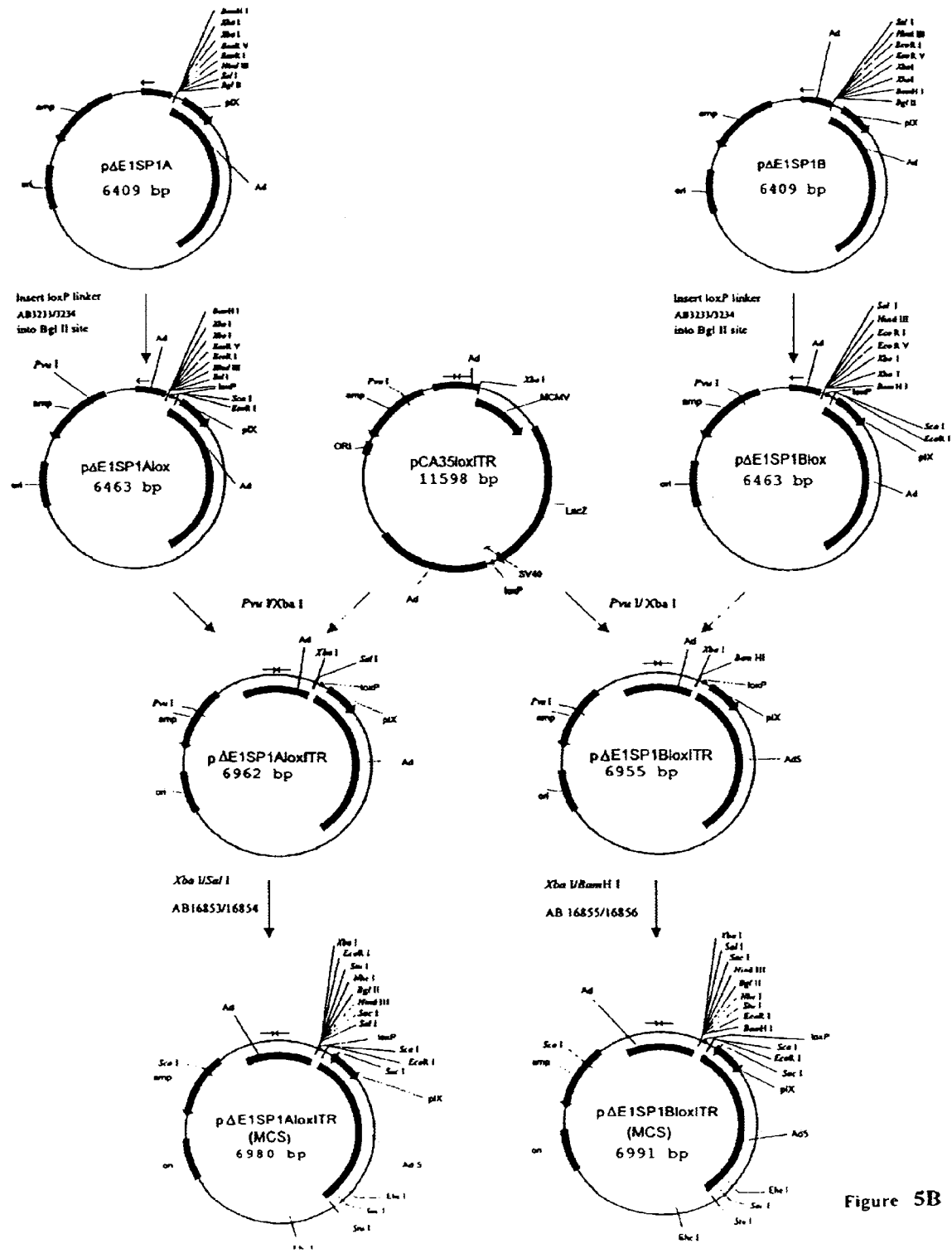
FIG. 5B. Construction of shuttle plasmids. The plasmids pΔE1SP1AloxΔ and pΔE1SP1Blox were constructed by inserting a loxP linker (SEQ ID NO:1 and SEQ ID NO:2; AB3233/AB3234) into the BglII site of pΔE1SP1A and pΔE1SP1B. The plasmids pΔE1SP1AloxITR and pΔE1SP1BloxITR were produced by replacing the Pvu I/Xba I fragment of pΔE1SP1Alox and pΔE1SP1Blox with a PvuI/Xba I fragment from pCA35loxITR. The resulting plasmids now contain an ITR junction instead of just a single left end ITR. The plasmids pΔE1SP1AloxITR(MCS) and pΔE1BloxITR(MCS) were generated by inserting oligonucleotides (SEQ ID NO:12, AB 16853, and SEQ ID NO:13, AB16854) and (SEQ ID NO:14, AB16855, and SEQ ID NO:15, AB16856) into the unique Xba I/Sal I sites of pΔE1SP1AloxITR and Xba I/BamH I sites of pΔE1SP1BloxITR respectively.
Figure 5C:
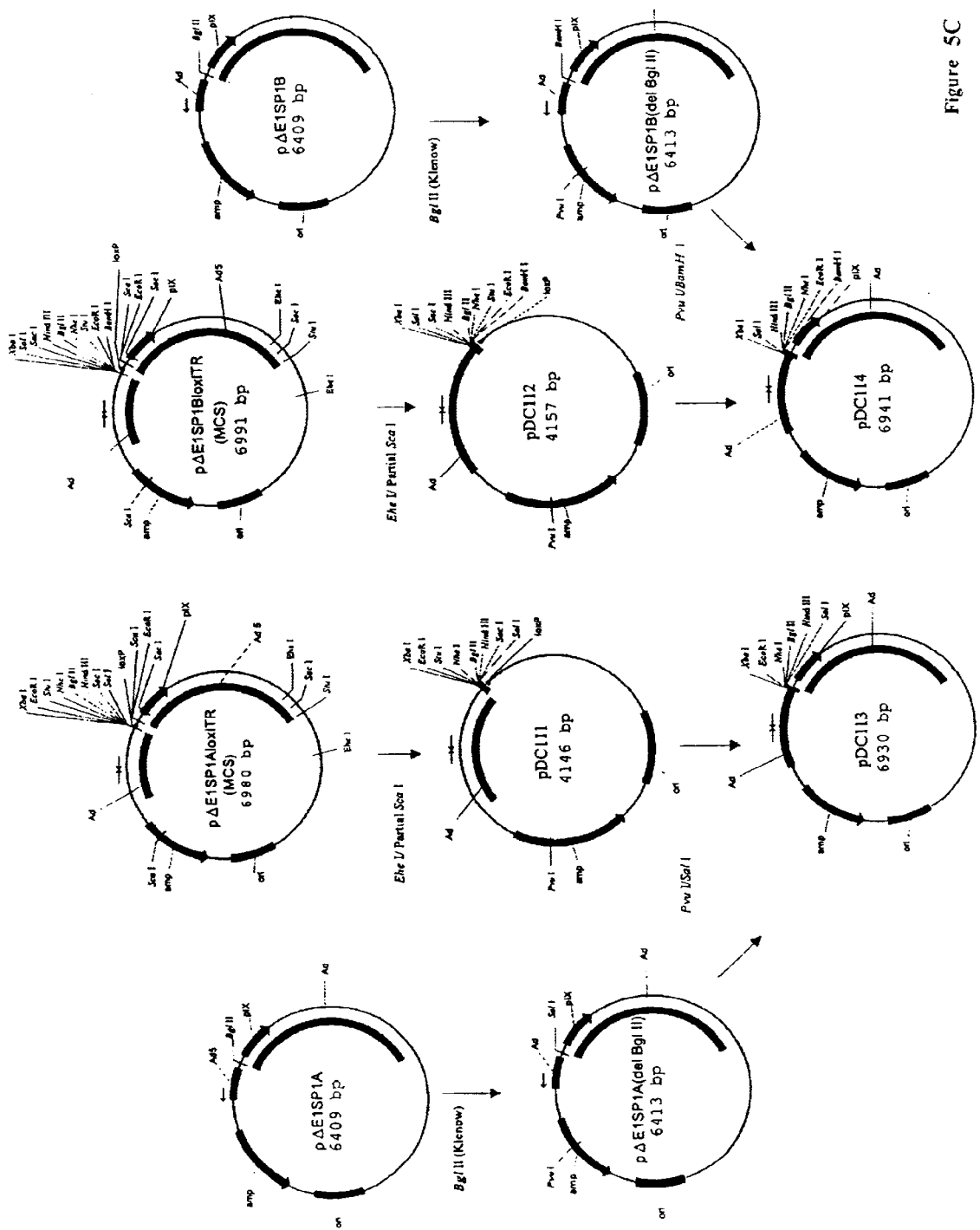
FIG. 5C. Construction of shuttle plasmids. The plamids pDC111 and DC112 were produced by digesting pΔE1SP1AloxITR(MCS) and pΔE1SP1BloxITR(MCS) with Ehe I followed by a partial digest with Sca I followed by ligation. The resulting plasmids now lack essential left end Ad sequences required for rescue of Ad vectors by homologous recombination. These shuttle plasmids will only produce plaques in cotransfection with Ad genomic plasmids if there is recombination between loxP sites. The shuttle plasmid pDC113 was generated by replacing the Fvu I/Sal I site of pDC111 with a similar fragment from pΔE1SP1A(del Bgl II). The plasmid pDC114 was produced by replacing the Pvu I/BamH I of pDC112 with a similar fragment from pΔE1SP1B(del Bgl II). The plasmids, pDC113 and pDC114, are shuttle plasmids which contain an ITR junction and Ad sequences for homologous recombination, but they lack the loxP site found in previous plasmids.
Figure 5D:
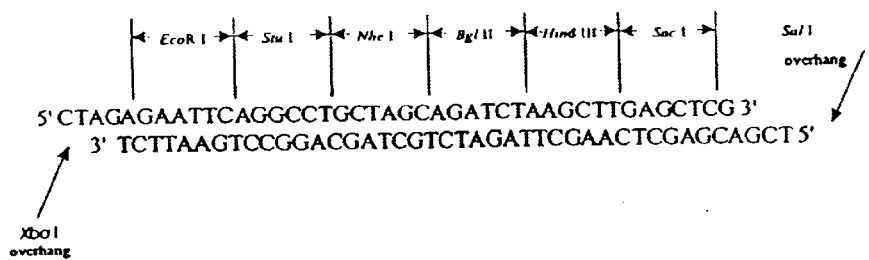
FIG. 5D. Synthetic oligonucleotides for use in construction of pΔE1SP1AloxITR(MCS) and pΔE1BloxITR(MCS) of FIG. 5B.
Figure 5D:
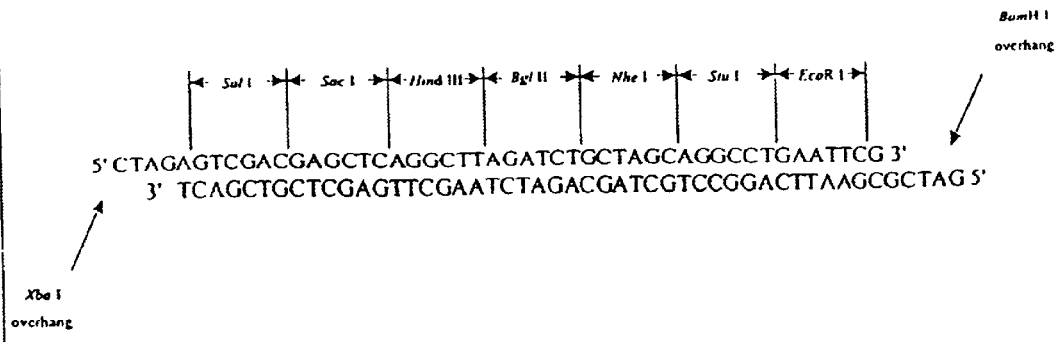

FIG. 5A illustrates the construction of shuttle plasmids derived from pΔE1SP1A and pΔE1SP1B wherein loxP sites are introduced 5' of the pIX gene. The plasmids, pΔE1sp1A and pΔE1SP1B are left end shuttle plasmids containing Ad5 sequences from m.u. 0–15.8 with E1 sequences deleted between m.u.1 and 9.8. They are identical except that the restriction sites in the multiple cloning region are reversed. A synthetic loxP linker (SEQ ID NO:1 and SEQ ID NO:2; AB3233/3234) was introduced into the BglII site of each plasmid generating pΔE1SP1Alox and pΔE1SP1Blox. Ad5 sequences from m.u. 9.8–15.8 were removed by digesting the plasmids with NruI, partially cutting with ScaI followed by self-ligation. The plasmids thus generated are called pΔE1SP1AloxΔ and pΔE1SP1BloxΔ.

Figure 6A:
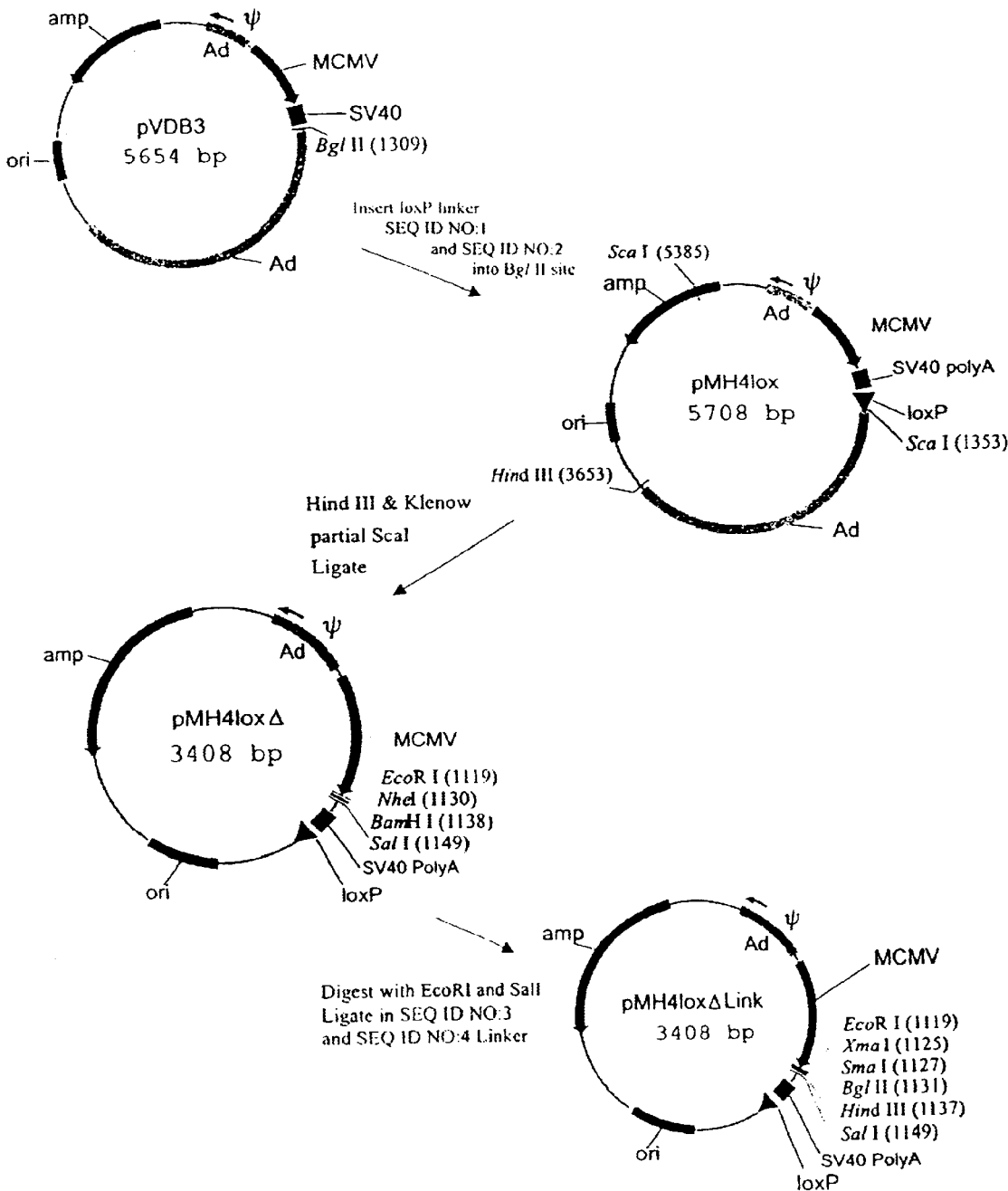
FIG. 6A illustrates the construction of pMH4lox, pMH4loxΔ (also referred to herein as pDCMH4lox(Ad del) and pMH4loxΔlink (also referred to herein as pDCMH4lox (Ad del) Linker), plasmids that contain lox sites and a promoter and polyadenylation signal and polycloning sites for insertion of foreign DNA to produce expression cassettes in which transcription is driven by the murine cytomegalovirus immediate early gene promoter. Plasmid pVDB3 (see FIG. 6B) is derived from pMH4 but contains a pUC based origin of replication rather than a pBR322 origin. It contains Ad5 sequences from m.u. 0–15.8 with E1 sequences deleted between mu. 1 and 9.8 and substituted with an expression cassette: a 0.5 kbp (−491 to +36) fragment of the MCMV IE promoter, unique restriction enzyme sites for cloning (Eco RI, Nhe I, Bam HI and Sal I) followed by an SV40 polyadenylation signal. To make pMH4lox, a loxP linker (SEQ ID NO:1 and SEQ ID NO:2; AB3233/3234) was introduced into the BglII site of pVDB3. Ad5 sequences m.u. 9.8–15.8 were deleted from pMH4lox by digesting with Hind III, treating with the Klenow fragment of E. coli DNA polymerase then partially digesting with Sca I followed by self-ligation. The resulting shuttle plasmid, pMH4loxΔ, (also referred to herein as pDCMH4lox(Ad del)), can be used with pBHGloxΔE1,3 to produce Ad vectors via Cre/lox mediated recombination. To make pMH4loxΔ a more flexible plasmid for cloning purposes, a linker (SEQ ID NO:3 and SEQ ID NO:4; AB14626/14627) containing a different multiple cloning region was introduced between the Eco Rl and Sal I sites resulting in pMH4loxΔlink, (also referred to herein as pDCMH4lox(Ad del)Linker).

FIG. 6A illustrates the construction of pMH4lox and pMH4loxΔ plasmids that contain a promoter and polyadenylation signal and polycloning sites for insertion of foreign DNA to produce expression cassettes in which transcription is driven by the murine cytomegalovirus immediate early gene promoter. Plasmid pVDB3 is derived from pMH4 but contains a pUC-based origin of replication, rather than a pBR322 origin. It contains Ad5 sequences from m.u. 0–15.8 with E1 sequences deleted between m.u. 1 and 9.8 and substituted with an expression cassette: a 0.5 kbp (–491 to +36) fragment of the MCMV IE promoter, unique restriction enzyme sites for cloning (Eco RI, Nhe I, Bam HI and Sal I) followed by an SV40 polyadenylation signal. To make pMH4lox, a loxP linker (SEQ ID NO:1 and SEQ ID NO:2; AB3233/3234) was introduced into the BglII site of pVDB3. Ad5 sequences m.u. 9.8–15.8 were deleted from pMH4lox by digesting with Hind III, treating with the Klenow fragment of E. coli DNA polymerase then partially digesting with Sca I followed by self-ligation. The resulting shuttle plasmid, pMH4loxΔ, can be used with pBHGloxΔE1,3 to produce Ad vectors via Cre/lox mediated recombination. To make pMH4loxΔ a more flexible plasmid for cloning purposes, a linker (SEQ ID NO:3 and SEQ ID NO:4; AB14626/14627), containing a different multiple cloning region, was introduced between the Eco RI and Sal I sites resulting in pMH4loxΔlink.

Figure 6B:
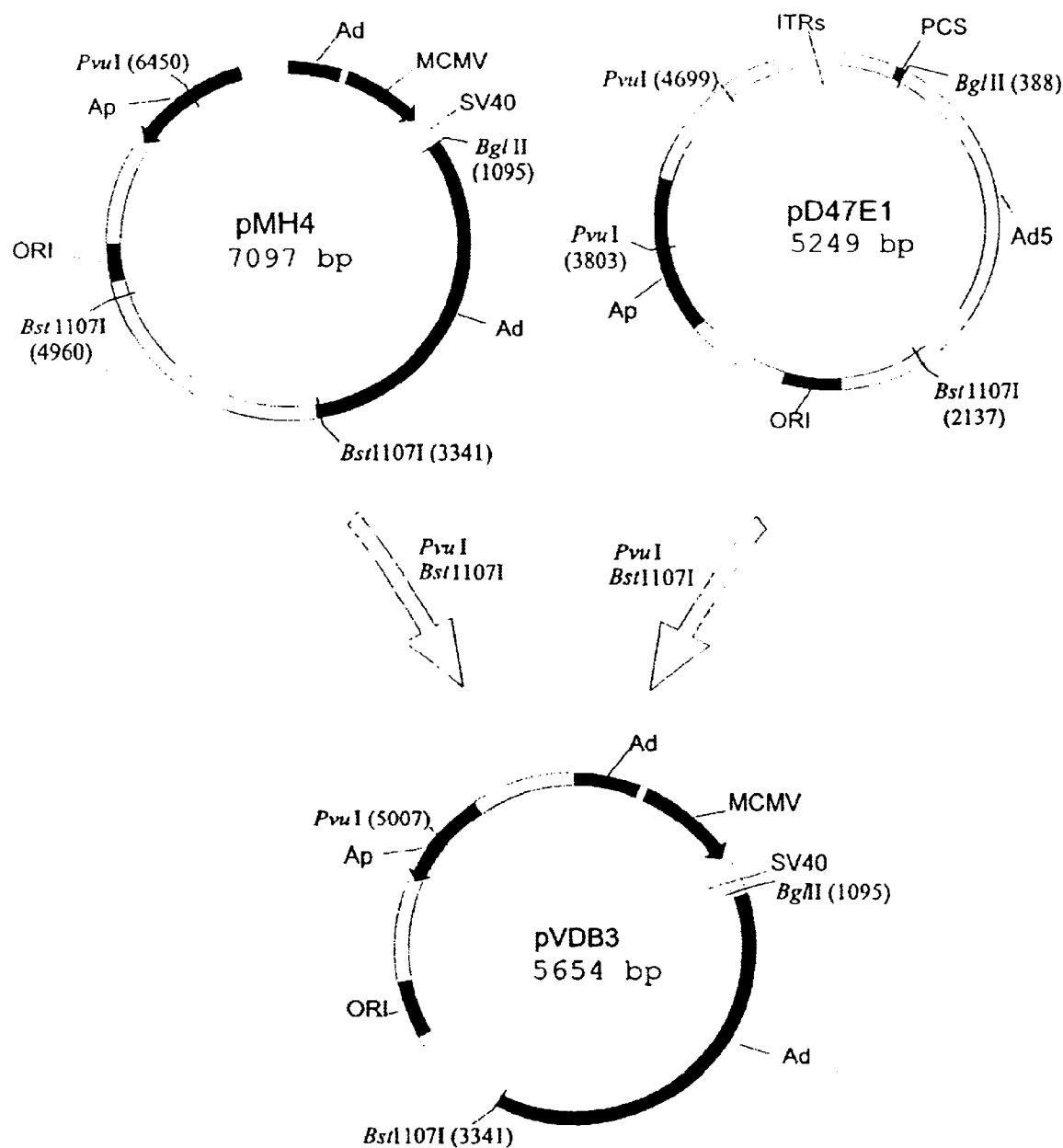
FIG. 6B illustrates the construction of plasmid pVDB3 derived from pMH4 but containing a pUC based origin of replication rather than a pBR322 origin. A PvuI to Bst 11071 fragment from pMH4 (Microbix Biosystems) was ligated to a Bst 11071 to Pvu I fragment from pD47E1 containing a pUC based (pNEB193, New England Biolabs) origin of plasmid DNA replication to generate pVDB3.

FIG. 6B illustrates the construction of plasmid pVDB3. A PvuI to Bst 11071 fragment from pMH4 (Microbix Biosystems) was ligated to a Bst 11071 to Pvu I fragment from pD47E 1 containing a pUC-based (pNEB193, New England Biolabs) origin of plasmid DNA replication to generate pVDB3.

Figure 7:
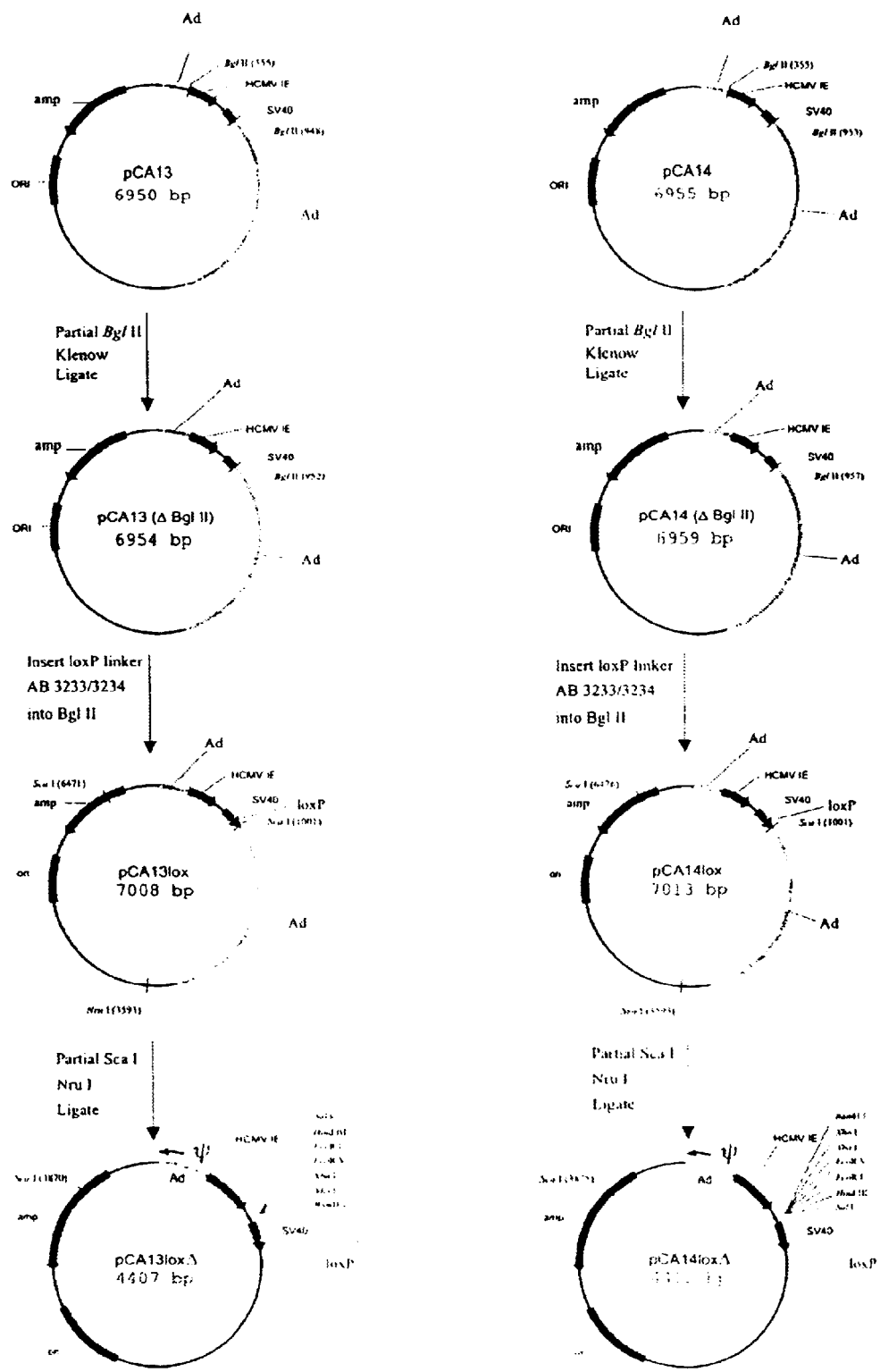
FIG. 7 illustrates construction of HCMV loxP plasmids, pCA13loxΔ and pCA14loxΔ, in which transcription of foreign genes is regulated by the human cytomegalovirus immediate early gene promoter. The plasmids pCA13 (ΔBglII) and pCA 14(ΔBglII) were generated by digesting pCA13 and pCA14 partially with BglII, Klenowing and self-ligating. A synthetic loxP oligonucleotide (SEQ ID NO:1 and SEQ ID NO:2; AB3233/3234) was introduced into the unique BglII sites of pCA13(ΔBglII) and pCA14 (ΔBglII) producing pCA13lox and pCA14lox respectively. Ad5 sequences, m.u. 9.8–15.8, were removed from pCA13lox and pCA14lox by cutting each plasmid with NruI and partially digesting each with ScaI followed by self ligation.

FIG. 7 illustrates construction of HCMV loxP plasmids in which transcription of foreign genes is regulated by the human cytomegalovirus immediate early gene promoter. The plasmids pCA13 and pCA14 contain the Ad5 genomic sequences from m.u. 0 to 15.8 with E1 sequences between m.u. 1 and 9.8 replaced by the HCMV IE promoter (–299 to +72, relative to the transcription start), a polycloning region and an SV40 polyadenylation signal. (Plasmids pCA13 and pCA14 are available from Microbix Biosystems). The expression cassette in each case is oriented parallel to the direction of E1 transcription (rightwards). The only difference between pCA13 and pCA14 is in the orientation of the multiple cloning region. The plasmids pCA13(ΔBglII) and pCA14(ΔBglII) were generated by digesting pCA13 and pCA14 partially with BglII, Klenowing and self-ligating. A synthetic loxP oligonucleotide (SEQ ID NO:1 and SEQ ID NO:2; AB3233/3234) was introduced into the unique BglII sites of pCA13(ΔBglII) and pCA14(ΔBglII) producing pCA13lox and pCA14lox respectively. Ad5 sequences, m.u. 9.8–15.8, were removed from pCA13lox and pCA14lox by cutting each plasmid with NruI and partially digesting each with ScaI followed by self ligation. The resulting plasmids, pCA13loxΔ and pCA14loxΔ are useful shuttle plasmids for the rescue of first generation Ad vectors by Cre/lox recombination.

FIG. 8A illustrates the construction of a plasmid, pCA36loxΔ, for rescue of the β-galactosidase gene into adenovirus vectors. Naturally, the rescued gene may be any foreign gene, and is not restricted to the use of a marker gene, such as the marker beta-gal gene, which is used herein for illustrative purposes. The plasmid pCA36 contains the β-gal cDNA under control of the short MCMV IE promoter (−491 to +36) followed by an SV40 polyadenylation signal. Plasmid pCA36 was made by inserting the LacZ gene into pMH4 (available from Microbix Biosystems) and is described by Addison, C. L., Hitt, M., Kunsken, D. and Graham, F. L., in "Comparison of the human versus murine cytomegalovirus immediate early gene promoters for transgene expression in adenoviral vectors," J. Gen. Virol. 78: 1653–1661, 1997." A synthetic loxP site (SEQ ID NO:1 and SEQ ID NO:2; AB3233/3234) was introduced into the BglII site of pCA36 resulting in pCA36lox. This plasmid was then digested with Nru I and partially digested with Sca I, a 7646 bp fragment was gel purified and self ligated yielding pCA36loxΔ. This plasmid contains Ad sequences from m.u. 0–1, and not only has the deletion of E1 sequences present in the parental plasmids pCA36 and pCA36lox, but additionally is deleted of Ad5 sequences from m.u.9.8–15.8.

EXAMPLE 6

Demonstration of Enhance Efficiency of Site-specific Recombination in Comparison with Homologous Recombination In a third embodiment of the invention, two plasmids containing loxP or other recombinase recognition sites are cotransfected into 293Cre or other appropriate cells (expressing an appropriate recombinase, Cre for purposes of this example). The Cre enzyme catalyses site-specific recombination between said lox P sites present in each vector. As illustrated in FIG. 1, it will be readily seen by one skilled in the art that Cre-mediated recombination between said lox P sites generates a viable virus by joining pBHG sequences to a DNA segment containing ψ and ITR sequences. Furthermore, by virtue of the design and construction of the pBHG derivative and the shuttle plasmid, the resulting viral vector contains the expression cassette located to the left of the lox P site in said shuttle plasmid, thereby providing a simple and efficient means for isolating viral vectors containing foreign DNA insertions and expression cassettes for synthesis of proteins from foreign genes.

To test and demonstrate the validity of the approaches outlined above and to determine the degree of improvement in efficiency of vector isolation compared to known methods, a number of experiments were conducted in which a vector carrying a LacZ expression cassette inserted near the left end of the Ad genome was constructed. The efficiency of Cre/lox mediated recombination was compared with that of homologous recombination, by measuring the numbers of virus plaques obtained from cotransfections of 293 cells versus the numbers obtained following cotransfections of 293Cre4 cells (see, for example, U.S. patent application Ser. No. 08/473,168, filed Jun. 7, 1995; see also WO96/40955, hereby incorporated by reference).

The results shown in Table 1 indicate that Cre/lox mediated recombination (cotransfections of 293Cre4 cells with plasmids that both contain lox sites) was approximately 35-fold more efficient than homologous recombination (cotransfections of 293 cells or cotransfections of 293Cre4 cells with plasmids that do not both contain lox sites). A 35-fold increase represents a very significant and unexpectedly high improvement over efficiencies of vector rescue when virus isolation is dependent on homologous recombination. Coupled with the fact that the only infectious virus present in the transfected cell preparation are recombinants, rather than contaminating starting virus, the efficiency, cleanliness and convenience of this method in comparison to known methods represent significant advances in the art. Thus, with this new method it will be possible to reduce the amount of plasmid DNA used in cotransfections and reduce the number of dishes of 293 (293Cre) cells needed in cotransfections for rescue of viral vectors. It will also aid in the rescue of constructs which, for unknown reasons, might be otherwise difficult to rescue (e.g. rescue of vectors containing large foreign DNA inserts in E1 is often inefficient for reasons that are not known).

To confirm that the enhanced efficiency of plaque formation following cotransfection of 293 Cre cells with pCA36+ pBHGloxΔE1,3 was due to Cre-lox dependent recombination (versus, for example, enhanced efficiency of homologous recombination) we constructed a derivative of pCA36lox, named pCA36loxΔ (see FIG. 8A), from which overlapping Ad sequences to the right of the lox site had been removed, thus virtually eliminating any possibility of homologous recombination. This new shuttle plasmid was then tested for ability to generate vectors in a second experiment in which 293 or 293Cre cells were cotransfected with this plasmid or with pCA36 or pCA36lox for comparison along with pBHGloxΔE1,3. It can be seen from the results shown in Table 2 that pCA36loxΔ only generated viral plaques following cotransfection of 293Cre cells with pBHGloxΔE1,3. In contrast pCA36 or pCA36lox were able to generate small numbers of plaques on 293 cells. However, again, the efficiency was markedly enhanced if 293Cre cells were cotransfected with pCA36lox and pBHGloxΔE1,3. Thus the use of Cre-lox recombination results in a surprisingly efficient system for rescue of foreign DNA into Adenovirus vectors.

To confirm that transfection of 293Cre cells with pCA36lox (a lacZ-containing shuttle plasmid with a loxP site located between the expression cassette and the pIX coding sequence as illustrated in FIG. 8A) and pBHGloxΔE1,3 resulted in viruses containing the desired insert of foreign DNA, 26 recombinant plaques were isolated, expanded and analyzed for expression of LacZ. All 26 (100%) were positive for β-galactosidase expression. Furthermore, analysis of the structure of the viruses confirmed that all 26 had the expected DNA structure illustrated in FIG. 1. Further confirmation of the efficiency and specificity of the Cre/lox system for rescue of expression cassettes was obtained through analysis of 6 plaque isolates obtained by cotransfection of 293Cre cells with pCA36loxΔ and pBHGloxΔE1,3 (Table 2). All 6 plaque isolates expressed β-galactosidase and all 6 had the expected DNA structure illustrated in FIG. 1. Because 100% of recombinant viruses produced by cotransfection of 293Cre cells with plasmids containing appropriately engineered lox sites have the correct structure and express the transgene, (β-galactosidase in these examples), it will be appreciated by those skilled in the art that one could readily produce recombinant viruses carrying other foreign DNA inserts by constructing shuttle plasmids derived from the plasmids shown in FIGS. 5, 6 and 7 or similar plasmids, and cotransfecting said modified shuttle plasmids into 293Cre or like cells, along with pBHGloxΔE1,3 or similar pBHG plasmids containing a lox site near the end of E1. It will be further appreciated by those skilled in the art that because of the high-efficiency of rescue with this approach, only small numbers of 293Cre cultures and small amounts of DNA need be used to obtain the desired recombinant viruses. Furthermore, because only the desired recombinant viruses are obtained from said cotransfections, it would not be essential to plaque purify and analyze viral progeny obtained according to the method of this invention. In addition, after the initial isolation of the recombinant viruses from 293 Cre cells, said viruses can be propagated in host cells such as 293, 911 or PERC-6 cells or the like which do not express recombinase.

EXAMPLE 7

Site-specific Shuttle Plasmid-virus Recombination

Hardy et al., J. Virol. March: 1997, 71(3):1842–1849, and see also WO97/32481 disclosed a method whereby an infectious DNA vector was used in combination with a plasmid in combination with lox-Cre recombination to generate recombinant adenoviruses. However, according to that method, residual infectious starter virus remains in the recombinant virus preparation, requiring repeated passage of the preparation in a Cre expressing cell to eliminate this background. An advancement to such techniques is provided herein by combination of Cre-lox recombination and use of adenoviral DNA bound to the adenoviral terminal protein (TP). The result of this combination is high-efficiency infection combined with site-specific recombination.

The use of a two plasmid system for isolation of viral vectors or modified viruses is not meant to be limiting. From the instant disclosure, it will be appreciated by those skilled in the art that one could use, as one component of the system, viral DNA from a modified virus whose genome contains lox P sites at useful positions. An excellent example, not meant to be limiting, is use of AdLC8, AdLC8c or AdLC8cluc described by Parks, R. J., Chen, L., Anton, M., Sankar, U., Rudnicki, M. A. and Graham, F. L., in "A new helper-dependent adenovirus vector system: removal of helper virus by Cre-mediated excision of the viral packaging signal," Proc. Natl. Acad. Sci. U.S. 93: 13565–13570, 1996. These viruses contain a "floxed" packaging signal, which is excised following virus infection of 293Cre cells. Therefore, cotransfection of 293Cre cells with viral DNA extracted from AdLC8, AdLC8c or AdLC8cluc in such a way as to retain the covalent linkage to TP, according to methods taught by Sharp et al., "The infectivity of adenovirus 5 DNA-protein complex," Virology, December 1976: 75(2): 442–456; Chinnadurai, et al., "Enhanced infectivity of adenovirus type 2 DNA and a DNA-protein complex," J. Virol. April 1978: 26(1):195–199, and a shuttle plasmid such as that illustrated in FIG. 5, 6, 7 or 8 results in Cre-mediated recombination to generate a new vector containing the sequences derived from the shuttle plasmid, spanning the region from the ITR and packaging signal of the shuttle across the optional polycloning site or optional expression cassette to the lox P site of said shuttle plasmid. For example, not meant to be limiting, as illustrated in FIG. 8B, using a lacZ-encoding plasmid, similar to that shown in FIG. 8A, and AdLC8c DNA-TP, one skilled in the art could readily isolate the desired recombinant virus containing lacZ or other foreign genes by cotransfection of 293Cre cells with DNA extracted from AdLC8c-TP and said Lac Z-encoding plasmid. Optionally, as illustrated in FIG. 8C, one could cotransfect 293Cre cells with restriction endonuclease treated AdLC8c DNA-TP and a shuttle plasmid selected from the set of plasmids illustrated in FIGS. 5, 6, 7 and 8 to produce infectious virus by Cre-mediated recombination. The viral DNA extracted from AdLC8c according to this method retains the terminal protein which has been shown to increase the efficiency of transduction of recipient cells with said DNA (Sharp P A, Moore C, Haverty J L, "The infectivity of adenovirus 5 DNA-protein complex," Virology December 1976; 75(2):442–456). It will be apparent to those skilled in the art that the left most lox site is not needed and may optionally be deleted if AdLC8cDNA-TP is to be cut with restriction enzymes prior cotransfection. Furthermore, optionally, after restriction enzyme digestion, the large right end fragment of AdLC8cDNA-TP could be purified prior to cotransfection.

FIG. 8D is a diagrammatic representation of a method for constructing shuttle plasmids expressing Cre. The Cre expression cassette was obtained from the plasmid pLC2 (Chen, L., Anton, M. and Graham, F. L., "Production and characterization of human 293 cell lines expressing the site-specific recombinase Cre," Somat. Cell and Molec. Genet. 22:477–488, 1996), as a 2175 bp BglII fragment which was end-modified with Klenow DNA polymerase and inserted into the EheI site of pCA36loxΔ to generate pCA36loxΔCreR and pCA36loxΔCreT. The plasmid pCA35loxΔCreITR was constructed by replacing the 1402 bp ScaI/KpnI fragment in pCA36loxΔCreT with the 2753 bp ScaI/KpnI fragment from the plasmid pRP1029. Plasmid pCA35loxΔCreITR contains ITR junctions which are known to be functionally capable of generating replicating linear Ad DNA molecules (Graham, F. L., "Covalently closed circles of human adenovirus DNA are infections," The EMBO J. 3, 2917–2922, 1984).

FIG. 8E provides a schematic representation of a cotransfection experiment wherein a pBHGloxΔE1,3 plasmid and a "Lox" shuttle plasmid expressing Cre are introduced into 293 cells in order to generate Ad expression vectors, without having to use cells which stably express Cre. This technique is applicable to any cell type suitable for Ad vector generation, including but not limited to 293 cells, and PER-C6 cells (Fallaux et al., Hum. Gene Ther. Sept. 1, 1998; 9(13):1909–17), 911 cells (Fallaux et al., Hum. Gene Ther. Jan. 20, 1996; 7(2):215–222), or other cells. A shuttle plasmid such as pCA35loxΔCreITR of FIG. 8D is also suitable for generation of an Ad vector. The efficiency of Ad vector rescue by cotransfection with pBHGloxΔE1,3 and various shuttle plasmids is summarized in Tables 3 and 4. It can be seen from the results in Table 4 that inclusion of an ITR junction in the shuttle plasmid increases the efficiency of rescue significantly. Thus, provision of an ITR junction is a preferred embodiment.

Insertion of an expression cassette encoding Cre recombinase in the shuttle plasmid is not meant to be limiting as one skilled in the art will appreciate that one could also insert a Cre cassette in the larger plasmid, pBHGloxΔE1,3. An example, not meant to be limiting, is diagrammed in FIG. 8F, which illustrates the construction of such a plasmid. It will be appreciated that the Cre expression cassette could be carried by either of the two plasmids used in the cotransfections such as that illustrated in FIG. 1, or by both of them, so that Cre is supplied at adequate levels in cotransfected 293 cells to catalyse efficient recombination between the lox sites of the cotransfected plasmids. Thus mention of the use of 293Cre cells or like cells expressing Cre recombinase is not meant to be limiting.

FIG. 8F demonstrates the construction of an Ad genomic plasmid encoding Cre. The plasmid pBHGloxΔ was constructed by collapsing pBHGloxΔE1,3 with SpeI and PshAI. The Cre expression cassette, taken from the plasmid pLC2 as a 2175 bp BglII fragment, was inserted into the BamHI site of pBHGloxΔ to generate pBHGloxΔCreR and pBHGloxΔCreL. The 1238 bp Bst1107I/PacI fragment from pBHGloxΔCreR and pBHGloxΔCreL was replaced with the 22380 bp Bst1107I/PacI fragment from pBHGloxΔE1,3 to generate pBHGloxCreR and pBHGloxCreL, respectively.

EXAMPLE 8

Rescue of Foreign DNA and Mutations into any Desired Location in the Adenoviral Genome The above examples illustrating rescue of foreign DNA into the E1 region of Ad vectors are not meant to be limiting. It will be appreciated by those skilled in the art that one could equally follow the instructions outlined above to construct similar plasmids for the rescue of insertions or mutations or deletions into E1 or other regions of the viral genome. For example, not meant to be limiting, one could construct a series of analogous plasmids suitable for rescue of fiber mutations into the viral genome or for rescue of foreign DNA inserts in the E3 region of the viral genome into infectious virus. An example, not meant to be limiting, is provided in FIG. 9A, which is a diagrammatic representation of a method for rescuing fiber mutations into infectious virus using Cre-loxP recombination. Cotransfection of 293Cre cells with pFG173lox and a shuttle plasmid containing a loxP site 5' of the fiber gene results in site-specific recombination between the lox sites and rescue into infectious virus of the adenoviral sequences of the shuttle, which sequences may optionally contain a mutated fiber gene.

FIG. 9B is a diagrammatic representation of a method for constructing a plasmid containing a lox site and ampicillin resistance gene substituting for the fiber gene. Starting with a plasmid such as pAB14lox, construction of which is described in FIG. 14, the DNA sequences between the Cla I site and the Blp I site containing fiber are substituted with a DNA segment containing the ampicillin resistance gene and a plasmid origin of DNA replication (which may optionally be obtained by restriction endonuclease digestion of an ampicillin resistant plasmid such as pCA14 (Microbix Biosystems)).

FIG. 9C is a diagrammatic representation of a method for combining the plasmid of FIG. 9B with pFG173 to produce pFG173 lox for rescuing fiber mutations into infectious virus using Cre-lox recombination. The plasmid pAB 14loxΔ illustrated in FIG. 9B comprises Ad sequences 3' of fiber to mu 100. The plasmid additionally contains viral DNA sequences 5' of fiber, but has all of the fiber coding sequences deleted and substituted with a plasmid origin of DNA replication and an antibiotic resistance gene, such as for ampicillin resistance. Sequences from pAB14loxΔ can be recombined with pFG173 (Microbix Biosystems) by homologous recombination in *E. coli* (Chartier C, Degryse E, Gantzer M, Dieterle A, Pavirani A, Mehtali M., "Efficient generation of recombinant adenovirus vectors by homologous recombination in *Escherichia coli*," J Virol July 1996; 70(7):4805–4810). The resulting plasmid, pFG173lox, has a deletion of sequences comprising all of the fiber gene or optionally part of the fiber gene or optionally all or part of E4 or optionally a deletion of all or part of both fiber and E4, and is consequently unable to produce infectious virus following transfection of cells. However, on recombination with a plasmid such as pFG23dX1lox or a similar plasmid, infectious virus can be readily generated, as illustrated in FIG. 9A. Said recombination can be efficiently catalysed by Cre recombinase, if pFG173lox and pFG23dX1lox are cotransfected into 293Cre cells or similar host cells expressing Cre recombinase.

Construction of plasmids suitable for rescue of fiber or E4 gene mutations or deletions or substitutions can be readily accomplished by one skilled in the art based on the present disclosure. An example, not meant to be limiting, of the construction of one such plasmid is illustrated in FIG. 10, which is a diagrammatic representation of a plasmid containing the right approximately 40% of the virus genome, wherein a lox P site has been inserted near the 5' end of the fiber gene. PFG23dX1 contains the right approximately 40% of the Ad 5 genome from nt 21563 (mu 60) to approximately the right end of the genome (mu 100) cloned into the BamH I site of pBR322 and additionally has a deletion of Ad5 sequences from 28593 to 30471, comprising most of E3 (Haj-Ahmad, Y. and Graham, F. L., "Development of a helper independent human adenovirus vector and its use in the transfer of the Herpes Simplex Virus thymidine kinase gene," J. Virol. 57, 267–274, 1986). PFG23dX1 was digested with XbaI and a synthetic oligonucleotide (SEQ ID NO:5 and SEQ ID NO:6; AB6920/AB6921, FIG. 3) containing a loxP site was inserted. The resulting plasmid, pFG23dX1lox, can be used for generation of infectious virus by cotransfection of 293Cre cells with a plasmid such as pFG173lox (FIG. 9A). Optionally, viral genes, such as those encoding fiber or genes of E4 can be mutated in pFG23dX1lox and the resulting mutations rescued into virus. Because Ad sequences 5' of the lox site (counterclockwise in the diagram) are not necessary when Cre-mediated site specific, rather than homologous, recombination is used to generate infectious virus, viral sequences between a unique Bst 11071 site and a BsiW1 site immediately 5' of the lox P site were deleted to generate pFG23dX1loxc.

One skilled in the art would appreciate, based on the instant disclosure, that just as Cre recombinase may be provided by inserting a Cre expression cassette in one or another or both of the cotransfecting plasmids to facilitate recombination between plasmids designed to rescue mutations or insertions in E1, similarly, one may insert said expression cassette into either or both of the plasmids to be recombined as diagrammed in FIG. 9A so that site specific recombination can be achieved in host cells that do not express the recombinase constitutively. In a preferred embodiment, the shuttle plasmid thus modified would be further modified to contain a junction of ITRs as the results shown in Table 4 indicate that said junction results in a significant improvement in efficiency of virus production. As in the examples illustrated in FIGS. 8c and 8e, said plasmids would most often be designed so that the Cre expression cassette would not be rescued into the infectious viral genomes that are thus generated.

Examples illustrating rescue of mutations into infectious virus are not meant to be limiting as one skilled in the art could readily appreciate that the methods described herein are equally employed to rescue insertions of foreign DNA into the viral genome. An example of a suitable plasmid that is readily constructed is pFG23dX1LacZlox. FIG. 11A is a diagrammatic representation of said plasmid wherein a foreign DNA, such as a gene encoding bacterial lacZ, is inserted between the lox P site and the fiber gene. In this example, not meant to be limiting, an expression cassette encoding β-galactosidase is inserted into the Cla I site adjacent to the loxP of pFG23dX1lox (FIG. 10) for subsequent rescue into infectious virus by the method illustrated in FIG. 9A. It will be appreciated by those skilled in the art that other foreign DNAs could readily be rescued into infectious virus genomes by the methods illustrated above. Said foreign DNA segment could be a separate expression cassette or a fusion of sequences encoding peptide sequences to sequences encoding fiber, said peptide sequences representing, for example, a ligand to a cell surface receptor such that the rescued virus expressing a modified fiber would have novel and useful cell attachment properties. This example is not meant to be limiting as it will be appreciated by one skilled in the art that lox P sites can readily be introduced into other positions of the viral DNA for substitution of other virion genes with mutated counterparts.

These examples are not meant to be limiting as one could construct a plasmid similar to pFG173lox from which other viral genes have been deleted such as, for example, those of E1 such that the resulting viruses generated by Cre-mediated recombination are E1 deleted viruses.

EXAMPLE 9

Use of Engineered Adenoviruses Produced According to this Invention

The use of the two plasmid system in combination with Cre-mediated site-specific recombination is not meant to be limiting as one skilled in the art will readily appreciate that, as taught for the generation of viruses carrying E1 mutations, deletions and insertions, one could employ viral DNA isolated from suitably engineered viruses for the manipulation of the viral genome by Cre-mediated recombination. For example, as illustrated in FIGS. 12 and 13, 293Cre cells are cotransfected with DNA extracted from a virus containing a floxed fiber gene in such a way as to retain either or both terminal proteins, TP. Optionally the DNA is digested with restriction enzymes that cut sequences between the lox sites prior to cotransfections. It will be apparent to those skilled in the art, based on the instant disclosure, that the right most lox site is not needed and may optionally be deleted or omitted if DNA-TP is to be cut with restriction enzymes prior to cotransfection. As with the two plasmid method, the method of FIGS. 12 and 13 is employed to rescue mutations in the fiber gene or in E4 or to rescue foreign DNA inserts as in FIG. 13.

To confirm that it is possible to insert into the adenovirus genome lox sites that flank a gene such as that encoding fiber, the plasmid shown in FIG. 14, called pAB14flox, was constructed. This plasmid contains a lox site inserted into the unique Blp I site in pAB14, which is located between the 3' terminus of the fiber gene and the coding regions of E4 genes. A second lox site was inserted into the XbaI site upstream of fiber. PAB14flox (fiber flanked by lox sites) was rescued into infectious virus by cotransfection with pFG173 (described in Hanke, T., Graham, F. L., V. Lulitanond and D. C. Johnson, "Herpes simplex virus IgG Fc receptors induced using recombinant adenovirus vectors expressing glycoproteins E and I," Virology 177: 437–444, 1990. PFG173 is available from Microbix Biosystems) as illustrated in FIG. 15, to produce Adfloxfiber. In two experiments, 293 cells were cotransfected with pAB14flox and pFG173, and two plaque isolates were obtained in each experiment (from 8 cotransfected dishes of 293 cells in experiment 1, and from 4 dishes in experiment 2). Two plaques were expanded and analyzed and shown to have the expected DNA structure as illustrated in FIG. 15.

Upon transfection of 293Cre cells with DNA-TP complex of an Ad virus, such as Adfloxfibre-TP depicted in FIG. 15, said floxed fiber gene is excised by site-specific recombination between similarly oriented lox P sites, resulting in noninfectious viral DNA (as fiber is an essential component of the virion) as illustrated in FIG. 12. Cotransfection of said 293Cre cells with a plasmid containing a single lox P site upstream of fiber, such as pFG23dX1lox, optionally carrying a fiber or E4 gene mutation or insertion of foreign DNA, results in high-efficiency site-specific recombination between the plasmid and viral DNA and results in a virus whose fiber gene is derived from the plasmid as illustrated in FIG. 12 or FIG. 13. Therefore, it will be readily appreciated by one skilled in the art that mutations, deletions or other modifications engineered in and around the fiber gene of the plasmid, are rescued into the infectious virus genome. As an example, not meant to be limiting, the combination of plasmid, virus DNA and recombinase as illustrated in FIGS. 12 and 13 leads to high-efficiency substitution of wild-type fiber with modified fiber genes for production of mutant viruses whose virion capsids contain altered fiber.

As a further example of the utility of this approach, a foreign DNA segment is introduced into a plasmid, such as pFG23dX1lox, between the lox site and the coding sequences of fiber, such that said foreign DNA segment is rescued into virus by cotransfection of 293Cre cells with DNA prepared from Adlox2fiber (FIG. 13). As in the examples described previously for use of the two plasmid system, said foreign DNA segment could be a separate expression cassette or could be a fusion of peptide sequences such as a ligand to a cell surface receptor.

Table 5 provides results documenting the efficiency with which Cre mediated recombination can be used to generate infectious virus by cotransfection of 293Cre cells as illustrated in FIG. 9A. It is apparent that the efficiency of rescue is comparable to that shown in Tables 1 and 2 and is several fold higher than the efficiency of homologous recombination (pFG173+pFG23dX1).

EXAMPLE 10

Use of Alternate Adenoviral Vector Systems According to this Invention

Those skilled in the art will recognize, based on the instant disclosure, that in the system described herein according to FIG. 8C, the left most lox site is not essential when the viral DNA is digested with enzymes such as those depicted, namely AsuII and/or SwaI. It will also be recognized that enhanced rescue of mutations or inserts into the viral genome by cotransfection of cells with a plasmid plus a viral DNA fragment with TP does not require a TP at both ends so the large viral DNA fragment generated by AsuII and/or SwaI digestion and having a TP at the right end only is sufficient for this system to operate efficiently. Similarly in the systems disclosed according to FIGS. 12 and 13, only the lox site 5' of fiber is necessary if the viral DNA-TP is cleaved with one or more enzymes that cut to the right, e.g. in fiber or in E4. If there are not naturally occurring restriction sites suitable for this purpose, such sites may easily be engineered by those of ordinary skill in the art, based on the present disclosure. For example we have identified a Blp I site between the 3' end of fiber and the coding sequences for E4 that can be used to insert a synthetic DNA. As illustrated in FIG. 14 we inserted a lox DNA sequence into this site but we could easily have introduced DNA containing a restriction endonuclease site that is not present elsewhere in the viral genome, and said restriction site could be rescued into an infectious virus as illustrated in FIG. 15.

It will further be recognized, based on the present disclosure, that the combination of Cre-lox with the two plasmid system will have widest application because of its simplicity: only readily prepared plasmid DNA is required, no restriction enzyme digestions are required, no possible background of parental viruses has to be contended with, and the system is more than adequately efficient for most purposes. Nonetheless, when enhanced levels of infectivity are required, utilization of the methods disclosed herein for use of viral DNA incorporating bound terminal protein may also benefit through combination with the site-specific recombination techniques taught herein.

EXAMPLE 11

Use of Head-to-Head ITR Junctions to Enhance the Efficiency of Recombination by Homologous Recombination or Site-specific Recombination As noted above in this invention disclosure, the efficiency of rescue of genes into Ad recombinant vectors can be markedly enhanced by engineering the plasmids so that recombination is mediated by Cre recombinase rather than by homologous recombination. Construction of Ad vectors by Cre-mediated recombination between two plasmids cotransfected into 293Cre4 cells is highly efficient. Unfortunately, this system requires E1-complementing cell lines expressing Cre, which are currently not as widely available as are the parental 293 cells. This method would be more widely applicable if high efficiency Cre-mediated vector rescue could be achieved using the ubiquitous 293 cells or other E1-complementing cell lines. Therefore, we modified the system by introducing a Cre expression cassette into the shuttle plasmid pCA36loxΔ to generate pCA36loxΔCreR and pCA36loxΔCreT (FIG. 8D). The plasmids were designed so that the Cre cassette is not incorporated into the recombinant vector after recombination owing to its location within the plasmids, but should permit transient Cre expression following cotransfection thus abrogating the need for a Cre-expressing cell line. The validity of this approach was tested by comparing the vector rescue efficiencies following cotransfection of 293 cells with pBHGloxΔE1,3 and shuttle plasmids with or without the Cre expression cassette. The results of typical experiments are presented in Table 3 and Table 6.

In Table 6 the numbers of plaques generated following cotransfection of 293 cells with pBHGloxΔE1,3 and pCA36 or pCA36lox were similar and are typical of the efficiency of vector rescue by homologous recombination. No plaques were generated with pCA36loxΔ since all Ad sequences downstream of the loxP site have been deleted to virtually preclude vector rescue by homologous recombination. In contrast to pCA36loxΔ, pCA35loxΔCreT was able to mediate vector rescue indicating that Cre-mediated vector rescue could be achieved using 293 cells by including a Cre-expression cassette in the shuttle plasmids. Similar numbers of plaques were generated with pCA36loxΔCreR (Table 3). However, the efficiencies of vector rescue using pCA36loxΔCreT or pCA36loxΔCreR were considerably lower than that obtained using 293Cre4 cells (Table 3) suggesting that constitutive Cre expression from 293Cre4 cells resulted in more efficient Cre-mediated vector rescue than was obtained via transient Cre-expression from the transfected shuttle plasmid.

Although we had no direct measure of Cre levels in 293Cre4 cells compared to 293 cells transiently transfected with pCA36loxΔCreR, it was possible that Cre recombinase levels in 293Cre4 cells were higher than levels in transfected 293 cells. Therefore we asked whether it might be possible to increase the efficiency of Cre-mediated vector rescue by increasing the copy number of the shuttle plasmid. To do this we replaced the single ITR junction in pCA36loxΔCreT with a head-to-head ITR junction to generate pCA35loxΔCreITR (FIG. 8D). The rationale for this modification was based on the observation that an ITR junction can serve as an efficient origin of Ad DNA replication resulting in linearization and, presumably, amplification of plasmid DNA (Graham, 1984 EMBO J. 3:2971). Therefore, following cotransfection of 293 cells with pBHGloxΔE1,3, which also bears an ITR junction as well as encoding all trans-acting factors required for Ad DNA replication, pCA35loxCreITR was expected to linearize and replicate, which we anticipated should also result in increased Cre expression (more copies of the expression cassette). The validity of this approach was tested by comparing the vector rescue efficiencies following cotransfection of 293 cells with pBHGloxΔE1,3 plus various shuttle plasmids. The results of a typical experiment are presented in Table 4. The numbers of plaques generated using pCA36lox and pCA36loxΔCreT were consistent with the results presented in Table 6. In contrast to the results with pCA36loxΔCreT, the number of plaques generated with pCA35loxΔCreITR was ~10-fold higher (Table 4) indicating that replacement of the single ITR with an ITR junction resulted in a significant increase in the efficiency of Cre-mediated vector rescue using 293 cells.

Figure 2B:
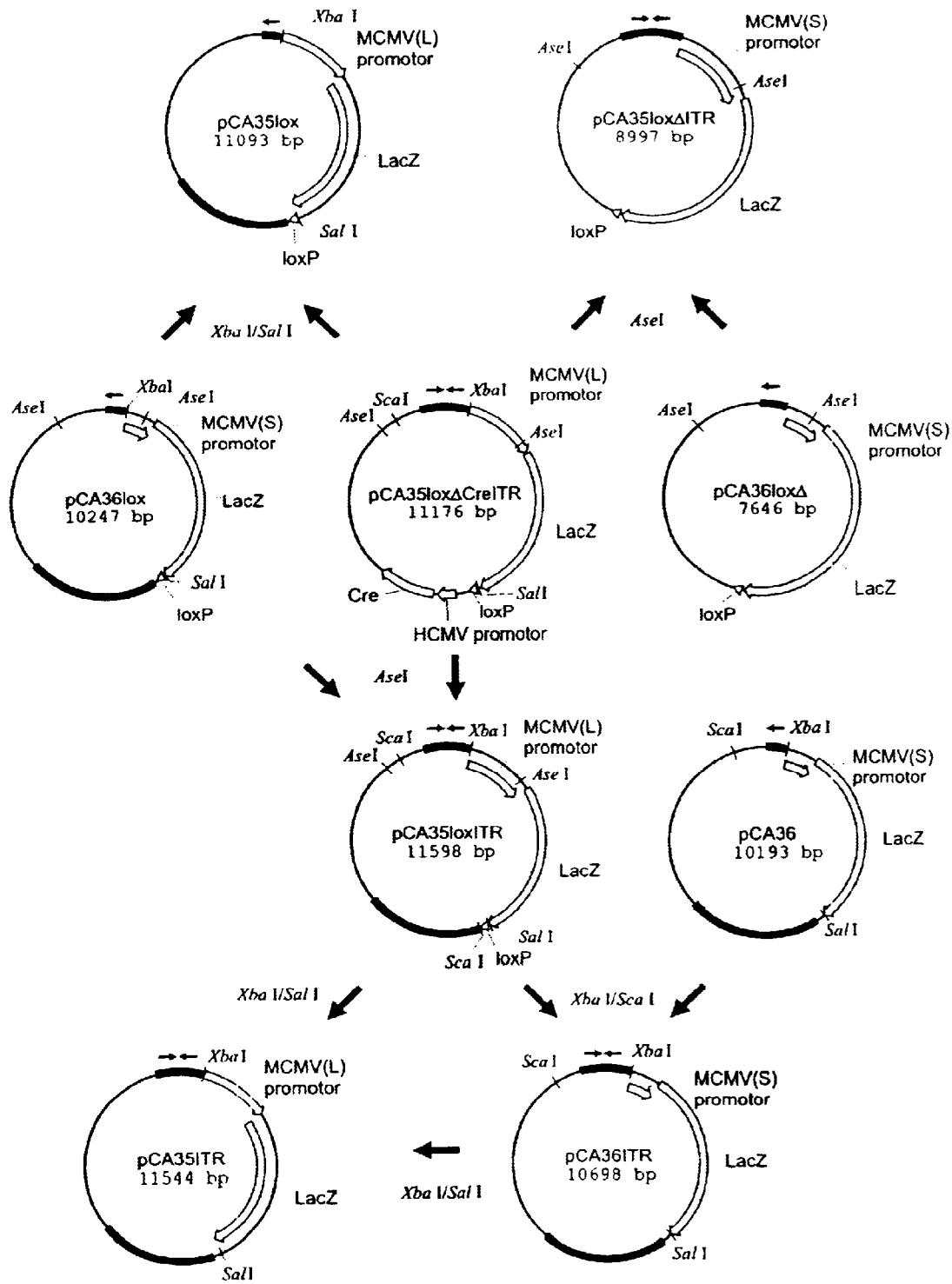
FIG. 2B. Construction of shuttle plasmids. The plasmid pCA35lox was constructed by replacing the XbaI/SalI fragment containing the LacZ expression cassette under the control of the short MCMV promotor in pCA36lox with the XbaI/SalI fragment containing the LacZ expression cassette under the control of the long MCMV promotor from pCA35loxΔCreITR. The plasmid pCA35loxΔITR was constructed by replacing the AseI fragment bearing the single left end ITR in pCA36loxΔ with the AseI fragment bearing an ITR junction from pCA35loxΔCreITR. The plasmid pCA35loxITR was constructed by replacing the AseI fragment bearing the single left end ITR in pCA36lox with the AseI fragment bearing an ITR junction from pCA35loxΔCreITR. The plasmid pCA36ITR was constructed by replacing the ScaI/XbaI fragment bearing the single left end ITR in pCA36 with the ScaI/XbaI fragment bearing an ITR junction from pCA35loxITR. The plasmid pCA35ITR was generated by replacing the XbaI/SalI fragment containing the LacZ expression cassette under the control of the short MCMV promotor in pCA36ITR with the XbaI/SalI fragment containing the LacZ expression cassette under the control of the long MCMV promotor from pCA35loxITR. Thin black lines represent bacterial plasmid sequences and thick black lines represent Ad sequences. The position and orientation of loxP sites and Ad ITR are indicated by white triangles and small horizontal arrows, respectively. Plasmids are not drawn to scale and only the relevant restriction enzyme sites are shown.

The results presented in Table 4 indicated that a shuttle plasmid containing a Cre expression cassette and an ITR junction resulted in very significantly improved rescue efficiency compared to a similar plasmid that had only a single ITR. However, in the absence of direct measurements of Cre protein in transfected cells we could not conclude that this was due to enhanced Cre expression or due to some other mechanism. As a control experiment we constructed a shuttle plasmid without the Cre cassette and containing an ITR junction for comparison with a similar plasmid having a single ITR (FIG. 2B). Virus rescue in this experiment (Table 7) was dependent on homologous rather than Cre-mediated recombination since none of the plasmids used contained lox sites and no Cre was expressed in the cotransfected cells. Surprisingly, the shuttle plasmid with an ITR junction gave about 10 fold higher efficiency of recombinant virus rescue compared to an otherwise identical plasmid with a single ITR. Thus the improved rescue using pCA35loxCreITR compared to pCA36loxΔCreT may be entirely due to the use of an ITR junction rather than to increased levels of Cre. Consequently, recombinant virus rescue using the two plasmid approach is markedly improved (approximately 10 fold greater efficiency) by incorporation of ITR junctions into the shuttle plasmids. This allows either for greater numbers of plaques to be produced or allows for vector rescue to be achieved using lower concentrations of plasmid DNA in the cotransfections or fewer numbers of cells or both.

Figure 4D:
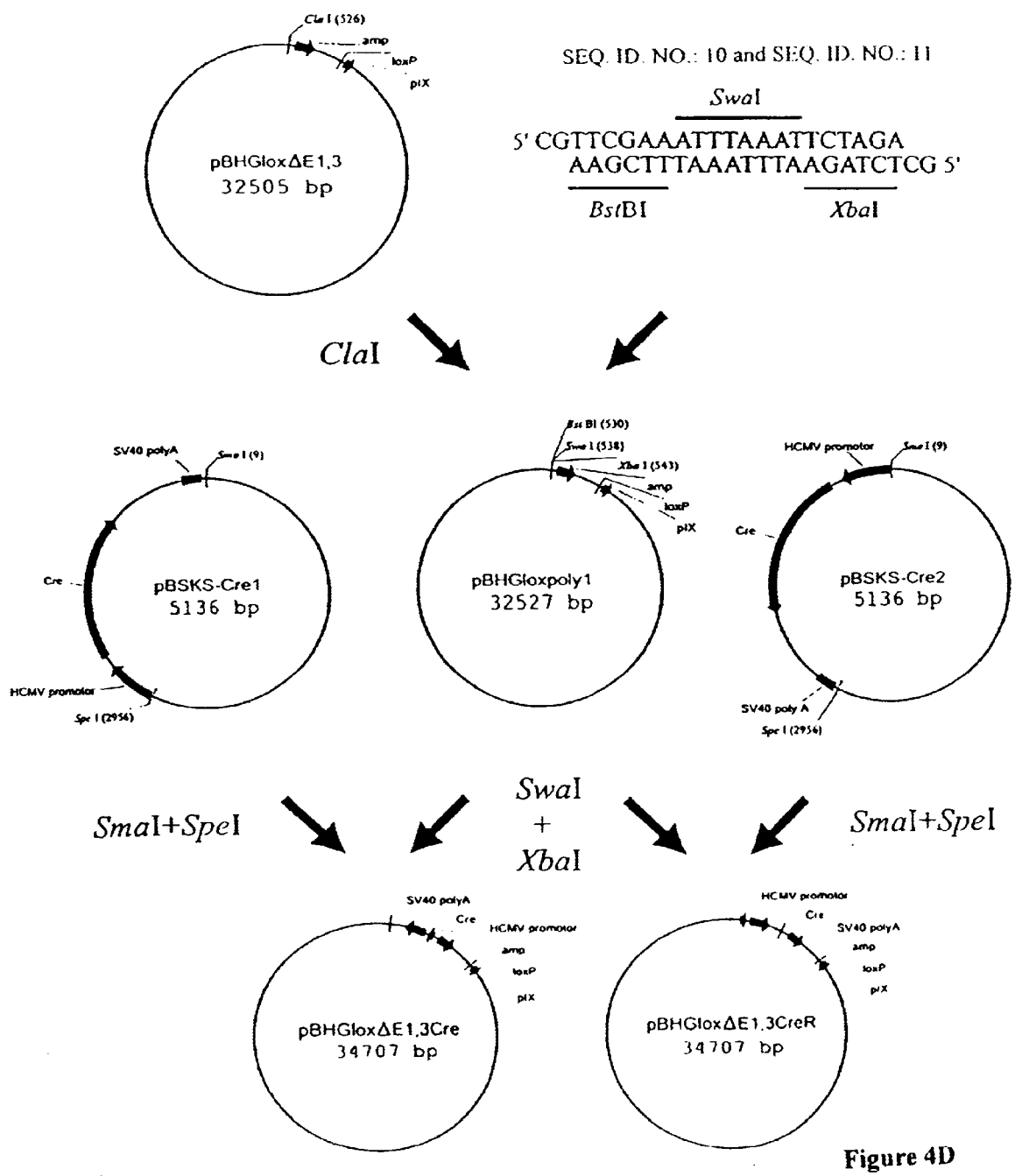
FIG. 4D illustrates the construction of Ad genomic plasmids encoding Cre. The plasmid pBHGloxpoly1 was constructed by insertion of an oligonucleotide pair, SEQ ID NO:10 and SEQ ID NO:11, containing BstB I, Xba I and Swa I sites and Cla I compatible ends into the Cla I site of pBHGloxΔE1,3. The Cre expression cassettes, taken from the pBSKS-Cre1 or pBSKS-Cre2 as a Sma I-Spe I fragment fragment, were inserted into Swa I, Xba I digested pBHGloxpoly1 as illustrated to generate pBHGloxΔE1,3Cre and pBHGloxΔE1,3CreR.

Expression of Cre can be from the cotransfected cells, e.g. through use of 293Cre4 cells or the like, or by expression from Cre cassettes cloned in one or the other of the cotransfected plasmids. For example, not meant to be limiting, a Cre cassette can be inserted into the genomic plasmid such as one based on pBHGloxΔE1,3. An example of one method of construction of such plasmids is illustrated in FIG. 4D wherein a Cre expression cassette was inserted in either of two orientations into a pBHG10 derivative, pBHGloxΔE1,3, to generate pBHGloxΔE1,3Cre and pBHGloxΔE1,3CreR. Combining use of ITR junctions with the Cre-mediated recombination system of AdVec10 improves the efficiency of recombinant virus production by at least 100 fold over the original two plasmid method (Tables 8–13). For example, the data presented in Table 8 show that cotransfection of 293 cells with the genomic plasmid, pBHGloxΔF1,3, plus the shuttle plasmid pCA36lox did not produce any plaques, in this experiment, because of the low efficiency of rescue by homologous recombination when the shuttle plasmid contains only a single ITR. In contrast addition of an ITR junction resulted in relatively high efficiency of rescue (15 plaques/dish), and cotransfection of 293Cre cells with pCA36lox+pBHGloxΔE1,3 (which allows for rescue by Cre mediated recombination) resulted in 11 plaques/dish. The best efficiencies were obtained by cotransfecting 293Cre cells with the shuttle plasmid containing an ITR junction: 113 plaques/dish. That recombination was due to action of Cre can be seen from the results obtained when the shuttles are deleted of Ad sequences rightward of the expression cassette thus preventing homologous recombination. In this case, no plaques were obtained following cotransfection of 293 cells but over a hundred plaques/dish were obtained in 293Cre cells when the plasmid contained an ITR junction. Thus a preferred embodiment of the invention is the combination of site specific recombination with use of shuttle plasmids that contain ITR junctions in addition to lox sites. Nonetheless, those skilled in the art will appreciate that even the simple addition of an ITR junction to the shuttle plasmids used in homolgous recombinations results in a marked improvement in rescue efficiency over use of plasmids containing a single ITR. Thus when use of a site specific recombinase might be impractical or undesirable, use of shuttle plasmids with ITR junctions provides a simple and relatively efficient means to construct Ad vectors containing foreign DNA insertions.

The results presented in Tables 9 and 10 demonstrate that Cre recombinase can be provided by the cotransfecting shuttle plasmid, for example pCA35loxΔCreITR, or by the cotransfected host cells, e.g. 293Cre cells. In these and several additional experiments, plaques were isolated, expanded on 293 cells and analyzed for viral DNA structure and for expression of β-galactosidase from the expression cassette cloned in pCA35 and pCA36 and derivative plasmids. Over 60 independent plaque isolates were analyzed in this way and in every case the viral DNA structure was that predicted for recombinant viral vectors generated by recombination between the genomic plasmid DNA and the shuttle plasmid DNA and all recombinant viruses expressed β-galactosidase. Thus the methods described herein provide for accurate and reliable construction of Ad vectors containing and expressing a foreign DNA.

The results presented in Tables 11 and 12 indicate that for high efficiency rescue the Cre recombinase can be expressed by the recipient host cells, such as 293Cre4 cells, or by the shuttle plasmid, such as pCA35loxΔCreITR, or by the genomic plasmid such as pBHGloxΔE1,3Cre or by a combination of these. It will be seen by those skilled in the art that the result of recombination between said plasmids is a virus that does not contain the Cre expression cassette. The results also provide further evidence for the importance of providing an ITR junction on the shuttle plasmid whether rescue is via homologous recombination or via site specific recombination.

Thus, as is amply illustrated by the results of numerous cotransfection experiments presented in Tables 8–13, the Cre recombinase may be expressed from either of the cotransfecting plasmids or from the host cells, such as 293Cre4 cells. The efficiency of rescue of recombinant viruses can be remarkably high, in some experiments, such as those illustrated by Tables 9 and 10, resulting in too many plaques to be countable. Although a Cre cassette may be in either the genomic plasmid or in the shuttle plasmid, if Cre expression is provided by the cotransfected plasmid DNA rather than from the transfected host cells, it is a preferred embodiment of the invention that the Cre cassette be present in the genomic plasmid for two reasons: firstly, the shuttle plasmids may then be as small as possible with as many cloning sites as possible for ease of insertion of foreign DNAs, and secondly, the results illustrated in Tables 11–13 suggest that the efficiency of rescue is greater for those transfections of 293 cells in which Cre recombinase is provided by the genomic plasmid, specifically the plasmid pBHGloxΔE1,3Cre.

Figure 5E:
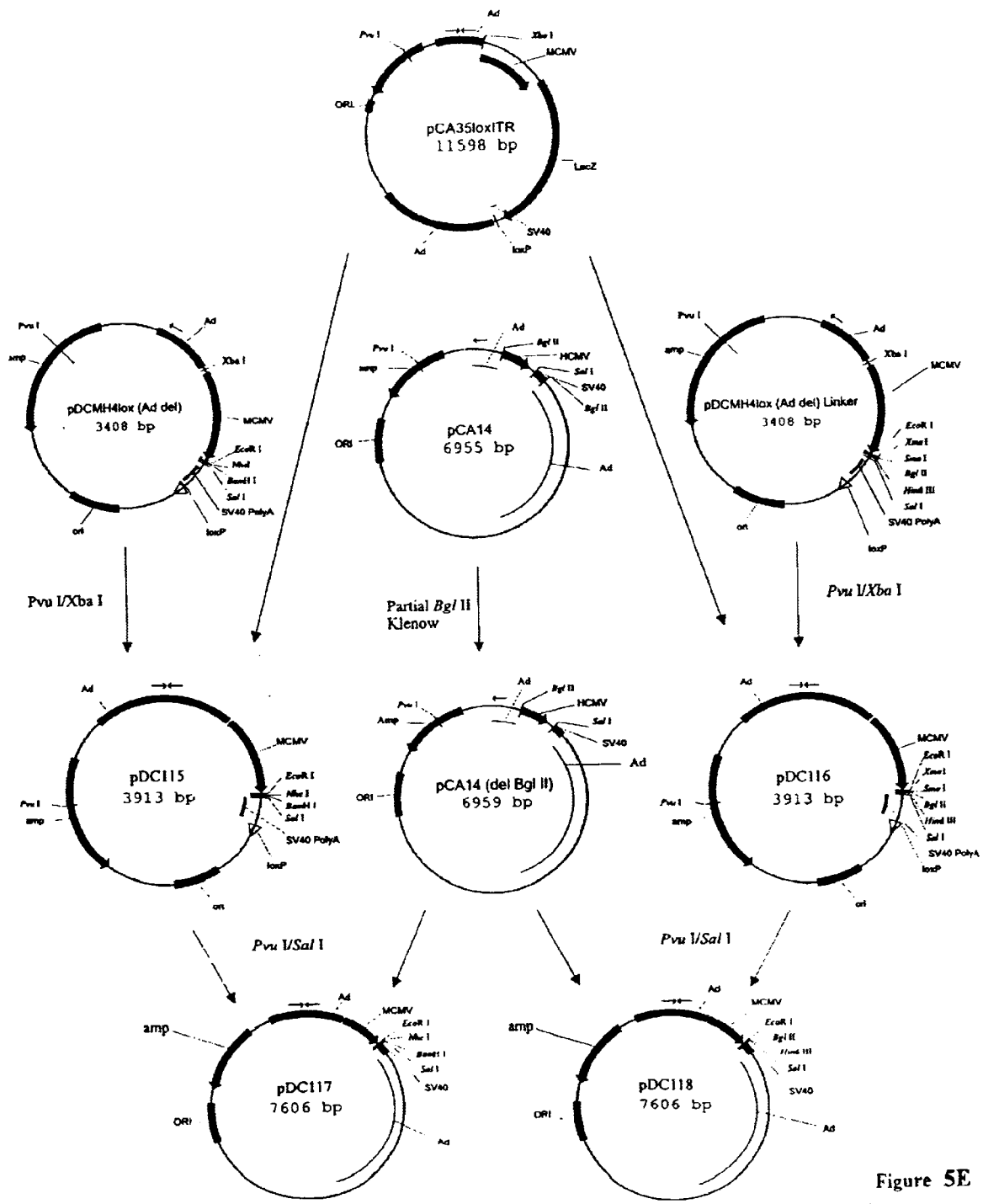
FIG. 5E. Construction of additional shuttle plasmids. The plasmids pDC115 and pDC116 were generated by replacing the Pvu I/Xba I fragment of pDCMH4lox(Addel) and pDCMH4lox(Addel)linker with a similar Pvu I/Xba I ITR junction containing fragment from pCA35loxITR. The resulting plasmids contain an ITR junction instead of a single left end ITR. The plasmids pDC117 and pDC118 were produced by inserting a Pvu I/Sal I fragment from pCA14(del Bgl II) into pDC115 and pDC116 digested with Pvu I/Sal I. The plasmids pDC117 and pDC118 have no loxP site, but they do contain Ad sequences for virus rescue by homologous recombination.

Those skilled in the art will appreciate that many different shuttle plasmids can be constructed and used to generate recombinant viral vectors by the methods outlined above. As an example, not meant to be limiting, the series of shuttle plasmids illustrated in FIGS. 5a, 5b and 5d were constructed from readily available plasmids using methods commonly employed by those skilled in the art. Among the shuttle plasmids constructed are plasmids such as pΔE1Sp1AloxITR(MCS) and pΔE1Sp1BloxITR(MCS) (FIG. 5a) that have ITR junctions, polycloning sites (MCS), lox sites and Ad sequences for homologous recombination. Said plasmids can be used for virus rescue by either homologous or site specific recombination by the methods outlined above. Other useful plasmids are pDC111–114 (FIG. 5C) also having ITR junctions, polycloning sites, lox sites, or having ITR junctions and Ad sequences for homologous recombination (pDC113 and pDC114) if Cre mediated recombination is not required or not desirable. FIG. 5E and FIG. 6A illustrate the construction of several shuttle plasmids that have a promoter (the murine cytomegalovirus immediate early gene promoter, MCMV), a polycloning region, and polyadenylation signal (SV40) for insertion and expression of cDNAs in Ad vectors. These plasmids provide for considerable versatility in vector isolation. For example, pDC115 and pDC116 (FIG. 5E), having lox sites but no Ad sequences rightward of the lox sites, can be used for virus rescue by cotransfection of cells in the presence of Cre recombinase. Plasmids pDC117 and 118 on the other hand, having no lox sites but having Ad sequences for homologous recombination, can be used for recombinant virus isolation in the absence of Cre recombinase, and the efficiency of rescue is high due to the presence of ITR junctions.

The use of shuttle plasmids with ITR junctions and the use of Cre mediated site specific recombination and the combination of these two improvements significantly increase the efficiency and reliability of the two plasmid system for Ad vector construction. These new methods will permit the production of expression vector libraries comprising large numbers of recombinant adenovirus vectors capable of expressing different cDNAs for analysis of protein function in mammalian cells and in animals. Vectors produced by the methods disclosed herein can also find use as recombinant viral vaccines and in gene therapy.

The enhanced efficiency of recombinant virus isolation using shuttle plasmids containing ITR junctions is not limited to production of vectors with insertions or substitutions or mutations in the E1 region. One skilled in the art will recognize that the ease and efficiency of engineering alterations into other regions of the virus genome would be similarly enhanced by introduction of ITR junctions in place of single ITRs in plasmids containing Ad sequences from the right end of the genome. For example, not meant to be limiting, in such plasmids as pFG23dX1lox or pFG23dX1LacZlox illustrated in FIGS. 10 and 11 the single ITR could be readily substituted with ITR junctions to improve the efficiency of rescue of, for example, fiber mutations or foreign DNA inserts in cotransfected cells by methods such as that diagrammed in FIG. 11B. For example, an ITR junction from pBHG10 was introduced into pFG23dX1lox to produce pFG23dX1loxITR. Cotransfection of 293Cre4 cells with pFG173lox and pFG23dX1loxITR resulted in approximately 50–60 plaques per dish, about 5–10 fold higher than is routinely obtained with pFG23dX1lox. Furthermore, the virus rescues illustrated in FIGS. 9, 12 and 13 would be similarly increased in efficiency if the second plasmid were engineered to contain ITR junctions such as those illustrated for pFG23dX1lox ITR in FIG. 11B.

Accordingly, as can be understood from the foregoing disclosure, when implementing hthITR junctions according to this invention, recombination may be via site specific mechanisms, for example Cre-mediated recombination as indicated in FIG. 11B, or by homologous recombination if the cotransfecting plasmids are constructed so as to have overlapping Ad sequences that can allow for recombination to produce an infectious viral genome.

TABLE 1

Cotransfections on 293 and 293Cre4 cells for rescue of LacZ vectors (±loxP)

| Plasmid combo | μg DNA | Plaques/dish (293 cells) | (Totals) | Plaques/dish (293Cre4 cells) | (Totals) |
|---|---|---|---|---|---|
| pCA36:pBHG10 | 5:5 | 0, 0, 0, 0 | | 0, 1, 2, 0 | |
| | 5:10 | 0, 0, 0, 1 | | 1, 0, 0, 0 | |
| | 10:10 | 2, 0, 1, 1 | | 1, 2, 0, 0 | |
| | | | (5) | | (7) |
| pCA36:pBHGloxΔE1,3 | 5:5 | 0, 0, 0, 1 | | 0, 0, 0, 0 | |
| | 5:10 | 0, 0, 0, 1 | | 0, 0, 0, 0 | |
| | 10:10 | 0, 0, 2, 1 | | 0, 0, 0, 0 | |
| | | | (5) | | (0) |
| pCA36lox:pBHG10 | 5:5 | 1, 3, 1, 0 | | 0, 1, 0, 1 | |
| | 5:10 | 0, 1, 0, 0 | | 0, 0, 1, 2 | |
| | 10:10 | 0, 0, 0, 0 | | 0, 1, 1, 0 | |
| | | | (6) | | (7) |
| pCA36lox:pBHGloxΔE1,3 | 5:5 | 1, 0, 0, 1 | | 15, 14, 20, 20 | |
| | 5:10 | 0, 0, 0, 0 | | 11, 15, 12, 16 | |
| | 10:10 | 0, 0, 1, 1 | | 18, 9, 10, 8 | |
| | | | (4) | | (168) |

TABLE 2

Cotransfections on 293 and 293Cre4 cells for rescue of LacZ Vectors (±loxP)

| Plasmid combo | μg DNA | Plaques/dish (293 cells) | (Totals) | Plaques/dish (293Cre4 cells) | (Totals) |
|---|---|---|---|---|---|
| pCA36:pBHGloxΔE1,3 | 5:5 | 1, 1, 2, 6, 2, 3 | (15) | 1, 1, 2, 1, 2, 3 | (10) |
| pCA36lox:pBHGloxΔE1,3 | 5:5 | 1, 2, 2, 2, 2, 1 | (10) | 41, 44, 41, 41, 44, 31 | (242) |
| pCA36loxΔ:pBHGloxΔE1,3 | 5:5 | 0, 0, 0, 0, 0, 0 | (0) | 41, 36, 55, 34, 24, 40 | (230) |
| FG140 | 1 | 72, 72 | | 150, 115 | |

TABLE 3

Efficiency of Ad vector rescue by cotransfection with pBHGloxΔE1,3 and various shuttle plasmids[a]

| Cell line | Shuttle plasmid | Plaques/dish | Average/dish |
|---|---|---|---|
| 293 | pCA36lox | 6, 2, 3, 3, 5 | 3.8 |
|  | pCA36loxΔ | 1, 4, 0, 0, 0 | 1.0 |
|  | pCA36loxΔCreR | 2, 2, 4, 3, 2 | 2.6 |
|  | pCA36loxΔCreT | 9, 4, 4, 7, 3 | 5.4 |
| 293Cre4 | pCA36loxΔ | 23, 28, 22, 28 | 25.3 |

[a]5 μg of all plasmids were used in cotransfections.

TABLE 4

Efficiency of Ad vector rescue by cotransfection of 293 cells with pBHGloxΔE1,3 and shuttle plasmids encoding Cre[a].

| Cell line | Shuttle plasmid | Plaques/dish | Average/dish |
|---|---|---|---|
| 293 | pCA36lox | 2, 3, 1, 0, 1 | 1.4 |
|  | pCA36loxΔ | 1, 0, 0, 0, 0 | 0.2 |
|  | pCA36loxΔCreT[b] | 3, 1, 5, 2, 4 | 3.0 |
|  | pCA35loxΔCreITR[b] | 21, 20, 42, 34, 40 | 31.4 |

[a]All cotransfections performed with 5 μg of the indicated shuttle plasmid and 5 μg of pBHGloxΔE1,3
[b]Plasmids illustrated in FIG. 8c.

TABLE 5

Efficiency of rescue of fibre and E4 genes into Ad by cotransfection with pFG173lox and pFG23lox[a]

| | | Number of plaques (average/dish) | |
|---|---|---|---|
| Plasmids | μg DNA | 293 cells | 293Cre4 cells |
| pFG173lox[b] : pFG23dX1loxc[c] | 5:5 | 0, 0, 0, 0 (0) | 33, 27, 39, 26 (31) |
|  | 2:2 | 0, 0, 0, 0 (0) | 9, 15, 10, 9 (11) |
| pFG173 : pFG23dX1 | 5:5 | 0, 0, 0, 0 (0) | 0, 0, 1 (0.3) |
| pFG140 | 1 | 95 | 93 |

[a]Cotransfections as diagrammed in FIG. 9
[b]Diagrammed in FIG. 9b
[c]Diagrammed in FIG. 10

TABLE 6

Recombinant virus rescue following cotransfection of 293 cells with shuttle plasmids with or without a Cre expression cassette

| Plasmid | Number of plaques/dish (average/dish) |
|---|---|
| pCA36 | 1, 0, 0, 0 (0.3) |
| pCA36lox | 1, 1, 1, 0 (0.8) |
| pCA36loxΔ | 0, 0, 0, 0 |
| pCA36loxΔCreT | 2, 1, 2, 2 (1.8) |
| pFG140 | 40, 31 (35.5) |

293 cells were cotransfected with 5 μg of pBHGloxΔE1,3 and 5 μg of the indicated shuttle plasmid or 1 μg of pFG140

TABLE 7

Efficiency of Ad vector rescue by cotransfection of 293 cells with pBHG10 and shuttle plasmids with a single ITR or an ITR junction

| Plasmid | μg of DNA/60 mm | # of Plaques | Average |
|---|---|---|---|
| pCA35:pBHG10 | 2:2 | 2, 0, 0, 1, 0, 2 | 0.83 |
|  | 5:5 | 2, 2, 2, 1 | 1.75 |
| pCA35ITR:pBHG10 | 2:2 | 19, 11, 14, 12 | 14 |
|  | 5:5 | 23, 23, 14, 17 | 19.25 |
| pFG140 | 1 | 96, 106 | 101 |

TABLE 8

Cotransfections on 293 and 293Cre4 cells for rescue of LacZ vectors (±lox, ±ITR junction, ±CRE)

| Shuttle Plasmid[a] | Plaques/dish (293 cells) | (Average) | Plaques/dish (293Cre4 cells) | (Average) |
|---|---|---|---|---|
| pCA36lox | 0, 0, 0, 0 | (0) | 13, 15, 3, 13 | (11) |
| pCA35loxITR | 8, 13, 21, 19 | (15) | 111, 131, 100, 130 | (113) |
| pCA36loxΔ | 0, 0, 0, 0 | (0) | 10, 8, 9, 12 | (10) |
| pCA35loxΔITR | 0, 0, 0, 0 | (0) | 91, 127, 141, 118 | (119) |
| pFG140[b] | 75 |  | 83 |  |

[a]All cotransfections 5 μg shuttle plasmid + 5 μg pBHGloxΔE1,3
[b]1 μg/dish

TABLE 9

Cotransfections on 293 and 293Cre4 cells for rescue of LacZ vectors (±lox, ±ITR junction, ±CRE)

| | | Number of plaques/dish (average/dish) | |
|---|---|---|---|
| Plasmids | μg DNA/dish | 293 cells | 293Cre4 cells |
| pCA36:pBHGloxΔE1,3 | 5:5 | ND | 0, 3 (1.5) |
| pCA36lox:pBHGloxΔE1,3 | 2:2 | ND | 9, 3 (6) |
|  | 5:5 | 2, 0, 0, 0 (0.5) | 30, 31, 30, 30 (30.25) |
| pCA35loxΔCreITR:pBHGloxΔE1,3 | 2:2 | ND | 71, 60, 56, 79 (66.5)* |
|  | 5:5 | 36 | 100, 96 (98) |
| pCA35loxΔITR:pBHGloxΔE1,3 | 2:2 | ND | 55, 64, 75, 63 (64.25)* |
|  | 5:5 | 0 | 120, 113 (116.5) |

TABLE 9-continued

Cotransfections on 293 and 293Cre4 cells for rescue of LacZ vectors (±lox, ±ITR junction, ±CRE)

| | | Number of plaques/dish (average/dish) | |
|---|---|---|---|
| Plasmids | µg DNA/dish | 293 cells | 293Cre4 cells |
| pCA35loxITR:pBHGloxΔE1,3 | 2:2 | ND | 53, 54, 61, 66 (58.5)* |
| | 5:5 | ND | 130, 126 (128) |
| pFG140 (DC) | 1 | 92 | 178 |
| pFG140 (CE) | 1 | 94 | 118 |

*5 plaques picked from each of these cotransfections and analyzed. All + for β-gal and all had predicted viral DNA structure

TABLE 10

Cotransfections on 293 and 293Cre4 cells for rescue of LacZ vectors (±lox, ±ITR junction, ±CRE)

| | | Number of plaques/dish (average/dish) | |
|---|---|---|---|
| Plasmids* | µg DNA/dish | 293 cells (average) | 293 Cre4 cells (average) |
| pCA36 | 5 | 1, 0, 0, 0 (0.3) | 1, 0, 0, 0 (0.3) |
| pCA36lox | 5 | 1, 1, 1, 0 (0.8) | 10, 18, 6, 7 (10.3) |
| pCA36loxΔ | 5 | 0, 0, 0, 0 | 6, 4, 3, 0 (3.25) |
| pCA36loxΔCreT | 5 | 2, 1, 2, 2 (1.8) | 4, 4, 2, (3.3) |
| pCA35loxΔCreITR | 5 | 14, 23, 25, 23 (21.3) | 116, 79, 83, 100 (94.5) |
| pCA35loxΔITR | 5 | 0, 0, 0, 0 (0) | 65, 62, 64, 51 (60.5) |
| pCA35loxITR | 5 | 4, 3, 4, 0 (2.8) | 114, 101, 75, 79 (92.25) |
| pFG140 (DC) | 1 | 40, 31 (35.5) | 106, 92 (99) |
| pFG14O (CE) | 1 | 21, 19 (20) | 44, 42 (43) |

*cotransfections with 5 µg pBHGloxΔE1,3 except for pFG140

TABLE 11

Cotransfections on 293 and 293Cre4 cells for rescue of LacZ vectors (±lox, ±ITR junction, ±CRE)

| | | Number of plaques/dish (average/dish) | |
|---|---|---|---|
| Genomic plasmid[a] | Shuttle plasmid[a] | 293 cells | 293Cre4 cells |
| pBHGloxΔE1,3 | pCA36 | 2, 3, 1, 2 (2) | 3, 3, 3, 1 (2.5) |
| | pCA36loxΔ | 0, 0, 0, 0 (0) | 9, 23, 20, 19 (17.8) |
| | pCA35loxITR | 26, 27, 15, 12 (20) | 91, 101, 95, 86 (93) |
| | pCA35loxΔCreITR | 56, 42, 50, 74 (55.5) | 94, 90, 96, 92 (93) |
| pBHGloxΔE1,3Cre | pCA36 | 1, 1, 0, 0 (0.5) | 2, 3, 2, 0 (1.8) |
| | pCA36loxΔ | 6, 5, 4, 3 (4.5) | 20, 14, 28, 24 (21.5) |
| | pCA35loxITR | 77, 67, 78, 76 (74.5) | 125, 120, 130, 135 (128) |
| | pCA35loxΔCreITR | 40, 46, 47, 34 (41.8) | 83, 90, 88, 89 (87.5) |
| pBHGloxΔE1,3CreR | pCA36 | 0, 0 (0) | ND[b] |
| | pCA36loxΔ | 2, 0 (1) | ND |
| | pCA35loxITR | 39, 29 (34) | ND |
| | pCA35loxΔCreITR | 7, 6 (6.6) | ND |
| pFG140 | | 61, 52 (56.5) | 85, 87 (86) |

[a]Cotransfections with 5 µg each plasmid/dish except 1 µg/dish for pFG140
[b]Not done

TABLE 12

Cotransfections on 293 and 293Cre4 cells for rescue of LacZ vectors (± lox, ± ITR junction, ± CRE)

| Genomic plasmid | Shuttle plasmid | ug DNA/ dish | Plaques/dish (average/dish) 293 cells | Plaques/dish (average/dish) 293Cre4 cells |
|---|---|---|---|---|
| pBHGloxΔE1,3 | pCA36 | 5:5 | 2, 2, 1, 0 (1.25) | 2, 1, 1, 1 (1.3) |
| | pCA36loxΔ | 5:5 | 2, 0, 0, 0 (0.5) | 26, 28, 25, 27 (26.5) |
| | pCA35loxITR | 2:2 | ND[a] | 75, 90 (82.5) |
| | | 5:5 | 3, 9, 6, 6 (6) | TNTC[b] |
| | pCA35loxΔITR | 2:2 | ND | 55, 64 (59.5) |
| | | 5:5 | 1, 2, 1, 0 (1) | TNTC |
| | pCA35loxΔCreITR | 2:2 | ND | 61, 64 (62.5) |
| | | 5:5 | 33, 28, 35, 31 (31.8) | TNTC |
| pBHGloxΔE1,3Cre | pCA36 | 5:5 | 2, 2, 1, 0 (1.25) | 4, 1, 1, 0 (1.5) |
| | pCA36loxΔ | 5:5 | 6, 4, 4, 6 (5) | 21, 25, 21, 17 (21) |
| | pCA35loxITR | 2:2 | ND | 90, 96 (93) |
| | | 5:5 | 57, 49, 45, 54 (51.3) | TNTC |
| | pCA35loxΔITR | 2:2 | ND | 75, 87 (81) |
| | | 5:5 | 39, 45, 39, 46 (42.3) | TNTC |
| | pCA35loxΔCreITR | 2:2 | ND | 117, 103 (110) |
| | | 5:5 | 54, 64, 41, 40 (49.8) | TNTC |
| pFG140 | | 1 | 114, 96 (105) | 125, 140 (132.5) |

[a]Not done
[b]Too numerous to count

TABLE 13

Cotransfections on 293 and 293Cre4 cells for rescue of LacZ vectors (CRE expressed from plasmids, by 293 cells, or both)

| Genomic plasmid | Shuttle plasmid | μgDNA/dish | Plaques/dish (average/dish) 293 cells | Plaques/dish (average/dish) 293Cre4 cells |
|---|---|---|---|---|
| pBHGloxΔE1,3 | pCA35loxITR | 5:5 | 3, 6, 9, 13 (8) | TNTC[a] (≧109) |
| | | 2:2 | 6, 4, 1, 3 (4) | 65, 55, 64, 69 (63) |
| | pCA35loxΔITR | 5:5 | 0, 0 (0) | TNTC (≧117) |
| | | 2:2 | 1, 0 (0.5) | 49, 57, 47, 54 (52) |
| | pCA35loxΔCreITR | 5:5 | 18, 21, 43 (27) | TNTC (≧111) |
| | | 2:2 | 18, 12, 21, 24 (19) | 74, 61, 50, 49 (59) |
| pBHGloxΔE1,3Cre | pCA35loxITR | 5:5 | 52, 66, 63, 57 (60) | TNTC (≧116) |
| | | 2:2 | 48, 47, 32, 43 (43) | 72, 85, 69, 75 (72) |
| | pCA35loxΔITR | 5:5 | 40, 36, 32, 63 (43) | TNTC (≧122) |
| | | 2:2 | 48, 43, 52, 46 (47) | 93, 104, 106, 100 (101) |
| | pCA35loxΔCreITR | 5:5 | 54, 56, 51 (54) | TNTC (≧68) |
| | | 2:2 | 33, 37, 35, 19 (31) | 110, 94, 89, 83 (94) |
| pFG140 | | 1 | 114 | 150 |

[a] Too numerous to count

What is claimed is:

1. A method for making an infectious adenovirus which comprises contacting a cell with or introducing into a cell:
   a. a first nucleic acid sequence being a plasmid comprising a circularized adenovirus DNA molecule having a deletion of an adenoviral packaging signal, and which, by itself, in the absence of intermolecular recombination, is incapable of generating an infectious, packageable adenovirus; and
   b. a second nucleic acid sequence which, by itself, in the absence of intermolecular recombination, is incapable of generating an infectious, packageable adenovirus, and encoding adenovirus sequences which, in the absence of adenoviral replication factors provided in trans or intermolecular recombination with said first nucleic acid sequence, are incapable of encoding an infectious, packageable adenovirus;

provided that said first and said second nucleic acid sequences each comprise a head-to-head ITR junction and sufficient overlapping adenoviral nucleic acid sequences such that homologous recombination may occur between said first and said second nucleic acid sequences, whereby said first and said second nucleic acids recombine to form said infectious adenovirus.

2. The method according to claim 1 wherein said adenovirus DNA additionally comprises at least one of (i) a deletion of, or (ii) a modification in, an adenoviral gene selected from the group consisting of adenoviral E1 sequences 3' of said packaging signal, adenoviral fibre gene sequences, adenoviral E3 gene sequences, and adenoviral E4 gene sequences.

3. A method for making an infectious adenovirus which comprises contacting a cell with or introducing into a cell:
   a. a first nucleic acid sequence encoding adenovirus sequences and which, by itself, in the absence of intermolecular recombination, is incapable of generating an infectious, packageable adenovirus; and
   b. a second nucleic acid sequence, which is a plasmid formed by combination of (i) at least one of the shuttle plasmids selected from the group consisting of pDC111, pDC112, pDC113, pDC114, pDC115, pDC116, pDC117, and pDC118, and (ii) a polycloning site or a foreign DNA or an expression cassette, and which second nucleic acid sequence, by itself, in the absence of intermolecular recombination, is incapable of generating an infectious, packageable adenovirus;

provided that said first and said second nucleic acid sequences each comprise a head-to-head ITR junction and sufficient overlapping adenoviral nucleic acid sequences such that homologous recombination may occur between said first and said second nucleic acid sequences, whereby said first and said second nucleic acids recombine to form said infectious adenovirus.

4. A recombinant adenovirus vector system comprising:
   a. a first nucleic acid sequence encoding adenovirus sequences and which, by itself, in the absence of intermolecular recombination, is incapable of generating an infectious, packageable adenovirus, said first nucleic acid sequence comprising a head-to-head ITR junction and sufficient overlapping adenoviral nucleic acid sequences such that homologous recombination with homologous sequences in a second nucleic acid sequence may occur; and
   b. the second nucleic acid sequence, which is a plasmid formed by combination of (i) at least one of the shuttle plasmids selected from the group consisting of pDC111, pDC112, pDC113, pDC114, pDC115, pDC116, pDC117, and pDC118, and (ii) a polycloning site or a foreign DNA or an expression cassette, and which second nucleic acid sequence, by itself, in the absence of intermolecular recombination, is incapable of generating an infectious, packageable adenovirus; said second nucleic acid sequence comprising a head-to-head ITR junction and sufficient overlapping adenoviral nucleic acid sequences to permit homologous recombination with said first nucleic acid sequence;

whereby said first and said second nucleic acids homologously recombine in a cell to form said infectious adenovirus.

5. A recombinant adenovirus vector system comprising:
   a. a first nucleic acid sequence encoding adenovirus sequences, and which, by itself, in the absence of inter molecular recombination, is incapable of generating an infectious, packageable adenovirus, said first nucleic acid sequence comprising a head-to-head ITR junction and sufficient overlapping adenoviral nucleic acid sequences such that homologous recombination with homologous sequences in a second nucleic acid sequence may occur; and
   b. the second nucleic acid sequence which, by itself, in the absence of intermolecular recombination, is incapable of generating an infectious, packageable adenovirus; said second nucleic acid sequence comprising a head-to-head ITR junction, an adenoviral packaging signal, and sufficient overlapping adenoviral nucleic acid sequences to permit homologous recombination with said first nucleic acid sequence;

whereby said first and said second nucleic acids homologously recombine in a cell to form said infectious, packageable adenovirus, and wherein said cell expresses adenoviral E1.

6. A kit for construction of recombinant adenovirus vectors comprising:
   (A) a first nucleic acid sequence encoding adenovirus sequences and which, by itself, in the absence of intermolecular recombination, is incapable of generating an infectious, packageable adenovirus, and said first nucleic acid sequence comprising a head-to-head ITR junction and sufficient adenoviral sequences to permit homologous recombination with similar sequences in a second nucleic acid sequence;
   (B) the second nucleic acid sequence which is a plasmid formed by combination of (i) at least one of the shuttle plasmids selected from the group consisting of pDC111, pDC112, pDC113, pDC114, pDC115, pDC116, pDC117 and pDC118, and (ii) a polycloning site or a foreign DNA or an expression cassette, and which, by itself, in the absence of intermolecular recombination, is incapable of generating an infectious, packageable adenovirus, and said second nucleic acid sequence comprising a head-to-head ITR junction and sufficient adenoviral sequences to permit homologous recombination with similar sequences in said first nucleic acid; and (C) a cell wherein, when said component (A) and said component (B) are cotransfected and recombined through homologous recombination, an infectious recombinant adenovirus vector is produced.

7. A recombinant adenovirus vector system comprising:

a. a first nucleic acid sequence comprising a deletion in the adenoviral fibre gene, and encoding other adenovirus sequences, and which, by itself, in the absence of intermolecular recombination, is incapable of generating an infectious, packageable adenovirus, said first nucleic acid sequence comprising a head-to-head ITR junction and sufficient overlapping adenoviral nucleic acid sequences such that homologous recombination with homologous sequences in a second nucleic acid sequence may occur; and b. the second nucleic acid sequence which, by itself, in the absence of intermolecular recombination, is incapable of generating an infectious, packageable adenovirus; said second nucleic acid sequence comprising a head-to-head ITR junction, an adenoviral packaging signal, and sufficient overlapping adenoviral nucleic acid sequences to permit homologous recombination with said first nucleic acid sequence;

whereby said first and said second nucleic acids homologously recombine in a cell to form said infectious, packageable adenovirus.

8. A recombinant adenovirus vector system comprising:

a. a first nucleic acid sequence encoding adenovirus sequences and which, by itself, in the absence of intermolecular recombination, is incapable of generating an infectious, packageable adenovirus, said first nucleic acid sequence comprising a head-to-head ITR junction and sufficient overlapping adenoviral nucleic acid sequences such that homologous recombination with homologous sequences in a second nucleic acid sequence may occur; and b. the second nucleic acid sequence which, by itself, in the absence of intermolecular recombination, is incapable of generating an infectious, packageable adenovirus; said second nucleic acid sequence comprising a head-to-head ITR junction, an adenoviral packaging signal, an adenoviral gene mutation, and sufficient overlapping adenoviral nucleic acid sequences to permit homologous recombination with said first nucleic acid sequence;

whereby said first and said second nucleic acids homologously recombine in a cell to form said infectious, packageable adenovirus, and wherein said adenoviral gene mutation is rescued into said infectious, packageable adenovirus.

9. The recombinant adenovirus vector system according to claim 8 wherein said adenoviral gene mutation rescued into said adenoviral vector recombinant is comprised of at least one of a mutation in the adenoviral fibre gene, a mutation in the adenoviral E4 gene, and a mutation in the adenoviral E3 gene.

* * * * *

SEQUENCE LISTING

<160> NUMBER OF SEQ ID NOS: 15

<210> SEQ ID NO 1
<211> LENGTH: 54
<212> TYPE: DNA
<213> ORGANISM: Artificial Sequence
<220> FEATURE:
<223> OTHER INFORMATION: Linkers, primers, probes

<400> SEQUENCE: 1
gatccaataa cttcgtatag catacattat acgaagttat aagtactgaa ttcg        54

<210> SEQ ID NO 2
<211> LENGTH: 54
<212> TYPE: DNA
<213> ORGANISM: Artificial Sequence

```
<220> FEATURE:
<223> OTHER INFORMATION: Linkers, primers, probes

<400> SEQUENCE: 2
gatccgaatt cagtacttat aacttcgtat aatgtatgct atacgaagtt attg        54

<210> SEQ ID NO 3
<211> LENGTH: 30
<212> TYPE: DNA
<213> ORGANISM: Artificial Sequence
<220> FEATURE:
<223> OTHER INFORMATION: Linkers,primers, probes

<400> SEQUENCE: 3
aattccccgg gagatctaag cttgagctcg                                   30

<210> SEQ ID NO 4
<211> LENGTH: 30
<212> TYPE: DNA
<213> ORGANISM: Artificial Sequence
<220> FEATURE:
<223> OTHER INFORMATION: Linkers, primers, probes

<400> SEQUENCE: 4
tcgacgagct caagcttaga tctcccgggg                                   30

<210> SEQ ID NO 5
<211> LENGTH: 47
<212> TYPE: DNA
<213> ORGANISM: Artificial Sequence
<220> FEATURE:
<223> OTHER INFORMATION: Linkers, primers, probes

<400> SEQUENCE: 5
ctagcaataa cttcgtatag catacattat acgaagttat atcgatg                47

<210> SEQ ID NO 6
<211> LENGTH: 47
<212> TYPE: DNA
<213> ORGANISM: Artificial Sequence
<220> FEATURE:
<223> OTHER INFORMATION: Linkers, primers, probes

<400> SEQUENCE: 6
ctagcatcga tataacttcg tataatgtat gctatacgaa gttattg                47

<210> SEQ ID NO 7
<211> LENGTH: 46
<212> TYPE: DNA
<213> ORGANISM: Artificial Sequence
<220> FEATURE:
<223> OTHER INFORMATION: Linkers, primers, probes

<400> SEQUENCE: 7
tgacaataac ttcgtatagc atacattata cgaagttata tcgatg                 46

<210> SEQ ID NO 8
<211> LENGTH: 46
<212> TYPE: DNA
<213> ORGANISM: Artificial Sequence
<220> FEATURE:
<223> OTHER INFORMATION: Linkers, primers, probes

<400> SEQUENCE: 8
tcacatcgat ataacttcgt ataatgtatg ctatacgaag ttattg                 46
```

<210> SEQ ID NO 9
<211> LENGTH: 14
<212> TYPE: DNA
<213> ORGANISM: Artificial Sequence
<220> FEATURE:
<223> OTHER INFORMATION: Linkers, primers, probes

<400> SEQUENCE: 9
ctagcttaat taag                                                        14

<210> SEQ ID NO 10
<211> LENGTH: 21
<212> TYPE: DNA
<213> ORGANISM: Artificial Sequence
<220> FEATURE:
<223> OTHER INFORMATION: Linkers, primers, probes

<400> SEQUENCE: 10
cgttcgaaat ttaattctag a                                                21

<210> SEQ ID NO 11
<211> LENGTH: 22
<212> TYPE: DNA
<213> ORGANISM: Artificial Sequence
<220> FEATURE:
<223> OTHER INFORMATION: Linkers, primers, probes

<400> SEQUENCE: 11
gctctagaat ttaaatttcg aa                                               22

<210> SEQ ID NO 12
<211> LENGTH: 42
<212> TYPE: DNA
<213> ORGANISM: Artificial Sequence
<220> FEATURE:
<223> OTHER INFORMATION: Linkers, primers, probes

<400> SEQUENCE: 12
ctagagaatt caggcctgct agcagatcta agcttgagct cg                         42

<210> SEQ ID NO 13
<211> LENGTH: 42
<212> TYPE: DNA
<213> ORGANISM: Artificial Sequence
<220> FEATURE:
<223> OTHER INFORMATION: Linkers, primers, probes

<400> SEQUENCE: 13
tcgacgagct caagcttaga tctgctagca ggcctgaatt ct                         42

<210> SEQ ID NO 14
<211> LENGTH: 48
<212> TYPE: DNA
<213> ORGANISM: Artificial Sequence
<220> FEATURE:
<223> OTHER INFORMATION: Linkers, primers, probes

<400> SEQUENCE: 14
ctagagtcga cgagctcagg cttagatctg ctagcaggcc tgaattcg                   48

<210> SEQ ID NO 15
<211> LENGTH: 49
<212> TYPE: DNA
<213> ORGANISM: Artificial Sequence -continued

```
<220> FEATURE:
<223> OTHER INFORMATION: Linkers, primers, probes

<400> SEQUENCE: 15
gatcgcgaat tcaggcctgc tagcagatct aagcttgagc tcgtcgact              49
```